(12) United States Patent
Banbury et al.

(10) Patent No.: US 7,513,902 B2
(45) Date of Patent: Apr. 7, 2009

(54) SKIN LESION EXCISER AND SKIN-CLOSURE DEVICE THEREFOR

(75) Inventors: Michael K. Banbury, Cleveland Heights, OH (US); Jillian E. Banbury, Cleveland Heights, OH (US); Craig B. Berky, Milford, OH (US); Warren P. Williamson, IV, Loveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 634 days.

(21) Appl. No.: 10/845,313

(22) Filed: May 13, 2004

(65) Prior Publication Data

US 2004/0215217 A1   Oct. 28, 2004

Related U.S. Application Data

(63) Continuation-in-part of application No. 10/261,155, filed on Sep. 30, 2002.

(60) Provisional application No. 60/357,520, filed on Feb. 15, 2002, provisional application No. 60/326,254, filed on Oct. 1, 2001.

(51) Int. Cl.
*A61B 17/50* (2006.01)

(52) U.S. Cl. .................... 606/131; 606/215

(58) Field of Classification Search ............ 606/110, 606/111, 113, 114, 131, 132, 137, 139–142, 606/120, 215–217, 151, 157, 158, 210, 213; 227/180.1

See application file for complete search history.

(56) References Cited

U.S. PATENT DOCUMENTS

| | | | |
|---|---|---|---|
| 363,538 A | 5/1887 | Penny | |
| 2,232,142 A | 2/1941 | Schumann | |
| 2,254,620 A | 9/1941 | Miller | |
| 2,371,978 A | 3/1945 | Perham | |
| 2,684,070 A | 7/1954 | Kelsey | |
| 2,994,321 A | 8/1961 | Tischler | |
| 3,068,870 A | 12/1962 | Levin | |
| 3,323,208 A | 6/1967 | Hurley, Jr. | |
| 3,353,531 A | 11/1967 | Armao | |
| 3,373,742 A | 3/1968 | Shears et al. | |
| 3,391,690 A | 7/1968 | Armao | |
| 3,487,836 A | 1/1970 | Niebel et al. | |
| 3,520,306 A | 7/1970 | Gardner et al. | |
| 3,522,809 A | 8/1970 | Cornell | |
| 3,586,002 A | 6/1971 | Wood | |
| 3,707,970 A | 1/1973 | Smirnov et al. | |

(Continued)

FOREIGN PATENT DOCUMENTS

DE        31 11 996 A1        10/1982

(Continued)

*Primary Examiner*—Julian W Woo
(74) *Attorney, Agent, or Firm*—Tarolli, Sundheim, Covell & Tummino LLP

(57) ABSTRACT

A device for excising tissue and closing a wound that results from excision of the tissue includes structure defining an aperture into which tissue to be excised is exposed. The device also includes a cutting member for excising the tissue, a closure member for closing the wound, and an actuatable drive member associated with the structure. The drive member is actuatable to move the cutting member relative to the aperture for excising the tissue that is exposed in the aperture and for closing the wound with the closure member.

7 Claims, 35 Drawing Sheets

U.S. PATENT DOCUMENTS

| | | | |
|---|---|---|---|
| 3,857,140 A | 12/1974 | Leveen | |
| 3,867,944 A | 2/1975 | Samuels | |
| 4,192,312 A | 3/1980 | Wilson | |
| 4,399,810 A | 8/1983 | Samuels et al. | |
| 4,465,071 A | 8/1984 | Samuels et al. | |
| 4,467,805 A | 8/1984 | Fukuda | |
| 4,505,274 A | 3/1985 | Speelman | |
| 4,523,592 A | 6/1985 | Daniel | |
| 4,542,742 A | 9/1985 | Winkelman et al. | |
| 4,576,163 A | 3/1986 | Bliss | |
| 4,610,251 A | 9/1986 | Kumar | |
| 4,651,753 A | 3/1987 | Lifton | |
| 4,682,598 A * | 7/1987 | Beraha | 606/142 |
| 4,754,756 A | 7/1988 | Shelanski | |
| 4,807,622 A * | 2/1989 | Ohkaka et al. | 606/120 |
| 4,815,468 A | 3/1989 | Annand | |
| 4,865,026 A | 9/1989 | Barrett | |
| 4,943,295 A | 7/1990 | Hartlaub et al. | |
| 4,950,284 A | 8/1990 | Green et al. | |
| 4,955,897 A * | 9/1990 | Ship | 606/210 |
| 4,976,909 A | 12/1990 | Dorband et al. | |
| 5,099,827 A | 3/1992 | Melzer et al. | |
| 5,123,907 A | 6/1992 | Romaine | |
| 5,123,908 A | 6/1992 | Chen | |
| 5,176,703 A | 1/1993 | Peterson | |
| 5,190,560 A | 3/1993 | Woods et al. | |
| 5,209,755 A | 5/1993 | Abrahan et al. | |
| 5,212,879 A | 5/1993 | Biro et al. | |
| 5,213,907 A | 5/1993 | Caballero | |
| 5,219,354 A | 6/1993 | Choudhury et al. | |
| 5,258,012 A | 11/1993 | Luscombe et al. | |
| 5,304,204 A | 4/1994 | Bregen | |
| 5,358,510 A | 10/1994 | Luscombe et al. | |
| 5,423,857 A | 6/1995 | Rosenman et al. | |
| 5,425,740 A | 6/1995 | Hutchinson, Jr. | |
| 5,425,741 A | 6/1995 | Lemp et al. | |
| 5,531,760 A | 7/1996 | Alwafaie | |
| 5,555,892 A | 9/1996 | Tipton | |
| 5,588,967 A | 12/1996 | Lemp et al. | |
| 5,609,600 A | 3/1997 | Love et al. | |
| 5,620,452 A | 4/1997 | Yoon | |
| 5,624,451 A | 4/1997 | Segal | |
| 5,628,759 A | 5/1997 | McCool et al. | |
| 5,674,234 A | 10/1997 | McCool et al. | |
| 5,868,763 A | 2/1999 | Spence et al. | |
| 5,925,052 A * | 7/1999 | Simmons | 606/120 |
| 5,931,847 A | 8/1999 | Bittner et al. | |
| 5,993,399 A | 11/1999 | Pruitt et al. | |
| 6,007,552 A * | 12/1999 | Fogarty et al. | 606/157 |
| 6,015,417 A | 1/2000 | Reynolds, Jr. | |
| 6,126,615 A | 10/2000 | Allen et al. | |
| 6,146,399 A | 11/2000 | Lee | |
| 6,152,936 A * | 11/2000 | Christy et al. | 606/140 |
| 6,190,397 B1 | 2/2001 | Spence et al. | |
| 6,273,897 B1 * | 8/2001 | Dalessandro et al. | 606/139 |
| 6,319,474 B1 | 11/2001 | Krulevitch et al. | |
| 6,565,581 B1 | 5/2003 | Spence et al. | |
| 6,638,235 B2 | 10/2003 | Miller et al. | |
| 6,719,777 B2 | 4/2004 | Ginn et al. | |
| 6,758,824 B1 | 7/2004 | Miller et al. | |
| 6,773,439 B2 * | 8/2004 | George et al. | 606/141 |
| 6,811,555 B1 | 11/2004 | Willis et al. | |
| 6,981,983 B1 | 1/2006 | Rosenblatt et al. | |
| 2002/0082641 A1 | 6/2002 | Ginn et al. | |
| 2003/0208231 A1 | 11/2003 | Williamson, IV et al. | |
| 2004/0009289 A1 | 1/2004 | Carley et al. | |
| 2004/0010285 A1 | 1/2004 | Carley et al. | |
| 2004/0039414 A1 | 2/2004 | Carley et al. | |
| 2004/0073236 A1 | 4/2004 | Carley et al. | |

FOREIGN PATENT DOCUMENTS

| | | |
|---|---|---|
| DE | 198 58 581 A1 | 7/2000 |
| EP | 0 092 383 A2 | 10/1983 |
| EP | 0 619 985 A1 | 10/1994 |
| EP | 0 622 046 A2 | 11/1994 |
| WO | WO 95/34245 | 12/1995 |
| WO | WO 00/56227 A1 | 9/2000 |
| WO | WO 03/028563 A2 | 1/2003 |

* cited by examiner

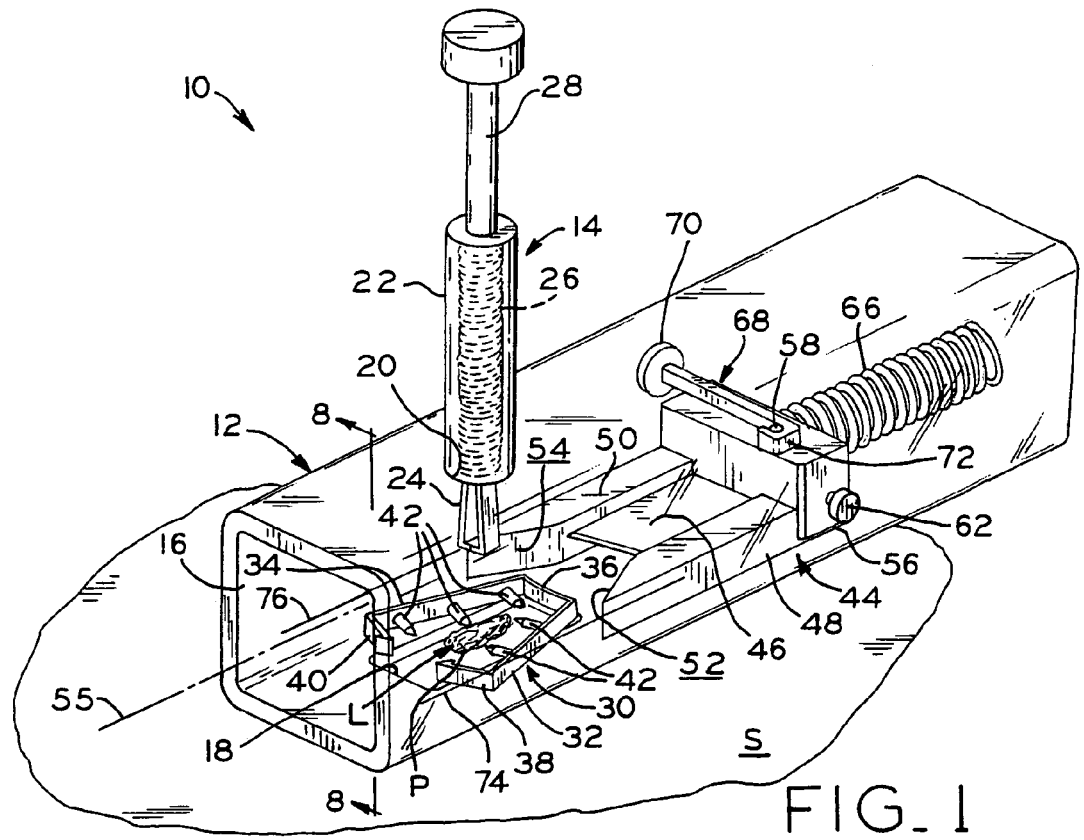
FIG_1
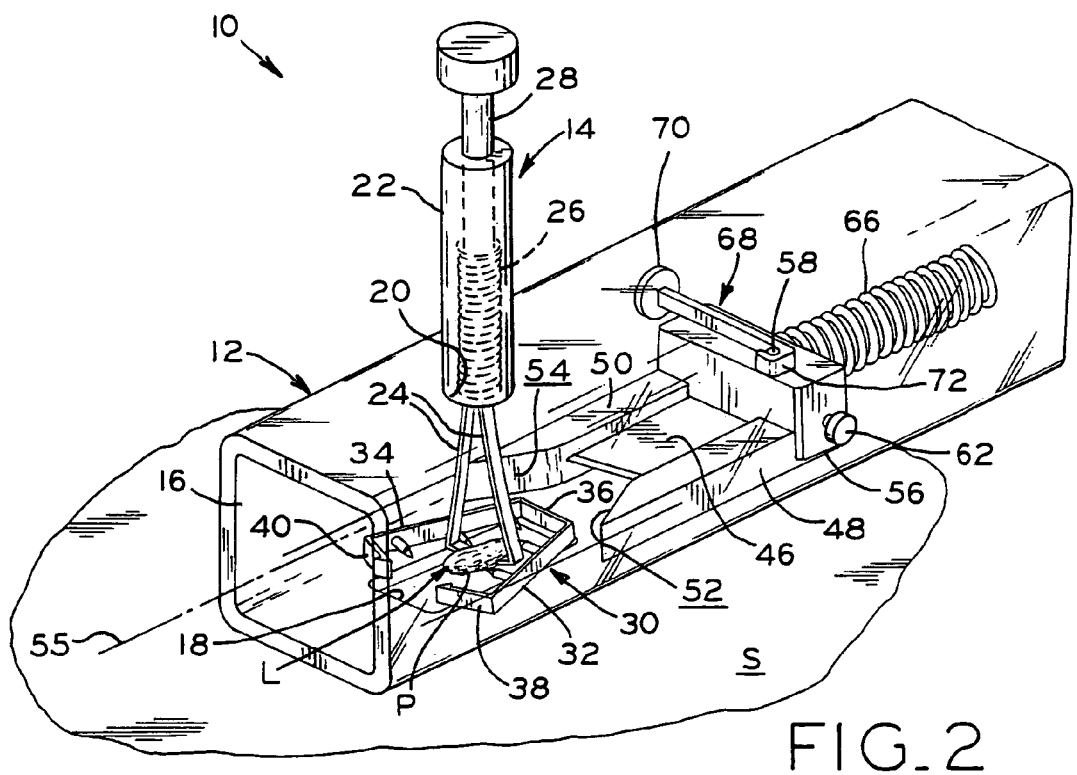
FIG_2

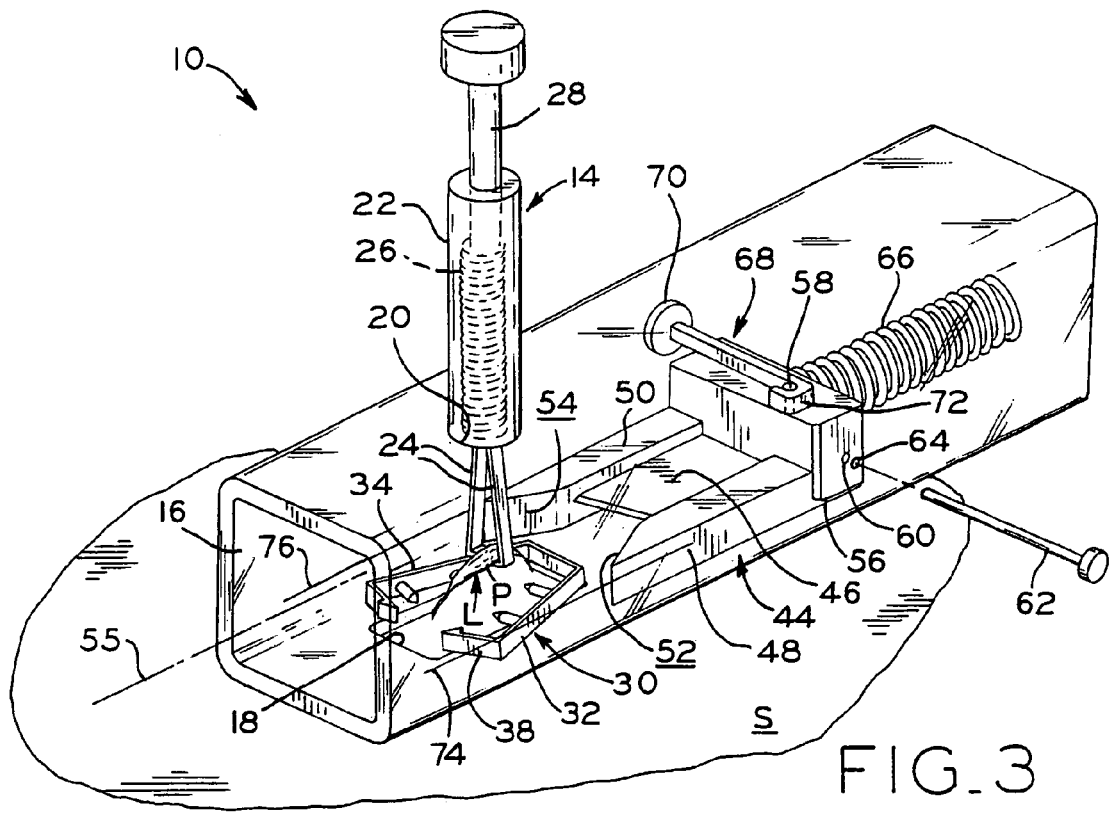
FIG_3
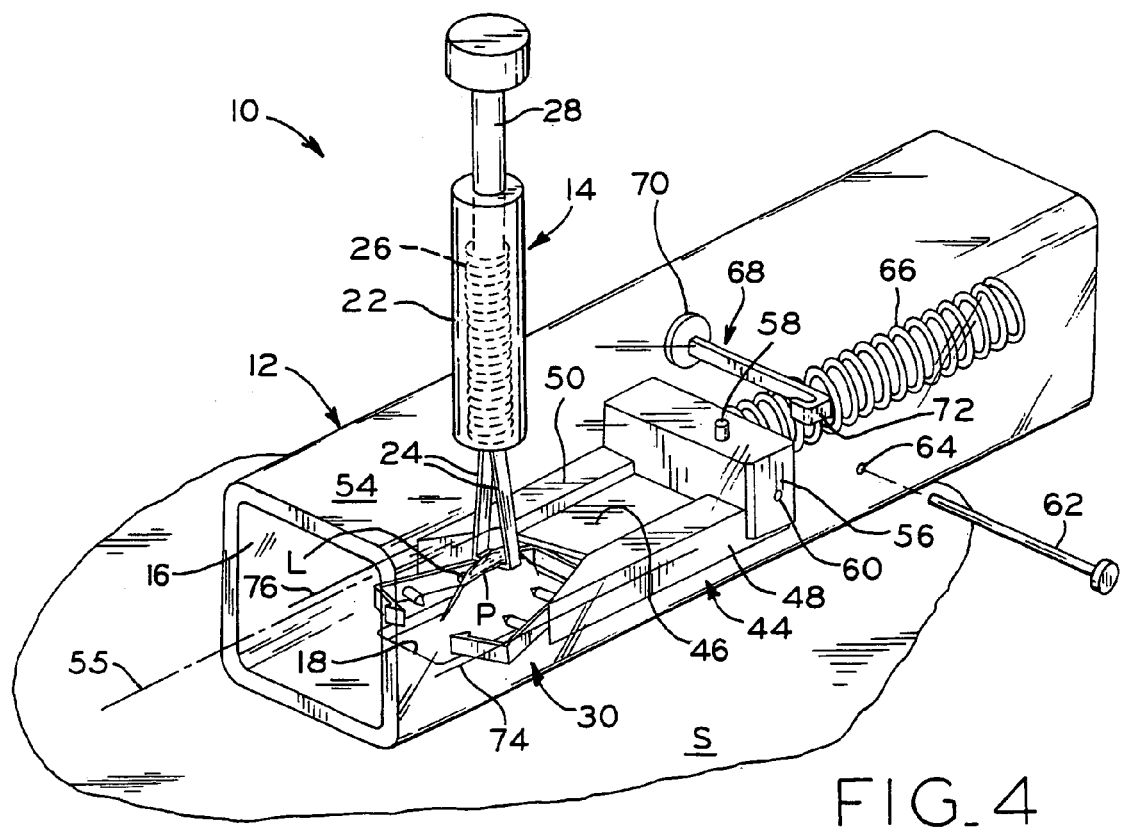
FIG_4

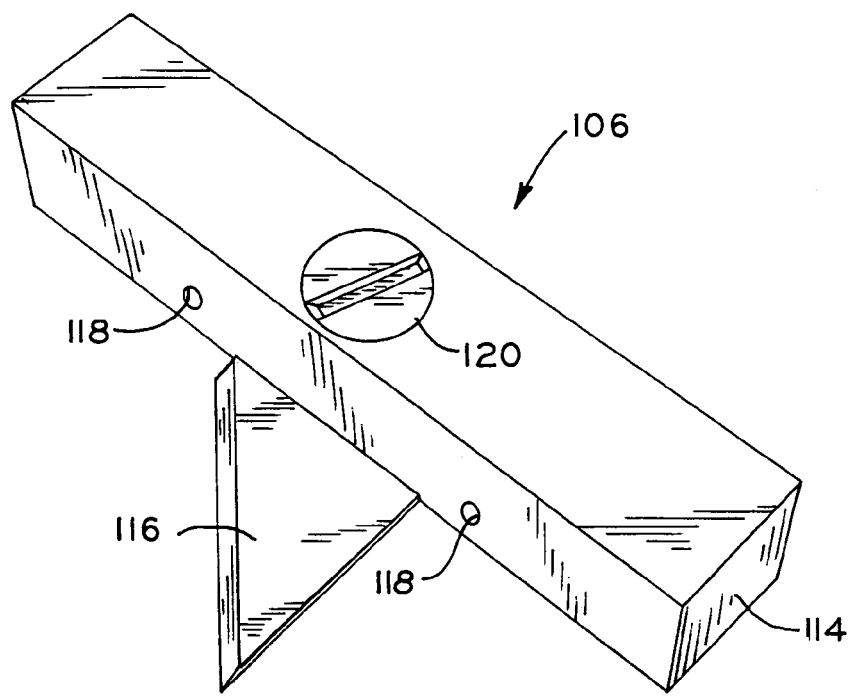
FIG_13
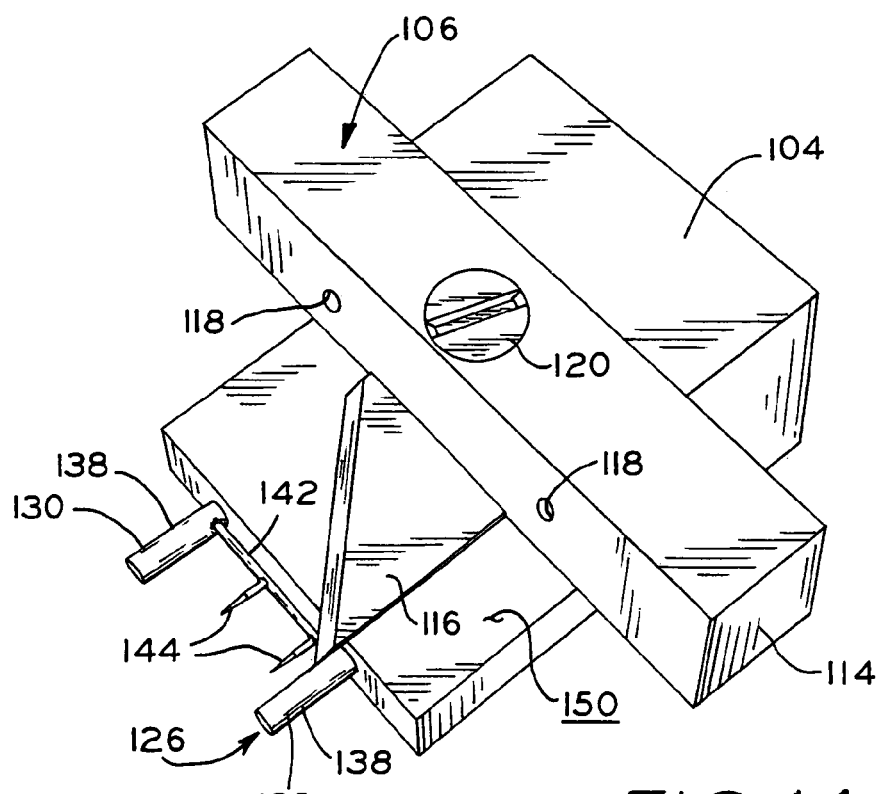
FIG_14

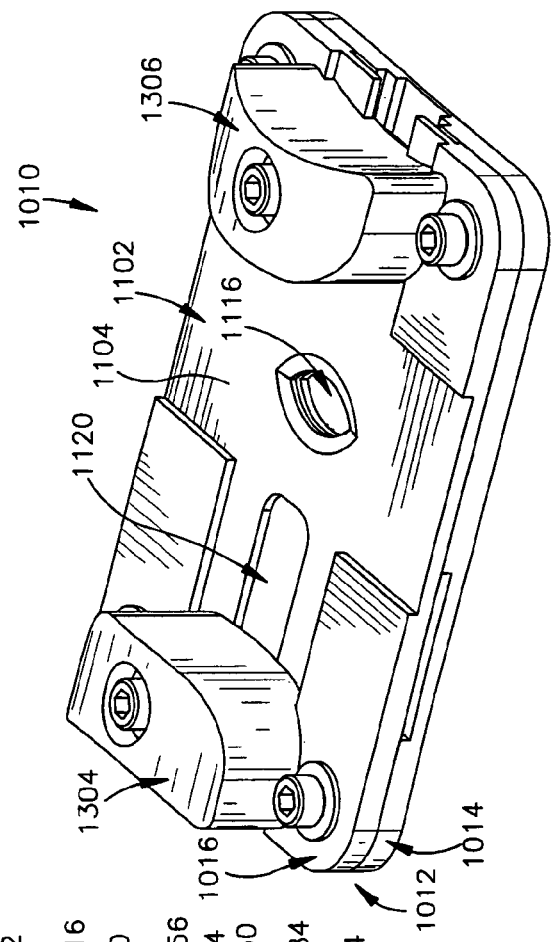

SKIN LESION EXCISER AND SKIN-CLOSURE DEVICE THEREFOR

CROSS REFERENCE TO RELATED APPLICATIONS

This application is a continuation-in-part of co-pending patent application Ser. No. 10/261,155, filed Sep. 30, 2002, which claims priority to provisional patent application Nos. 60/326,254, filed Oct. 1, 2001, and 60/357,520, filed Feb. 15, 2002.

BACKGROUND OF THE INVENTION

1. Field of Invention

The present invention relates to the excision of skin tags, moles, lesions and other types of discrete patches or points on the skin (herein collectively referred to as lesions) from a human or animal.

2. Description of the Related Art

In 1996, the Center for Disease Control estimated that approximately 2 million skin lesions were excised (from humans) per year in the United States. This estimate was based on voluntary reporting by several centers and is most likely an underestimate of the actual number of skin lesions excised. In that same year, it was estimated that approximately 8 million skin lesions were excised (again, from humans) per year in industrialized nations worldwide.

The current medical practice model for treatment of skin cancer involves preliminary screening of skin lesions. This requires surgical excision of the skin lesion typically done in the office of a plastic surgeon. Alternative methods by which dermatologists can biopsy lesions in screening for cancer include shaving small segments for microscopic analysis, or punch biopsy. A punch biopsy involves coring out a small sample of the skin lesion and then leaving the skin defect open with a covering bandage. Because it is such a small sample, no skin closure is used.

When an individual identifies a mole or skin lesion that he or she wishes excised, either for cosmetic purposes or screening for skin cancer, the first approach is often a visit to the family practice physician or internist. At that time, evaluation of the lesion is performed and if necessary, referral to the dermatologist or plastic surgeon is given.

Plastic surgeons or other physicians performing surgical excision typically prepare and drape the area, inject the area locally with an anesthetic such as lidocaine, and then perform a surgical excision using a scalpel. The skin is re-approximated and closed using suture material, which is sewn and then tied.

These methods of skin lesion excision can be awkward, time consuming and inconvenient. Often patients fail to follow up with screening for skin lesions because of the inconvenience and fear of surgical procedures even though minor. A device and/or method of simply and effectively excising skin lesions while the underlying skin is simultaneously re-approximated and closed is highly desirable. Patients would then be more likely to follow through with the procedures and derive greater satisfaction overall. This would also lead to earlier detection of skin cancer when it is more easily treated.

SUMMARY OF THE INVENTION

In accordance with the present invention, devices and methods are provided by which skin lesions are excised safely and effectively with substantially simultaneous closure of the skin. The excision and closure of the excision site through use of the present invention could change the paradigm for screening and treatment of skin cancer in the industrialized world.

The inventive devices are quick and easy to manipulate, and the method requires only a minimum of local anesthesia or analgesia for patient comfort. The inventive methods could be performed in the office of the internist or family practice physician where the patient initially presents and often by a physician extender, such as a nurse practitioner, under the supervision and guidance of the physician.

Through use of the present invention, it would be unnecessary for patients to make a secondary appointment with another physician for examination and potential excision of the lesion. The usual 30-minute procedure could be reduced to 2 or 3 minutes using the present invention. Moreover, the excised lesion may be easily retrieved from the inventive device and submitted for pathologic examination.

The present invention also provides a device for excising tissue and closing a wound that results from excision of the tissue. The device comprises structure defining an aperture into which tissue to be excised is exposed, a cutting member for excising the tissue, a closure member for closing the wound, and an actuatable drive member associated with the structure. The drive member is actuatable to move the cutting member relative to the aperture for excising the tissue that is exposed in the aperture and for closing the wound with the closure member.

The present invention also provides a method for excising tissue and closing a wound that results from excision of the tissue. The method comprises the steps of: exposing the tissue to be excised into an aperture formed in a structure; moving a portion of a drive member over a first distance to move a closure member into engagement with the tissue that is exposed in the aperture; moving the drive member over a second distance beyond the first distance so as to move a cutting member relative to the aperture for excising the tissue that is exposed in the aperture; and moving the drive member over a third distance beyond the second distance for closing the wound with the closure member.

The present invention still further provides a method for excising tissue and closing a wound that results from excision of the tissue. The method comprises the steps of exposing the tissue to be excised into an aperture formed in a structure; moving a portion of a drive member over a first distance to move a closure member into a closed condition for clamping the tissue that is exposed in the aperture; moving the drive member over a second distance beyond the first distance so as to move a cutting member relative to the aperture for excising the tissue that is exposed in the aperture.

The present invention also provides an exciser for excising tissue. The exciser comprises structure defining an aperture into which tissue to be excised is exposed, a cutting member for excising the tissue, and an actuatable drive member associated with the structure. The drive member is actuatable to move the cutting member relative to the aperture for excising the tissue that is exposed in the aperture. The exciser also comprises an actuator handle that is associated with the drive member. Movement of the actuator handle relative to the structure actuates the drive member.

The present invention also provides a method of excising tissue. The method comprises the steps of: exposing tissue into an aperture defined in a structure; supporting a cutting member on an actuatable drive member that is movable relative to the structure; associating an actuator handle to the drive member; and moving the actuator handle to actuate the drive member to move the cutting member relative to the aperture for excising the tissue that is exposed in the aperture.

The present invention also provides a closure member for clamping tissue adjacent a wound. The closure member comprises a planar body portion including first and second retaining portions and a deformable portion that connects the first and second retaining portions. The closure member has an open condition in which the deformable portion spaces the first and second retaining portions apart from one another so that the tissue to be clamped may be placed between the first and second retaining portions. The closure member also has a closed condition in which the deformable portion is elastically deformed to bring the first and second retaining portions together to clamp the tissue between the first and second retaining portions. The body portion of the closure member is planar in both the open and closed conditions. The closure member further includes a first set of tines that extends outwardly of the first retaining portion and a second set of tines that extends outwardly of the second retaining portion. The first and second sets of tines engage the tissue to secure the body portion to the tissue when the closure member is in the closed condition.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1 is an oblique view of a first embodiment of the inventive device positioned against the skin of the patient and in a first state, prior to lesion excision, with the forceps retracted;

FIG. 2 shows the device of FIG. 1 in a second, sequential state, prior to lesion excision, with the forceps extended and capturing the lesion to be excised;

FIG. 3 shows the device of FIG. 1 in a third, sequential state, prior to lesion excision, with the forceps shown in a lesion-pulling position and the safety pin removed;

FIG. 4 shows the device of FIG. 1 in a fourth, sequential state, during lesion excision, with the staple partially closed through the skin surrounding the lesion;

FIG. 13 is an oblique view of the blade assembly of the device of FIG. 9;

FIG. 14 is an oblique view of the blade assembly of FIG. 13 fitted to the second applicator block of FIG. 12;

FIG. 41 is a plan view of the drive member in a fourth position relative to the base plate portion;

FIG. 42 is an oblique view of a second exemplary device constructed in accordance with the fifth embodiment of the present invention;

Corresponding reference characters indicate corresponding parts throughout the several views. The exemplifications set out herein illustrate various embodiments of the invention and such exemplifications are not to be construed as limiting the scope of the invention in any manner.

DETAILED DESCRIPTION OF THE INVENTION

Figure 5:
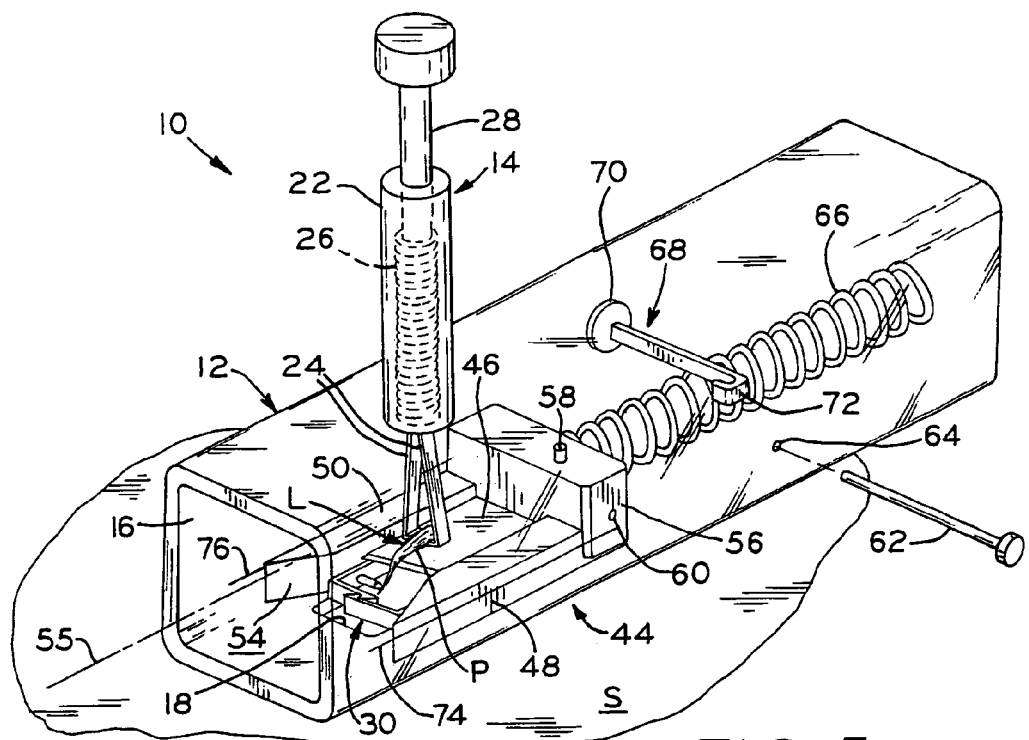
FIG. 5 shows the device of FIG. 1 in a fifth, sequential state, during lesion excision, with the staple more fully closed.

FIG. 1 shows exciser 10, a first embodiment of the present invention which includes base assembly 12 and separable forceps assembly 14. It is envisioned that exciser 10 may be a single use device, all or part of which may be discarded after a lesion has been excised therewith.

Base assembly 12 includes transparent, elongate plastic housing or frame 16 which, as shown, has the shape of a parallelepiped. It is envisioned, however, that housing 16 may be of any suitable shape. The lower side of housing 16, that side which, in use, lies against skin S of the patient, is provided with rectangular first aperture 18 which frames lesion L to be excised. At a location directly opposite first aperture 18, the upper side of housing 16 is provided with circular second aperture 20 into which the end of cylindrical body 22 of forceps assembly 14 is inserted.

Forceps assembly 14 further includes forceps or tweezers 24 having a pair of elongate, separable, somewhat flexible arms which are retractable into and extendable from the interior of cylindrical forceps body 22, and spring 26 which acts to urge tweezers 24 into the interior body 22. Forceps assembly 14 is also provided with plunger 28 which, when depressed with the thumb, urges tweezers 24 out of body 22 against the action of spring 26, the extended tweezers urged into an open position in which its arms are spread. Release of plunger 28 allows spring 26 to force tweezers 24 upwardly and into body 22, closing the tweezers. Those of ordinary skill in the art will recognize that forceps assembly 14 may include a mechanism similar to slender, elongate tools commonly used by mechanics for grasping small parts such as screws and nuts, for example, which have been dropped into hard to reach places. Such grasping tools typically employ spring-biased tweezers which are opened by depression of a plunger, as described above. Alternatively, forceps assembly 14 may include a mechanism (not shown) by which tweezers 24 are similarly extended from a body and opened, or retracted into the body and closed, by turning a screw threaded into the body, the tip of the screw attached to the tweezers inside the body. As a further, unshown alternative, second aperture 20 may be enlarged, or housing 16 otherwise adequately fashioned to allow the lesion to be manually captured with an ordinary pair of tweezers or forceps.

Disposed inside housing 16, adjacent to first aperture 18, is a skin-closure device which may be made of a surgical stainless steel or a suitable plastic material: Unitary staple 30, in its opened condition, is somewhat V-shaped, having a pair of distant, splayed straight legs, 32 and 34, each having an end integrally connected to central portion 36 which extends between one end of the legs. The free end of legs 32 and 34 are respectively provided with barbs 38 and 40 which, when the legs are proximate and the staple is closed, interlock and hold the staple in its closed condition. Staple 30 may be lightly adhered to the inside surface of housing 16 to help maintain its position prior to being closed.

The interfacing, or inward sides of legs 32 and 34 are provided with a plurality of pointed pins 42 which extend therefrom and which, when the staple is closed, are alternating relative to the legs from which they extend. When the staple is closed, and pins 42 extend through the skin below the excision site, the pointed free end of each pin 42 abuts or is at least proximal the inward side of the opposite leg. It is to be understood that staple 30, and/or any of the other skin-closure devices or staples described further herein below, are exemplary embodiments which may be adapted for use with the inventive excisers. It is envisioned that other types of skin-closure devices which serve to close or maintain closed the skin at the lesion excision site may also be in accordance with the present invention, and such devices or the use thereof fall within the scope of the present invention.

Housing 16 is provided with inverted U-shaped clip 43 (FIG. 8) which is integrally molded or otherwise attached thereto at the edge of rectangular first aperture 18 nearest blade assembly 44. Clip 43 surrounds three sides of staple central portion 36 to prevent its movement longitudinally of housing 16 when engaged by the blade assembly, as disclosed further below. Notably, the opening of clip 43 is located over first aperture 18 such that, upon removal of base assembly 12 from the skin of the patient after excision of the lesion, closed staple 30 may exit the housing with clearance between its central portion 36 and the adjacent edge of first aperture 18. Note that excisers and skin-closure devices of different sizes may be provided to accommodate the excision various sized lesions and closure of skin at the excision site.

Also disposed within housing 16 is blade assembly 44 which includes surgical steel blade 46 fixed between wedges or hammers 48 and 50. Hammers 48 and 50 are staple-engaging portions of blade assembly 44 and are provided with surfaces 52 and 54 which are curved or flat and are oblique to the longitudinal axis 55 of housing 16. As will be described further hereinbelow, during actuation of exciser 10, hammers 48 and 50 and blade 46 move coincidentally such that surfaces 52 and 54 slidably engage legs 32 and 34 of staple and move legs 32 and 34 together, thereby closing the staple and the skin simultaneously with the excision of the lesion from the skin by blade 46. Notably, the sharp edge of blade 46 is located adjacent to surfaces 52 and 54, and slicing of the lesion from the skin occurs as opposite portions of legs 32 and 34 along axis 55 are squeezed together by surfaces 52 and 54 to their closed distance from each other. Notably, too, above-described clip 43 is located well beneath blade 46 so that the clip will not interfere with the blade's movement.

Blade assembly 44 further includes block 56 to which hammers 48 and 50 and blade 46 are attached. Block 56 is provided with post 58 which extends vertically and hole 60 (FIGS. 3-7) which extends laterally. Base assembly 12 is also provided with removable elongate safety pin 62 which, prior to actuation of exciser 10, extends into hole 60 and through hole 64 in housing 16.

Compression spring 66 is provided inside housing 16, and has one end fixed relative to the housing; the other end abuts block 56. Spring 66 thus urges blade assembly 44 from its cocked position along axis 55 toward staple 30. With safety pin 62 installed, blade assembly 44 is retained in its cocked position against the force of compression spring 66 and may not be inadvertently actuated or triggered. With safety pin 62 installed, blade assembly 44 thus may not be slidably moved within housing 16 along axis 55. Base assembly 12 also provided with plunger 68 which extends through the lateral wall of housing 16 and has head 70, the depression of which triggers blade assembly 44 once safety pin 62 has been removed.

Plunger 68 is provided with J-shaped latching end or hook 72 which, in the blade assembly cocked position, partially surrounds post 58, the free end of hook 72 extending laterally in a direction perpendicular to axis 55 and abutting the post. Depression of plunger head 70 moves plunger 68 laterally such that post 58 is no longer captured within hook 72 and, with safety pin 62 removed, spring 66 will then immediately force blade assembly 44 to move along axis 55 toward the lesion and staple 30.

The operation of exciser 10 will now be described with sequential reference to FIGS. 1-7. The body 16 of base assembly 12 is placed against skin S of the patient such that lesion L to be excised is framed by aperture 18, and safety pin 62 is removed. Referring to FIG. 2, plunger 28 of forceps assembly 14 is depressed against spring 26 and tweezers 24 are extended into the interior of housing 16 and expand. The free ends of tweezers 24, which may be serrated for enhanced gripping ability, acquire or grab the lesion and, with reference to FIG. 3, plunger 28 is released. Under the influence of spring 26, tweezers 24 are at least partially retracted into cylindrical body 22 and pull the lesion upwardly through aperture 18. Parallel lines 74 and 76 are etched or printed onto the transparent lateral sides of body 16, and blade 46 lies and moves in a plane containing lines 74 and 76; these lines thus establish the location on the skin at which the lesion will be excised by the blade.

Figure 8:
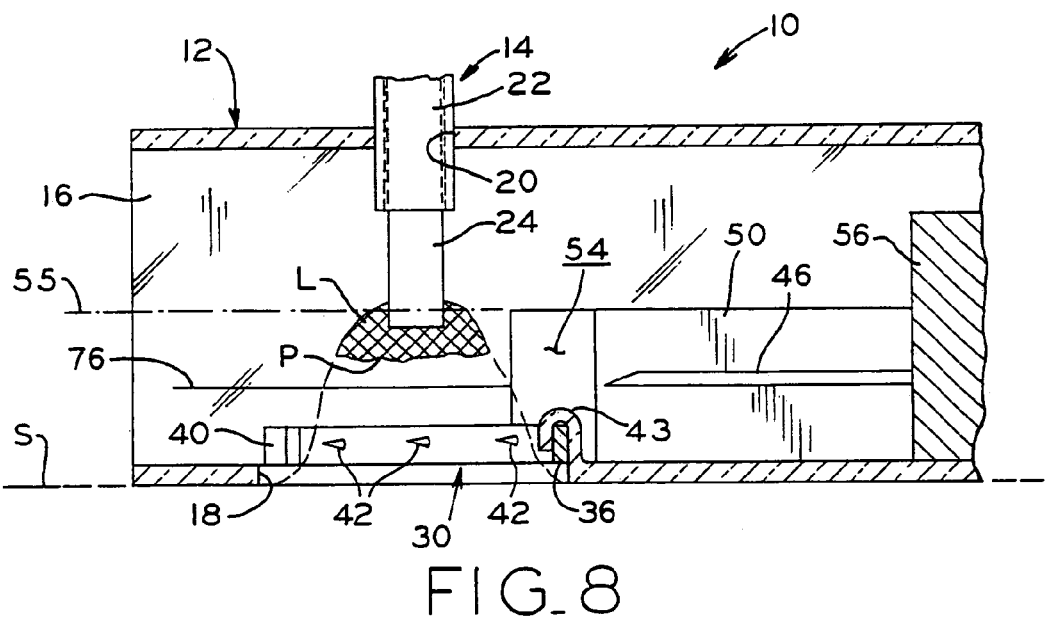
FIG. 8 is an enlarged fragmentary sectional view of the exciser of FIG. 1 along line 8-8, showing the staple retention feature of the housing and the position of a lesion to be excised from the skin.

Because body 16 is transparent, the doctor or nurse practitioner can establish the desired elevated position of the lesion by first sighting lines 74 and 76 laterally through the body such that they are viewed as being superposed, and adjusting the lesion with forceps assembly 14, if and as necessary, such that perimeter P of lesion L, which may be irregularly shaped, is pulled to a position above the superposed lines, as best shown in FIG. 8. So positioned, the lesion will, after actuation of the blade assembly, be placed in proximity to blade 46 which cuts the skin located outside lesion perimeter P. In adjusting forceps assembly 14, its body 22 may be moved relative to base assembly housing 16, or its plunger 28 may be pulled further upward, drawing tweezers 24 further into body 22. Alternatively, as mentioned above, the lesion may be captured manually using an ordinary pair of tweezers or forceps and appropriately positioned prior to triggering blade assembly 44. As a further alternative, the lesion may be captured with a skin hook (not shown) and appropriately positioned prior to triggering the blade.

Once the lesion is in its desired position within housing 16, blade assembly 44 is triggered by depression of plunger head 70. In immediate response to the free end of plunger hook 72 sliding clear of block post 58, blade assembly 44 quickly moves along axis 55. Blade 46 passes below the free ends of tweezers 24 and through the skin outside of lesion perimeter P, slicing the lesion from the skin while staple 30 simultaneously closes the skin at a location below the excision site. During closure of staple 30, as surfaces 52 and 54 of hammers 48 and 50 slidably engage and close legs 32 and 34, pins 42 pierce and protrude through the skin of the patent, and hold the staple in place and prevent it from being pulled from the re-approximated skin after closure. During the simultaneous excision and closure, the shorn edges of the skin on opposite sides of the excision are captured between staple legs 32, 34, and are upwardly diverted, resulting in a desirable, elliptically-shaped closure. Further, the dermis of these shorn skin edges, rather than merely the epidermis, is brought into abutting contact, thereby allowing the stronger parts of the skin to mend together and speeding the excision site healing time.

Figure 6:
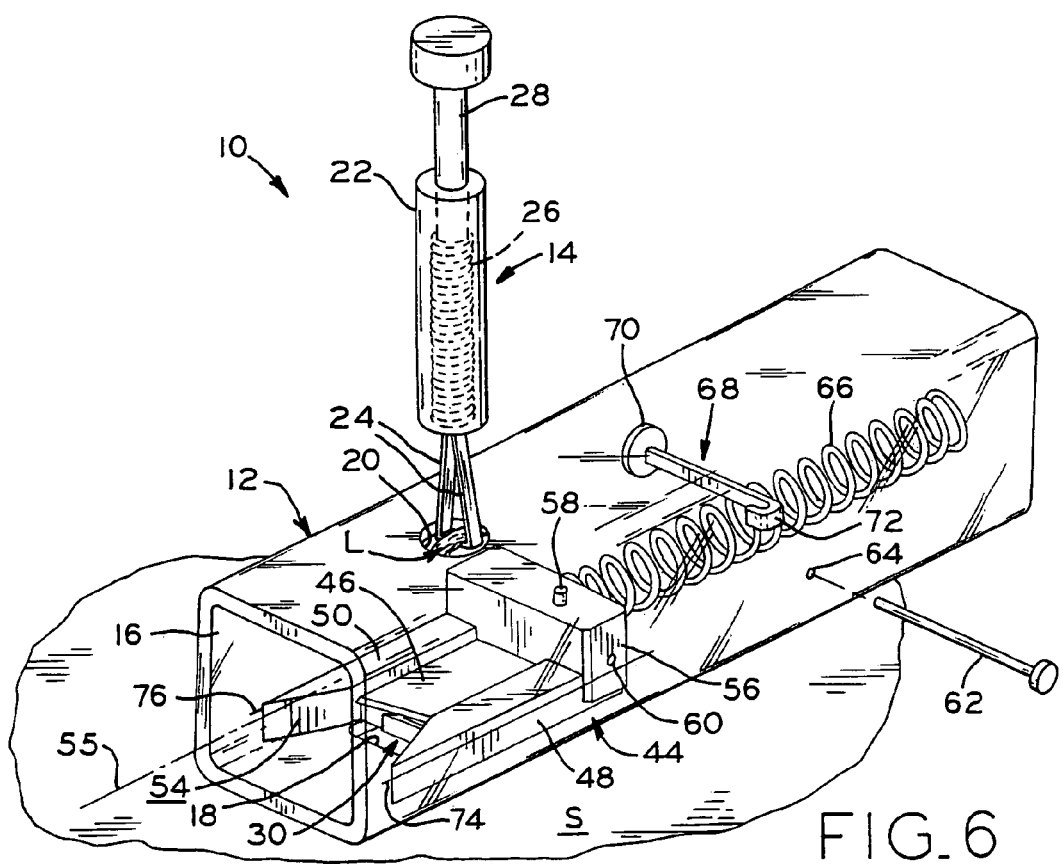
FIG. 6 shows the device of FIG. 1 in a sixth, sequential state, after lesion excision, with the staple fully closed, the forceps being withdrawn from the device and removing the lesion from the skin.
Figure 7:
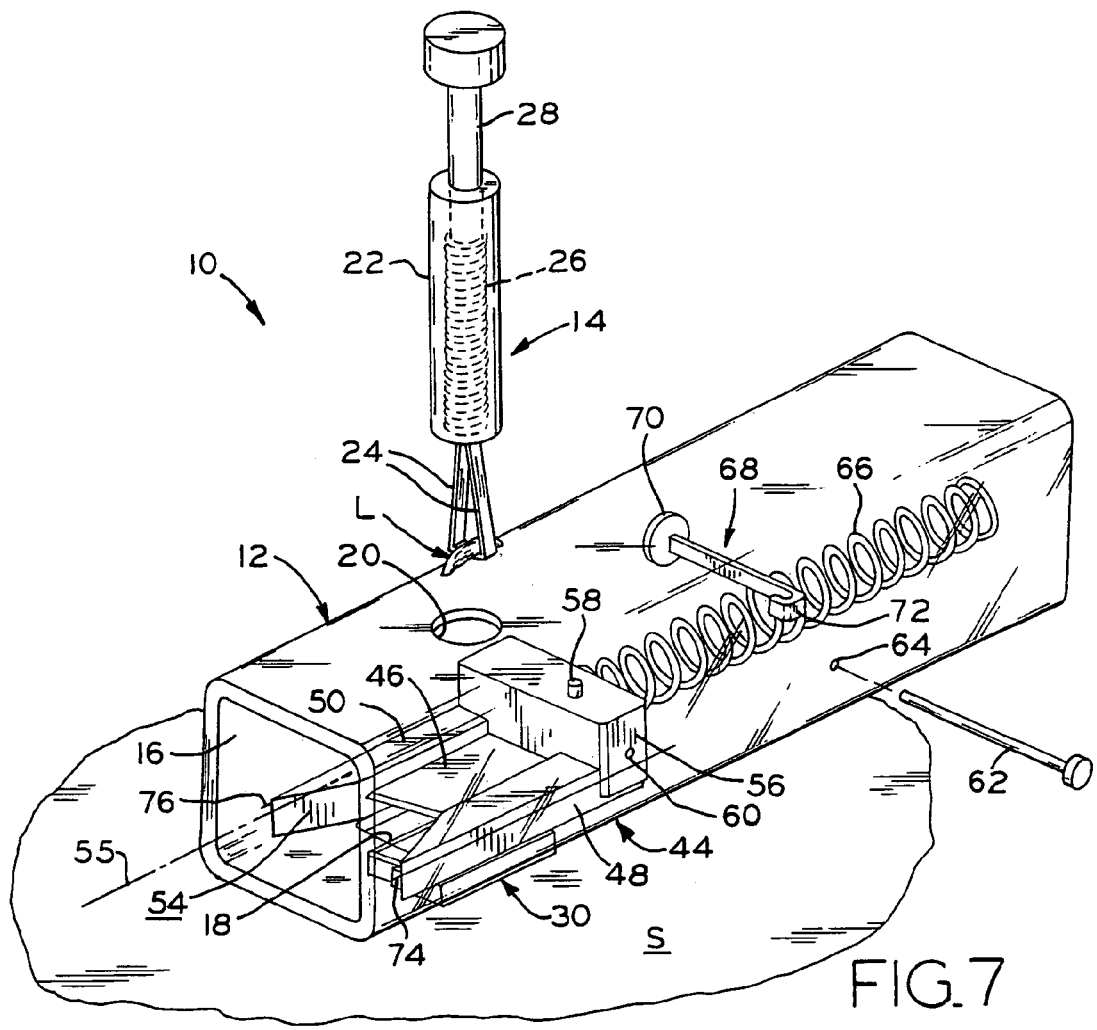
FIG. 7 shows the device of FIG. 1 in a seventh, sequential state, after lesion excision, the device housing being removed from the skin, the forceps holding the excised lesion fully removed from the device housing.

Referring to FIGS. 5 and 6, the flat interfacing and parallel surfaces of hammers 48 and 50 are spaced such that central portion 36 of staple 30 fits closely therebetween and when barbed ends 38 and 40 of the staple become interlocked, the staple will assume a rectangular shape which is smaller than the periphery of rectangular first aperture 18. After blade assembly 44 has traveled its entire distance along axis 55, the lesion will be fully excised from the skin and staple 30 is completely closed. Base assembly 12 may then be removed from the patient's skin, closed staple 30 passing through first aperture 18. Forceps assembly 14, still gripping the excised lesion, may then be withdrawn from hole 20 of housing 16. In FIG. 7, forceps assembly 14 is shown having been completely and separably withdrawn from base assembly 12 with the excised lesion captured between the ends of tweezers 24. The excised lesion may then be discarded or sent to a laboratory for biopsy or other analysis as appropriate.

It is envisioned that after approximately four days the excision wound will have sufficiently healed that staple 30 may be removed. Staple 30 may be removed by cutting it, perhaps at its central portion 36, and peeling its legs 32, 34 away from the skin and withdrawing pins 42 therefrom.

Referring now to FIGS. 9-21, there is shown exciser 100, a second embodiment of the present invention which was prototyped and successfully used in animal experiments.

Exciser 100 comprises first applicator block 102 and second applicator block 104. Disposed between the applicator blocks is blade assembly 106. Guide rods 108 are fixed within bores 110 provided in first applicator block 102 and slidably extend through bores 112 in second applicator block 104. First and second applicator blocks 102 and 104 may be made of a polymeric material such as nylon, for example.

Blade assembly 106 comprises block portion 114 and blade 116. Block portion 114 is made of a material similar to that of applicator blocks 102, 104, and blade 116 is surgical steel or suitable plastic material, like blade 46 of first embodiment exciser 10. Blade 116 is attached to block portion 114 through means of fastener 120 or by any other suitable means. Guide rods 108 slidably extend through bores 118 provided in blade assembly block portion 114.

Figure 10:
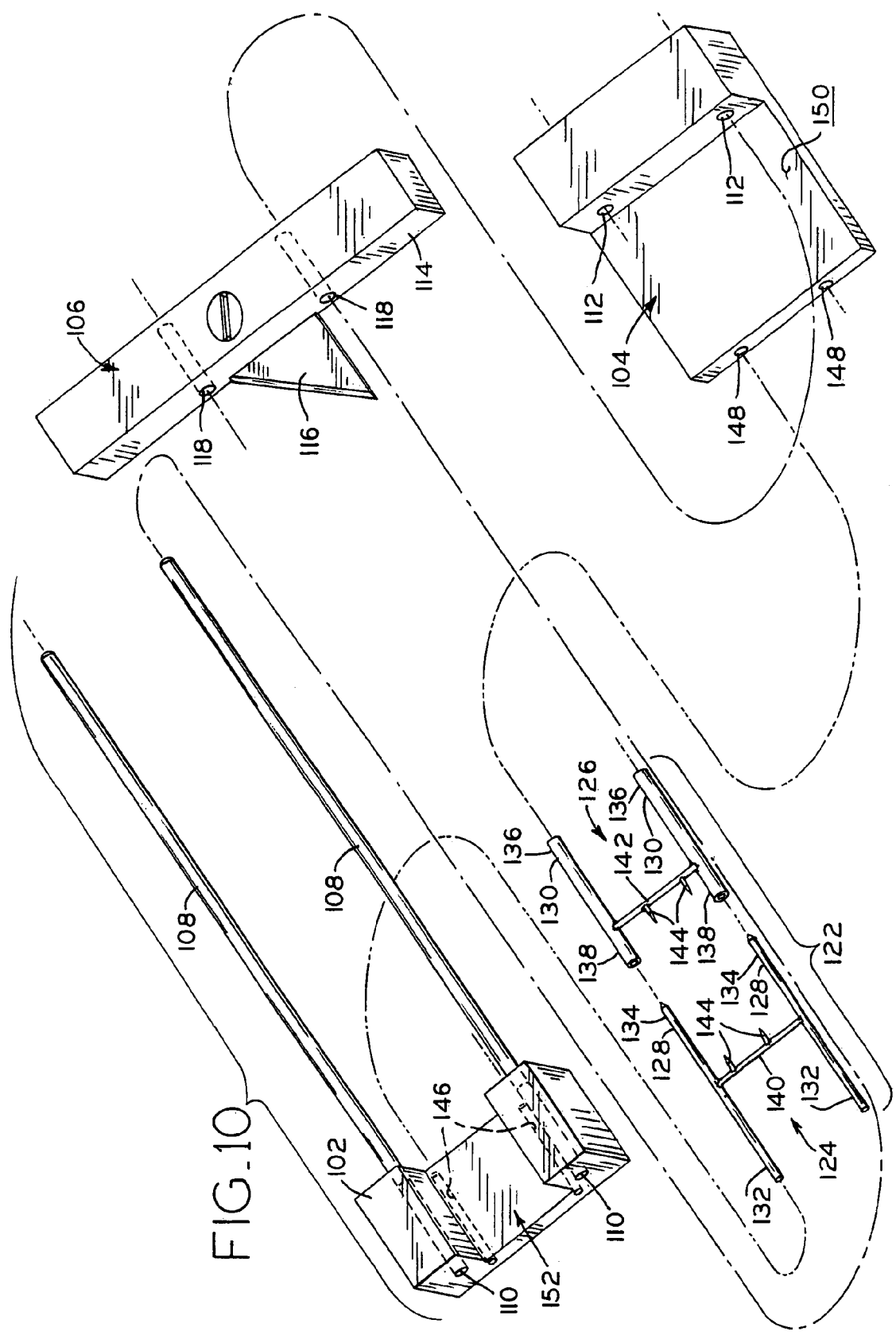
FIG. 10 is a view of the component parts of the device of FIG. 9 in a disassembled state.
Figure 11:
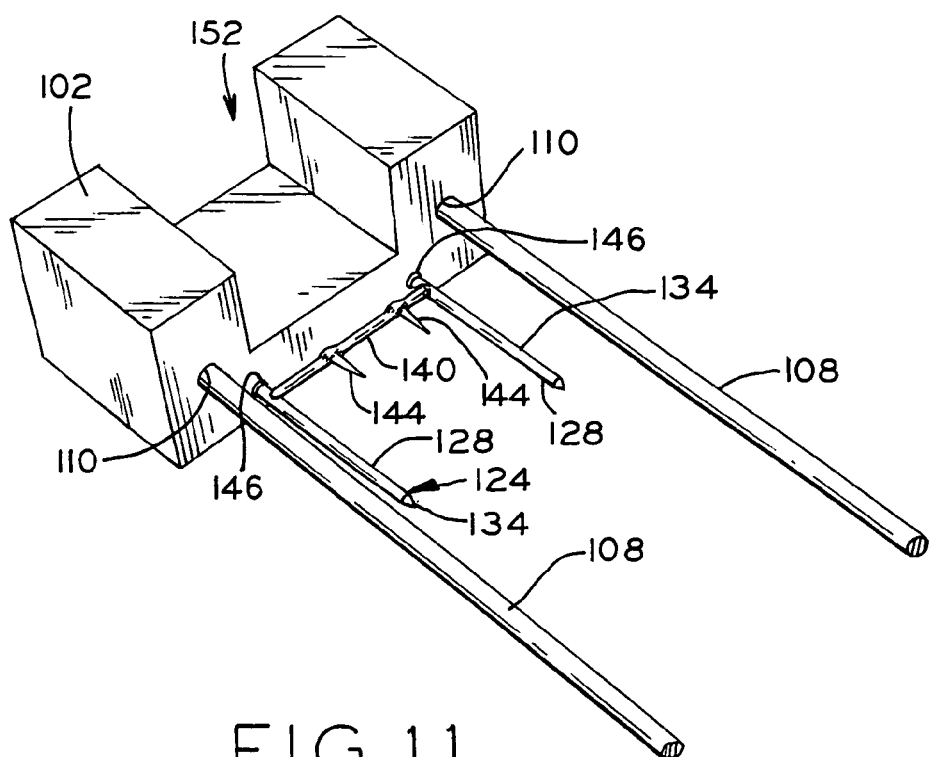
FIG. 11 is an oblique view of the first applicator block of the device of FIG. 9, with the male staple half inserted therein.
Figure 12:
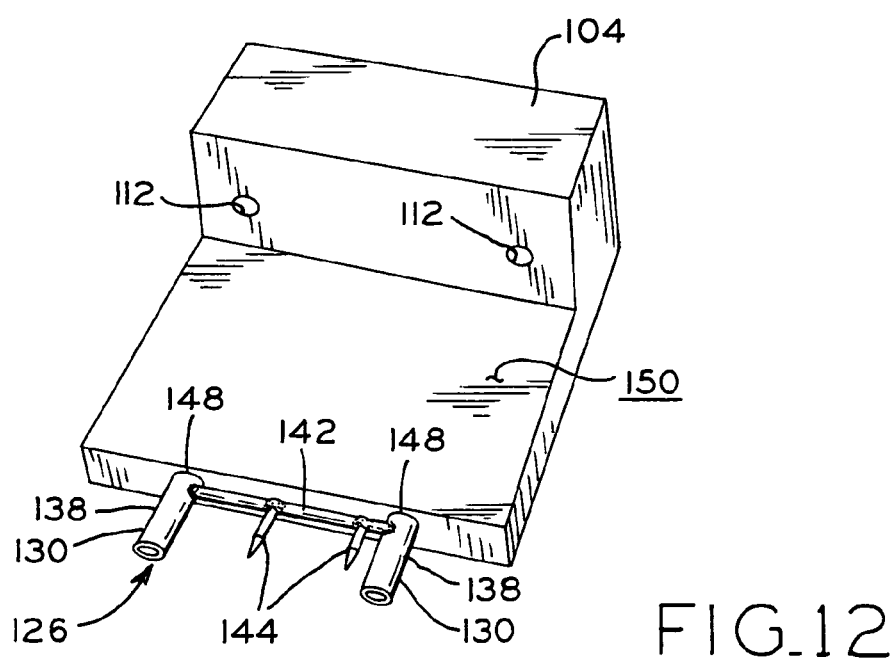
FIG. 12 is an oblique view of the second applicator block of the device of FIG. 9, with the female staple half inserted therein.

The basic components of exciser 100 and its associated skin-closure device are shown in FIG. 10. Two-part staple 122 comprises interfitting male half 124 and female half 126. Male staple half 124 comprises a pair of parallel rod portions 128, and female staple half 126 comprises a pair of similarly spaced parallel tube portions 130. Rod portions 128 each include extending portion 132 and pointed engaging portion 134. Tube portions 130 each include extending portion 136 and engaging portion 138. As further described hereinbelow, each solid engaging portion 134 of the male staple half slidably and interferingly engages its mating hollow engaging portion 138 of female staple half 124 during closure of the staple. When staple halves 124 and 126 are separated or less than fully seated, staple 122 is in its open condition, and when staple halves 124 and 126 are fully engaged, staple 122 is in its closed condition. The interference fit between engaging portions 134 and 138 ensure that staple 122 remains in its closed condition after excision of the lesion.

Figure 15:
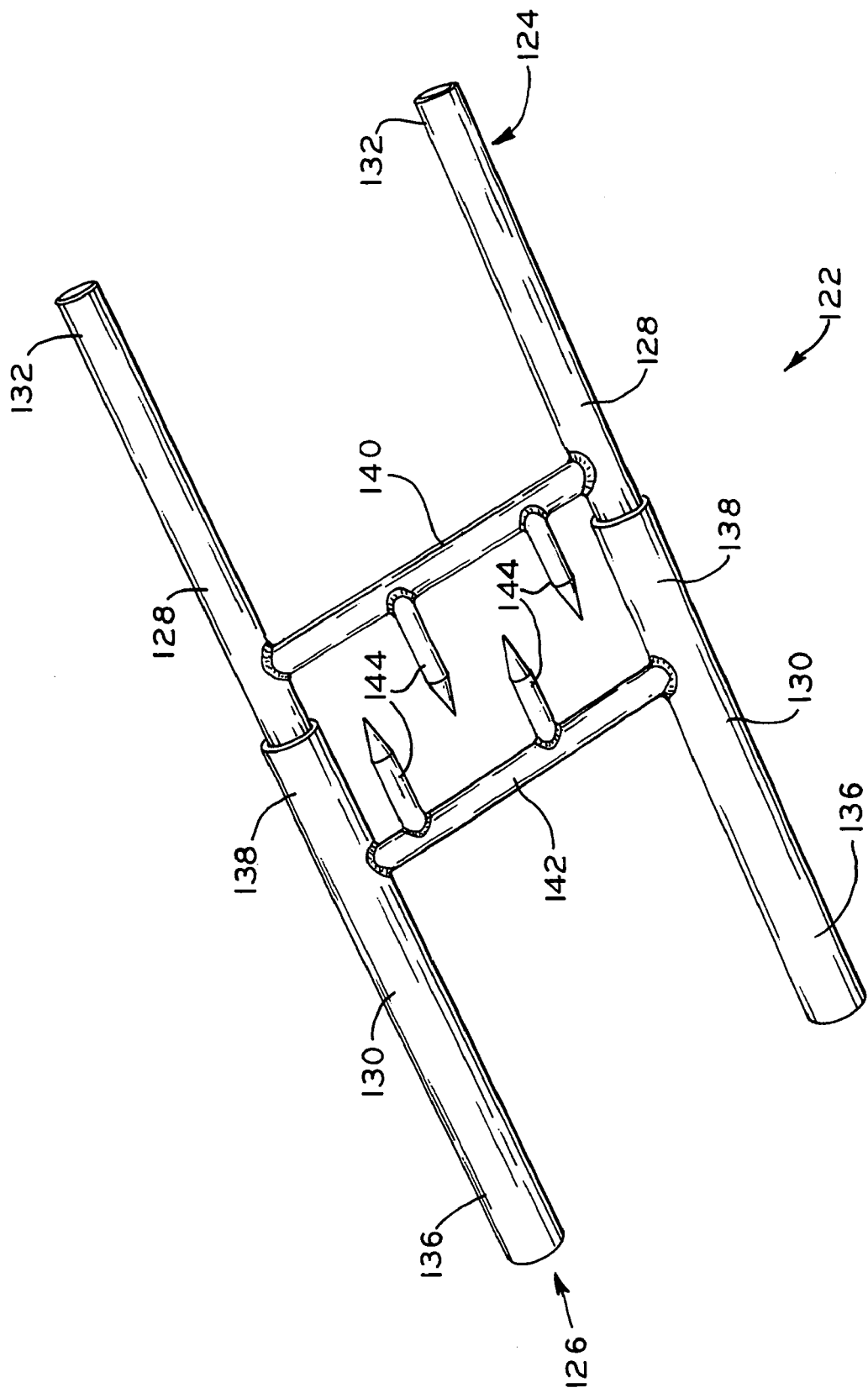
FIG. 15 is a view of the male and female staple halves of FIGS. 11 and 12, respectively, shown interfitted.

Extending between and fixed to rod portions 128 of male staple half 124 is elongate leg 140, and extending between and fixed to tube portions 130 of female staple half 126 is elongate leg 142. When fitted into exciser 100, or when staple 122 is closed, legs 140 and 142 are parallel and extend in directions perpendicular to the longitudinal directions of rod and tube portions 128, 130. Each of legs 140 and 142 is provided with a plurality of sharpened pins 144, which correspond to pins 42 of first embodiment exciser 10 shown in FIGS. 1 through 8. Pins 144 extend in the longitudinal directions of engaging portions 134 and 136 and, when the staple 122 is closed, the pins of the male and female staple halves are misaligned such that they alternate along the legs, and the pointed tips of the pins of one staple half are in close proximity to the leg of the opposite staple half. Notably, when staple 122 is closed as shown in FIG. 15, engaging portions 134 of male staple half 124 extend beyond the engaging portion 138 of female staple half 126 and into the female staple half's tubular extending portions 136. The distance between parallel legs 140 and 142 when staple 122 is closed may be limited by the length of female staple half engaging portion 138 relative to its leg 142, i.e., the ends of engaging portions 136 abut leg 140, thereby minimizing the distance between the staple legs.

Referring again to FIG. 9, it can be seen that prior to excision of lesion L from skin S, extending portions 132, 136 of respective male and female staple halves 124, 126 are received into holes 146, 148 in first and second applicator blocks 102, 104, respectively. That is, holes 146 receive extending portions 132 of male staple half 124, and the male staple half is slid into first applicator block 102 until the interfacing surfaces of the first applicator block and leg 140 abut. Similarly, extending portions 136 of female staple half 126 are slidably received in holes 148 provided in second applicator block 104, with the interfacing surfaces of the second applicator block and leg 142 abutting.

Figure 9:
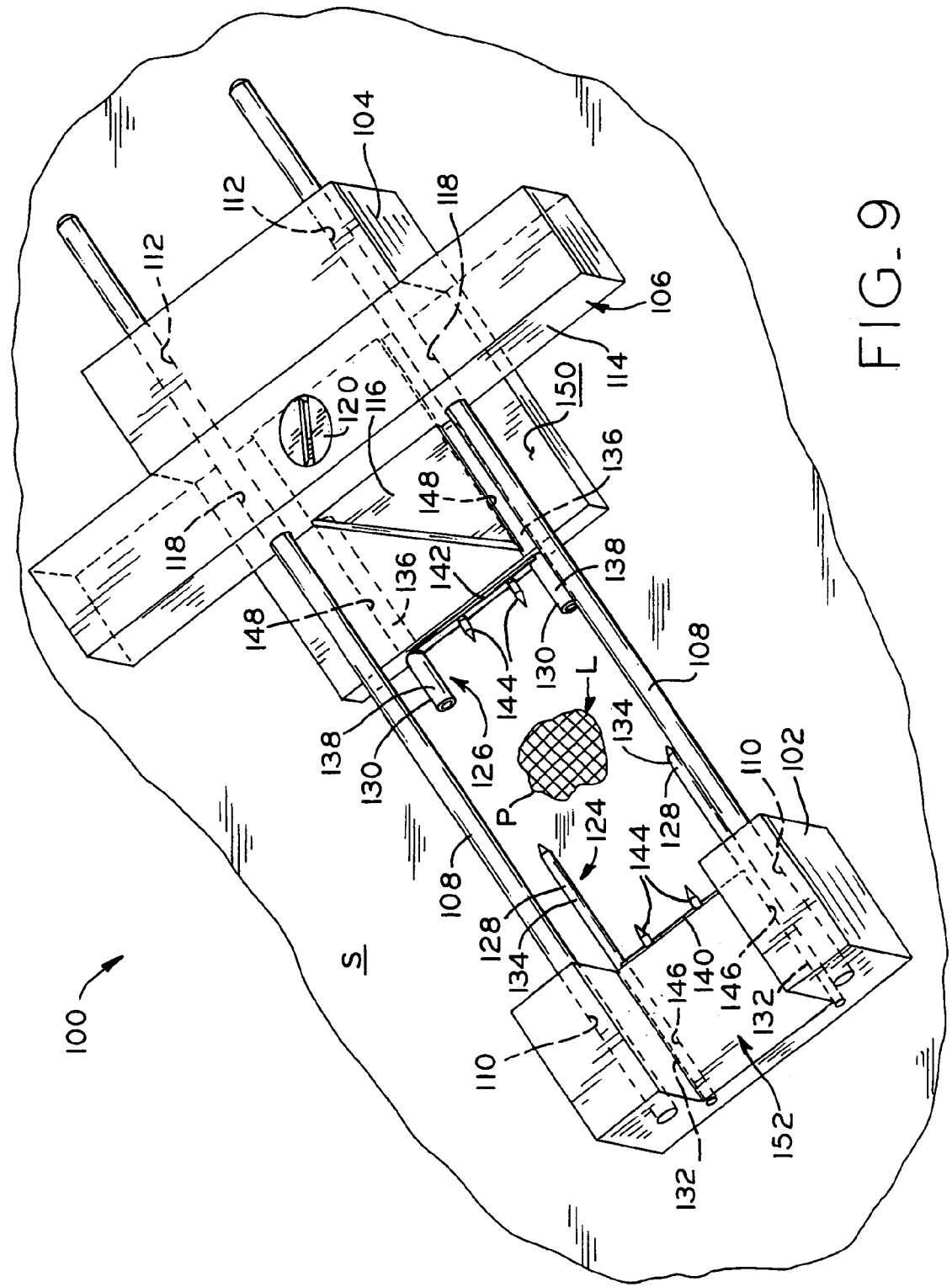
FIG. 9 is an oblique view of a second embodiment of the inventive device located on the skin of the patient, assembled and in a first, open position.
Figure 16:
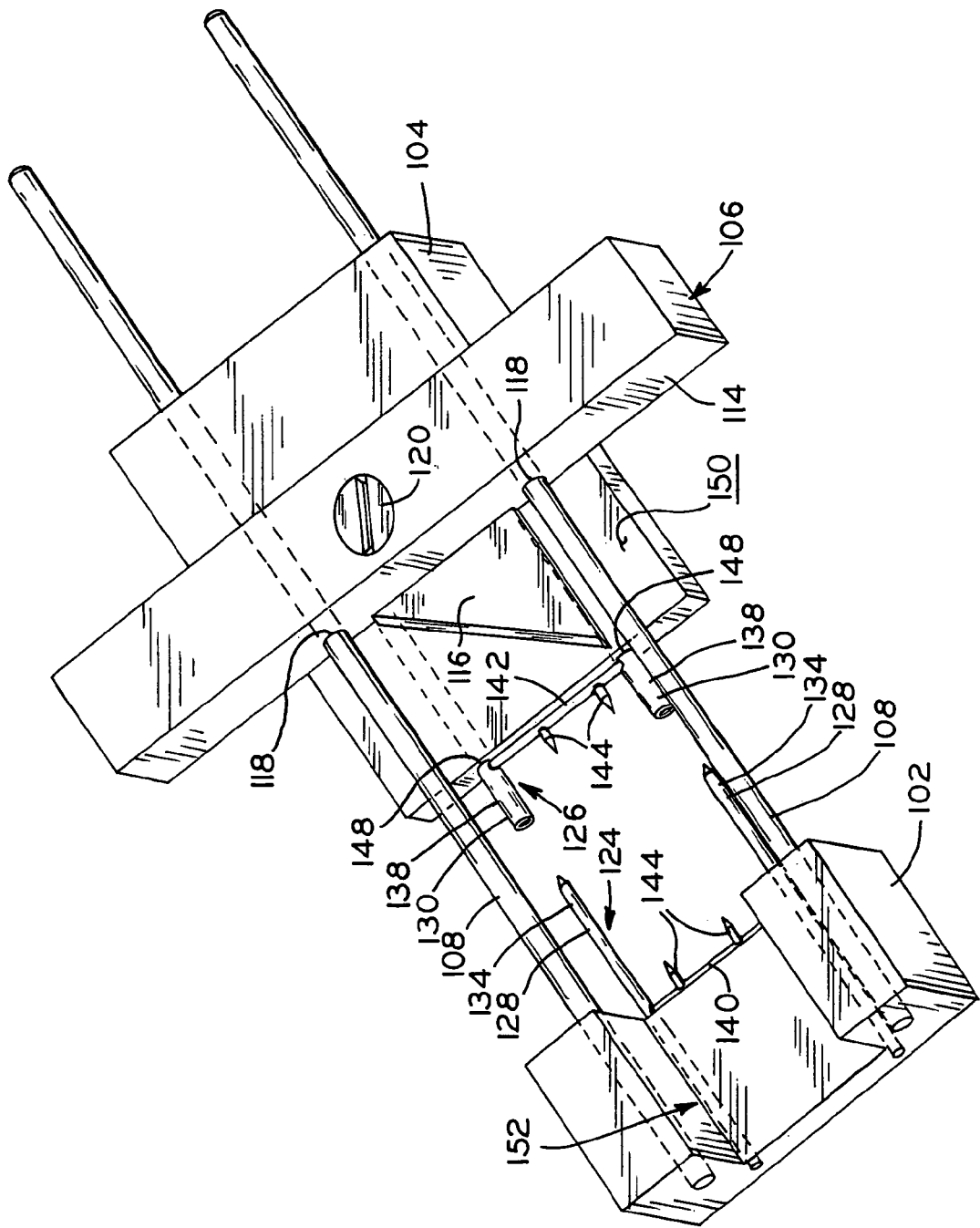
FIG. 16 shows the device of FIG. 9 in a first state, prior to lesion excision.

FIGS. 9 and 16 show exciser 100 loaded with a staple 122 and in its open condition, in which legs 140 and 142 are distant. So configured, exciser 100 is placed onto skin S of the patient. Perimeter P of lesion L to be excised is framed between legs 140 and 142 of the staple and also between the parallel engaging portions 134 of the male staple half 124. Is it again noted that excisers and staples of different sizes may be provided to accommodate the excision various sized lesions and closure of the excision site. During operation of exciser 100, first applicator block 102 is held stationary relative to the patient's skin and second applicator block 104 and blade assembly 106 are moved relative to first applicator block 102 along guide rods 108.

Lesion L to be excised with exciser 100 may be pulled away from skin S through a means of ordinary tweezers or forceps (not shown). Alternatively, the lesion may be captured and pulled away from the skin with a skin hook (not shown). Lesion L is pulled through exciser 100, between the staple legs and the engaging portions of the male staple half, to an extent which places its perimeter P on the side of the plane defined by blade 116 opposite that on which staple 122 is located. This ensures that the entire lesion, and not just a portion thereof, will be excised by blade 116 and the staple will close the skin beneath the excision site by pinching together, between proximate legs 140, 142, only skin located outside of perimeter P. As described above, the sharpened pins of the staple pierce the skin and hold the staple in place on the patient during healing. The excision site is closed by staple 122 into an elliptical shape, and the dermis of the skin, rather than merely the epidermis is brought into and held in abutting contact by the closed staple to promote faster healing.

Referring to FIGS. 16-20, the sequence of movements of exciser 100 and its staple halves are shown sequentially. Prior to the cutting of the skin by blade 116, it can be seen (FIGS. 16-18), that planar blade 116 overlies flat surface 150 of second applicator block 104 and thus cannot begin cutting engagement with the patient's skin until blade assembly 106 is moved relative to second applicator block 104 along guide rods 108.

Figure 17:
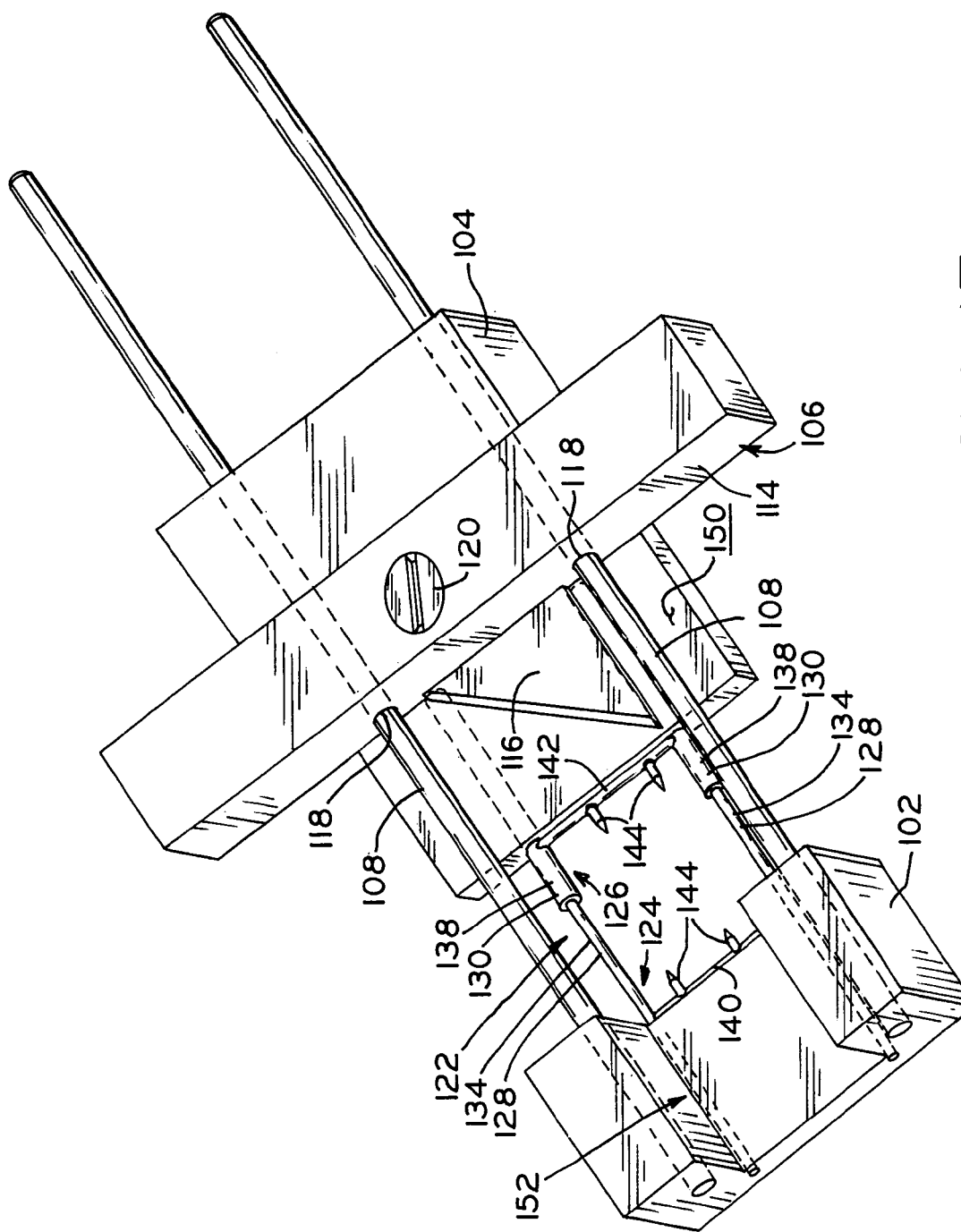
FIG. 17 shows the device of FIG. 9 in a second, sequential state, prior to lesion excision and during interfitting of the staple halves.

FIG. 17 shows the second applicator block 104 and blade assembly 106 having been moved together along guide rods 108 toward first applicator block 102 such that engaging portions 134 and 138 of male and female staple halves 124 and 126 have entered into partial engagement. Thus, it can be seen that closure of staple 122 has begun prior to any cutting by blade 116.

Figure 18:
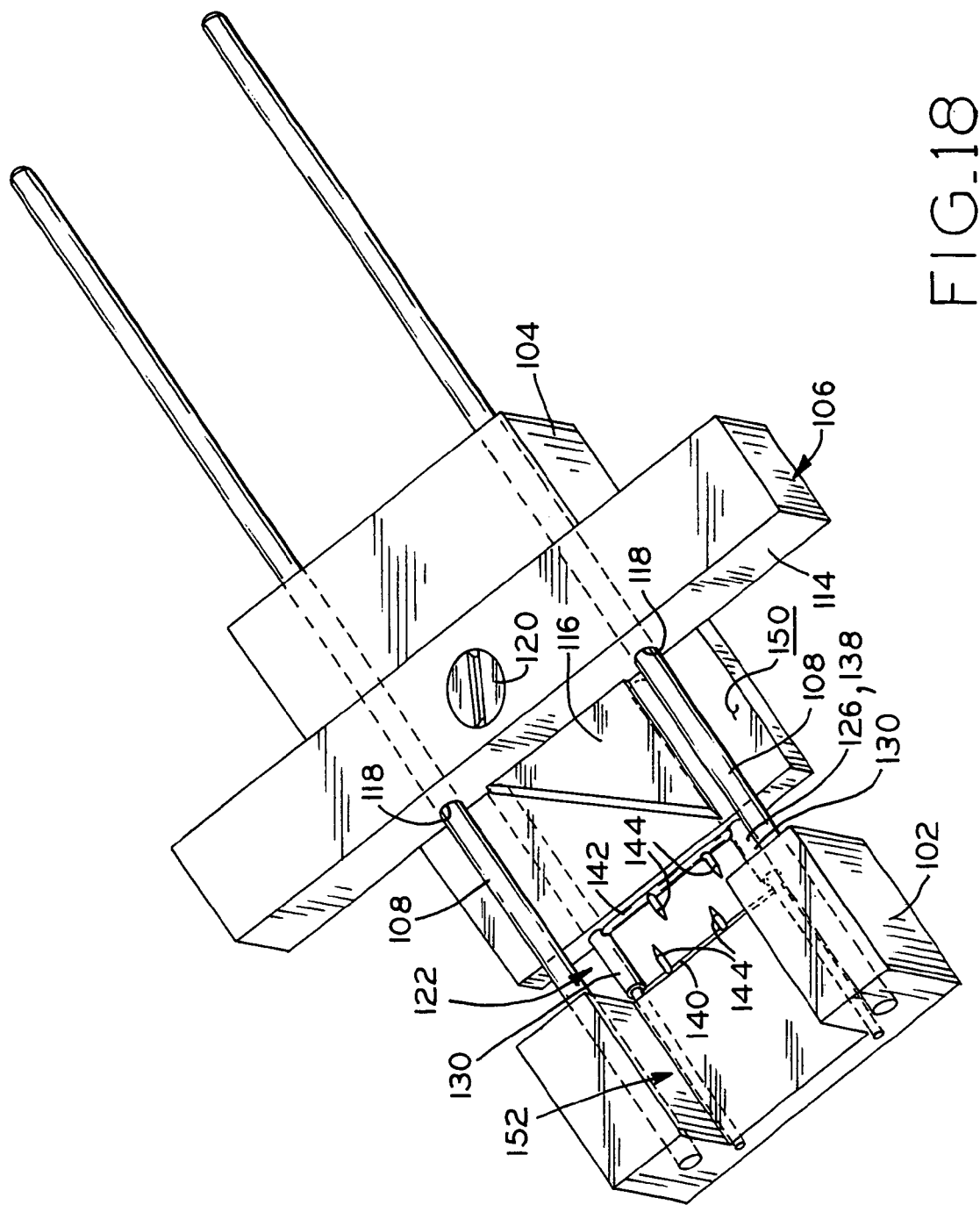
FIG. 18 shows the device of FIG. 9 in a third, sequential state, prior to lesion excision but after closure of the staple.

FIG. 18 shows that further movement of second applicator block 104 and blade assembly 106 together along guide rods 108 toward first applicator block 102 has completely closed staple 122, applicator blocks 102 and 104 being in their closest proximity to each other. Notably, unlike first embodiment exciser 10, in which excision of the lesion and closure of the excision site are done substantially simultaneously, exciser 100 completely closes staple 122 prior to any cutting by blade 116. Lesion L, which had previously been pulled outwardly away from the rest of the patient's skin by ordinary tweezers or forceps, is held in place such that its perimeter P is above the plane defined by flat blade 116 by the staple. Pins 144, which pierce the skin, support the lesion above the plane defined by flat blade 116; but the lesion may still be grasped by the tweezers or forceps for easy handling after excision.

Figure 19:
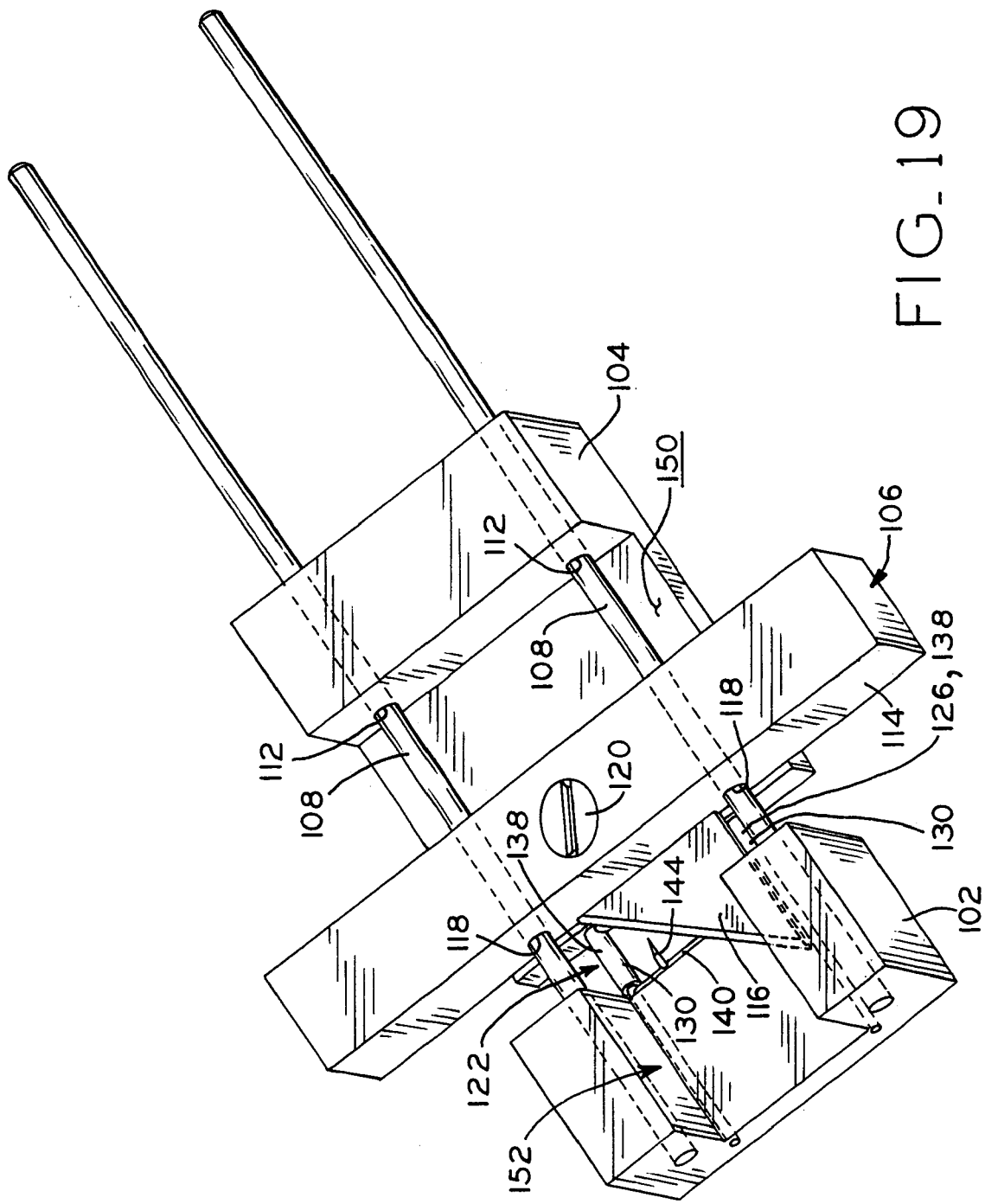
FIG. 19 shows the device of FIG. 9 in a forth, sequential state, during lesion excision.

Referring to FIG. 19, it can be seen that movement of blade assembly 106 relative to second applicator block 104 along guide rods 108 and toward first applicator block 102 forces blade 116 over the closed staple and through the patient's skin, preferably outside of the perimeter of the lesion. Here it can be seen that as blade 116 is moved, it is received in recess 152 formed in first applicator block 102.

Figure 20:
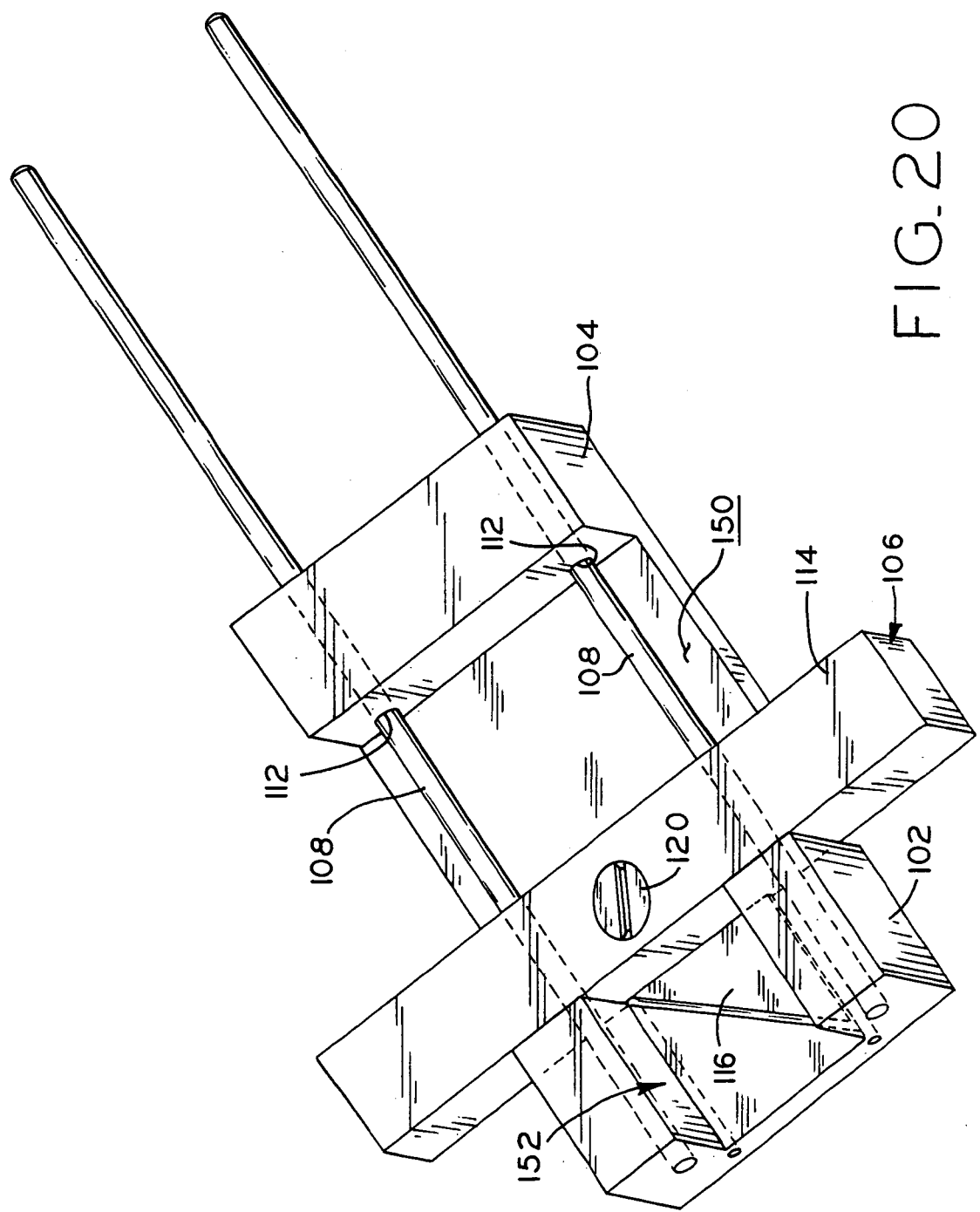
FIG. 20 shows the device of FIG. 9 in a fifth, sequential state, upon lesion excision.

Referring to FIG. 20, exciser 100 is shown in a position in which the lesion has been completely severed and perhaps removed from the excision site by the tweezers or forceps. In this position, the interfacing surfaces of first applicator block 102 and blade assembly block portion 114 abut, and further movement of blade assembly 106 along guide rods 108 away from second applicator block 104 is prevented.

Figure 21:
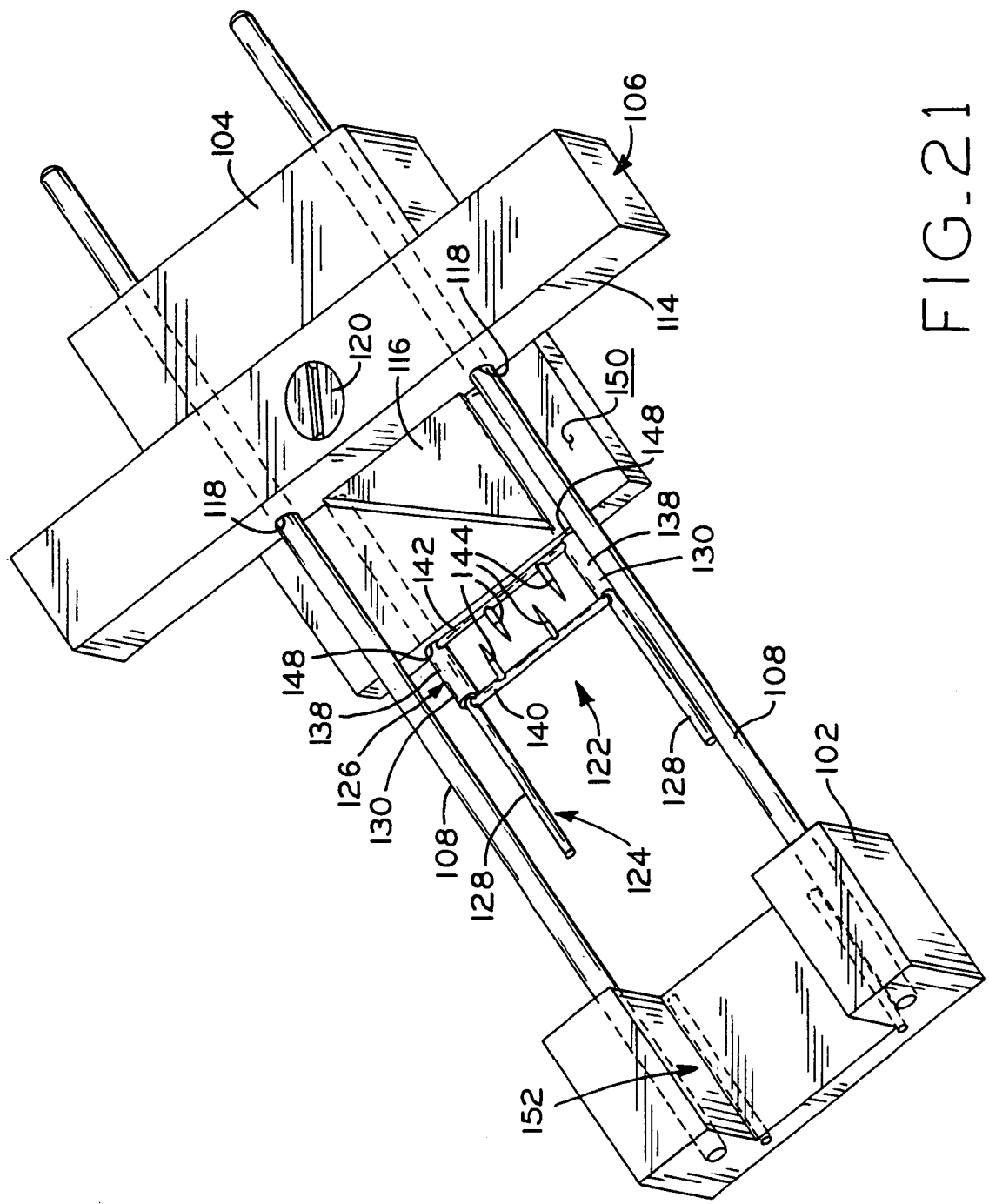
FIG. 21 shows the device of FIG. 9 in a sixth, sequential state, after upon completion of the excision and during partial release of the closed staple from the device.
Figures 22, 23:
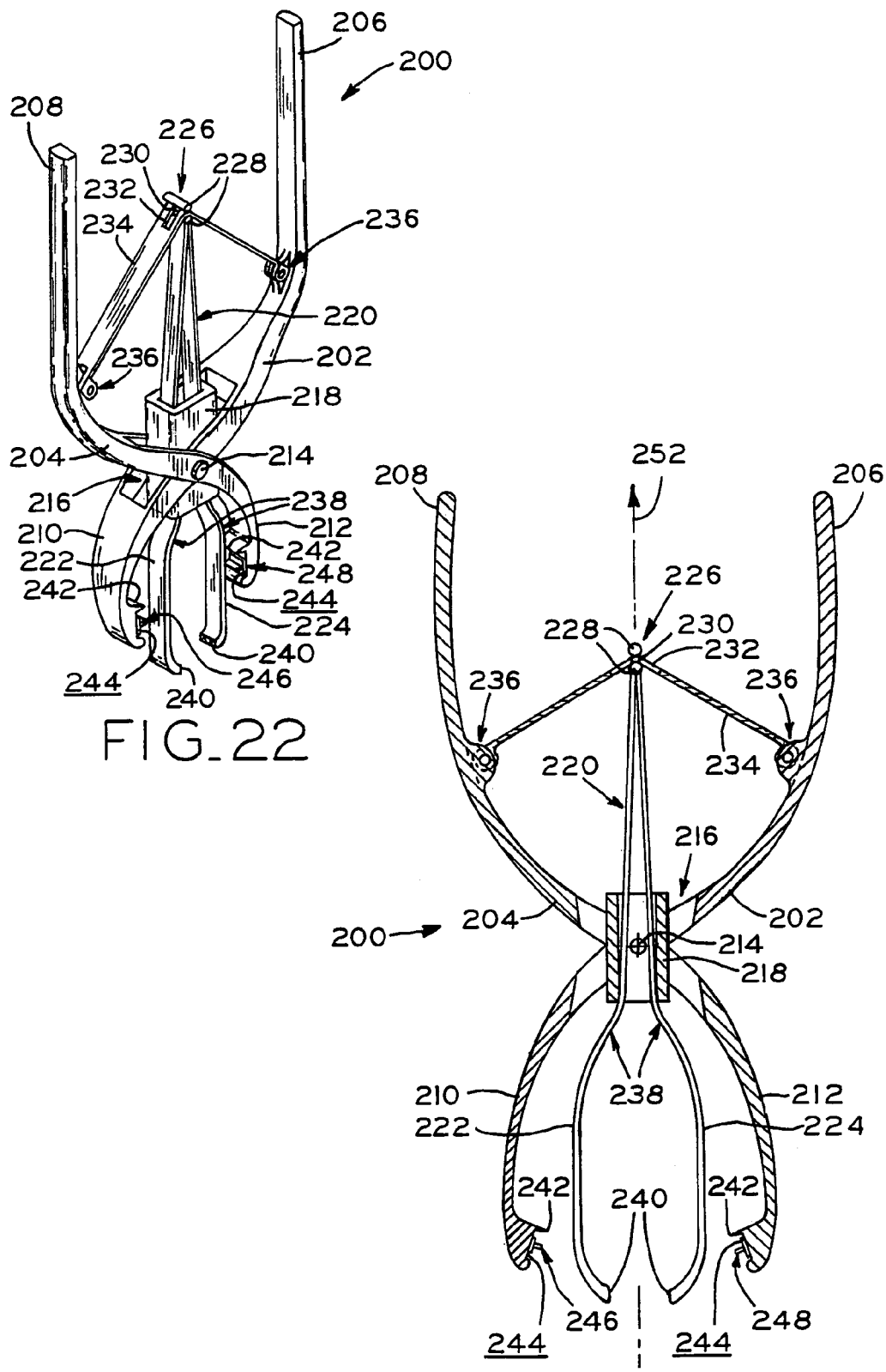
FIG. 22 is an oblique view of a third embodiment of the inventive device.
FIG. 23 is a sectional view of the device of FIG. 22 in a fully opened state.
Figure 24:
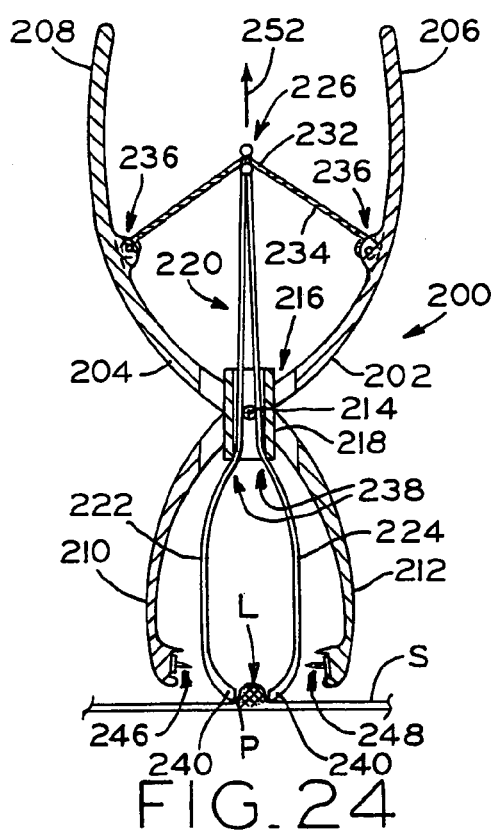
FIG. 24 is a sectional view of the device of FIG. 22 in a first state, prior to lesion excision, the integral tweezers or forceps of the device closed on the lesion to be excised.

Finally, with reference to FIG. 21, blade assembly 106 is reversely slid along guide rods 108 back to its initial position relative to second applicator block 104, and second applicator block 104 and blade assembly 106 are held together. First applicator block 102 is moved away from second applicator block 104 and blade assembly 106, withdrawing guide rods 108 therefrom. Extending portions 132 of staple 122 are withdrawn from holes 146 in first applicator block 102. The position of staple 122 of course remains stationary relative to skin S. Extending portions 136 of staple 122 are then withdrawn from holes 148 in second applicator block 104 and the exciser completely removed from the patient. The extending portions of staple 122 may then be trimmed to reduce the size of the staple. As noted above, it is anticipated that staple 122 would remain in place for approximately four days while the excision site heals, after which the staple halves may be separated by pulling them apart, overcoming the interference fit between the engaging portions 134 and 136. Alternatively, the staple may be cut in any convenient manner such that it may be removed in pieces from the patient.

Referring now to FIGS. 22-27 there is shown exciser 200, a third embodiment of the present invention which is formed of elongate first and second halves 202 and 204, each respectively having a handle portion 206, 208 and a jaw portion 210, 212. First and second halves 202 and 204 are pivotally joined together through rivets 214 to form a basic structure similar to an ordinary pair of pliers or clippers. Formed in first and second halves 202 and 204 is central recess 216, in which is disposed barrel 218. Barrel 218 has the general form of a parallelepiped having closed sides and open ends. Opposite sides of barrel 218 are provided with holes through which rivets 214 extend, thereby securing barrel 218 to the rest of exciser 200. Extending through the open ends of barrel 218 are integral tweezers or forceps 220 comprising first and second flexible arms 222 and 224. Arms 222 and 224 are fixed together at attached end 226 of tweezers 220. Fixed to attached end 226 are short rods 228 which are separated from and attached to each other through neck 230. Rods 228 extend in directions parallel to the longitudinal axes of rivets 214.

Neck 230 extends through slot 232 centrally provided in elongate spring steel strip 234, the opposite ends 236 of which are pivotally attached to first and second exciser halves 202 and 204. Spring steel strip is plastically deformed at its center, and retains and controls longitudinal movement of integral tweezers or forceps 220 through the engagement of rods 228 with the portions of strip 234 on opposite sides of slot 232.

First and second arms 222 and 224 of tweezers 220 are provided with plastically deformed portions 238 which, when tweezers 220 are longitudinally moved in the direction of arrow 252, causes the opposed free ends 240 of first and second arms 222 and 224 to move towards each other and close. As discussed further hereinbelow, the closing action of free ends 240 of integral tweezers or forceps 220 capture the lesion to be excised, and longitudinal movement of tweezers 220 in the direction of arrow 252 pulls the lesion to be excised away from the skin.

Jaw portions 210 and 212 are each provided with opposed blades or cutting edges 242 which, when the jaws are closed, move towards each other and, when the jaws are fully closed, abut each other. Thus, skin located outside perimeter P of lesion L to be excised is pinched between blades 242 and cut from the remainder of the skin thereby. Blades 242, jaw portions 210, 212, halves 202, 204 or indeed entire exciser 200 may be made of surgical stainless steel.

Near the free ends of jaw portions 210 and 212 are located opposed, staple-engaging portions having flat surfaces 244 to which are adhered first and second separate staple halves 246 and 248 which comprise staple 250, another embodiment of a skin-closure device in accordance with the present invention. When staple halves 246 and 248 are separated or at least not fully engaged, staple 250 has an open condition. First and second staple halves 246 and 248 are, and thus staple 250 is, closed through manipulation of exciser 220 which interlocks the staple halves to each other. With the staple halves in this fully engaged state, the staple has a closed condition.

The operation of exciser 200 is now discussed with reference to FIGS. 24-27. In a first state shown in FIG. 24, free ends 240 of the integral tweezers or forceps capture lesion L to be excised from skin S, and the lesion is pinched therebetween as handle portions 206 and 208 are closed towards each other slightly.

Figure 25:
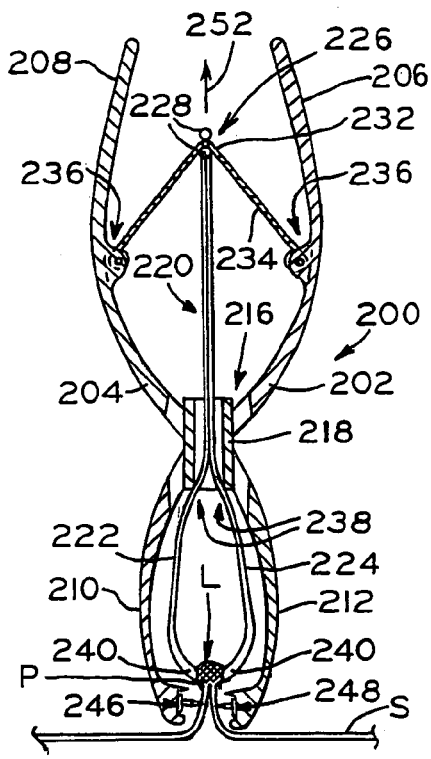
FIG. 25 shows the device of FIG. 22 in a second, sequential state, prior to lesion excision and during closure of the staple halves through the skin surrounding the lesion.

In a second, sequential state shown in FIG. 25, further movement of handle portions 206 and 208 towards each other causes spring steel strip 234 to flex and its center to move in the direction of arrow 252, which forces tweezers 220 in that direction. Movement tweezers 220 upward in the direction of arrow 252 brings deformed portions 238 of first and second arm 222 and 224 into sliding engagement with the opening of barrel 218 and forces free ends 240 of the first and second arms 222 and 224 closer together, pinching lesion L as it is pulled away from skin S. After tweezer free ends 240, and lesion L therebetween, have moved to a position within the jaws formed by portions 210 and 212 such that lesion perimeter P is past blades 242, staple halves 246 and 248 enter engagement with the skin outside of perimeter P and with each other in the manner disclosed further hereinbelow.

Figure 26:
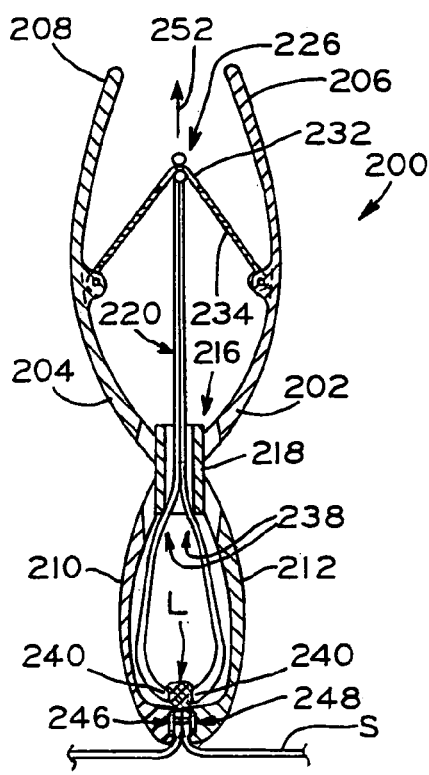
FIG. 26 shows the device of FIG. 22 in a third, sequential state, subsequent to closure of the staple and during lesion excision.

In a third sequential state shown in FIG. 26, handle portions 206 and 208 have been brought further together, and tweezers have moved further in the direction of arrow 252. In this state, staple 250 is fully closed, and blades 242 are brought into abutting engagement with each other, severing lesion L from skin S below lesion perimeter P. Although staple 250 may achieve its fully closed condition prior to actual engagement of blades 242 with skin S, the closing of the staple and the excision of lesion L may alternatively occur substantially simultaneously.

Figure 27:
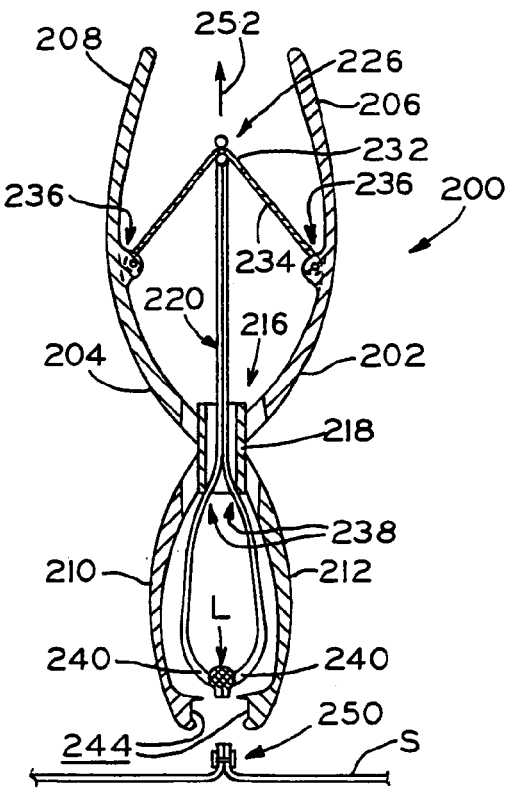
FIG. 27 shows the device of FIG. 22 in a fourth, sequential state, subsequent to lesion excision and during removal of the excised lesion from the skin.
Figure 28:
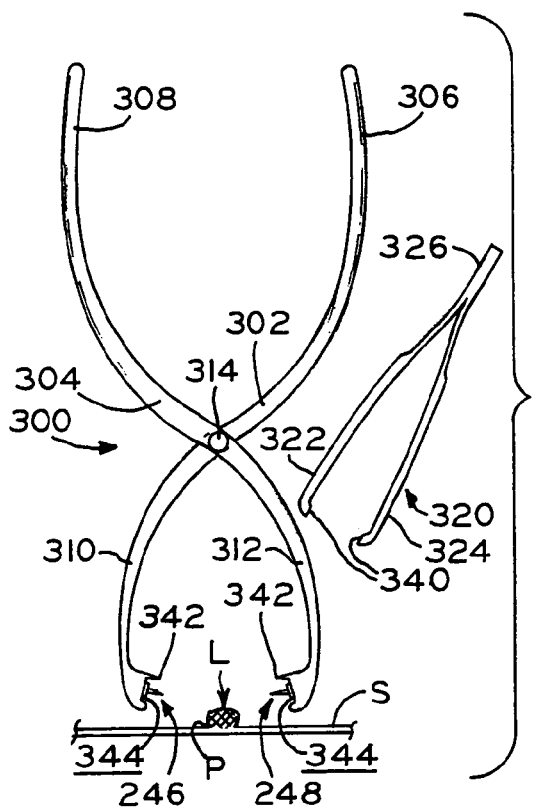
FIG. 28 is a side view of a fourth embodiment of the inventive device in a fully opened state, with separate, known tweezers or forceps also shown.

In a fourth sequential state shown in FIG. 27, exciser 200, with excised lesion L still captured between tweezer free ends 240, is removed from the patient, staple 250 having closed skin S below the excision site such that the dermis located on opposite sides of the excision site are in abutting contact and an elliptically-shaped closure wound is formed as described above. The adhesive, which holds staple halves 246 and 248 to their respective flat surfaces 244 of the staple-engaging portions at the free ends of the exciser jaws, breaks free upon slight release of handle portions 206, 208 which are urged away from each other by spring steel strip 232, and exciser 200 can then be freely removed, leaving staple 250 behind. As handle portions 206, 208 are more fully released, tweezers 220 move in a direction opposite to arrow 252, allowing free ends 240 to separate, freeing excised lesion L.

Referring now to FIGS. 28-31 there is shown exciser 300, a fourth embodiment of a device according to the present invention, in a series of sequential states of operation. Exciser 300, like exciser 200 has a basic structure similar to that of an ordinary pair of pliers or clippers, and a common skin-closure device may be used with these exciser embodiments.

Exciser 300 has a pair of elongate first and second halves 302 and 304, each respectively having handle portion 306, 308 and jaw portion 310, 312, halves 302 and 304 being pivotally joined together by pin 314. Rather than being provided with integral tweezers or forceps, as exciser 200 is, exciser 300 is used with separate, known tweezers or forceps 320 as shown. Tweezers 320 are used to capture and pull lesion L away from the skin S of the patient prior to moving handle portions 306 and 308 towards each other to close the skin closure device or staple, and excise lesion L. Alternatively, the lesion may be captured and pulled with a skin hook (not shown). Except for these differences, the structure and operation of exciser 300 are substantially identical to those of exciser 200.

Figure 29:
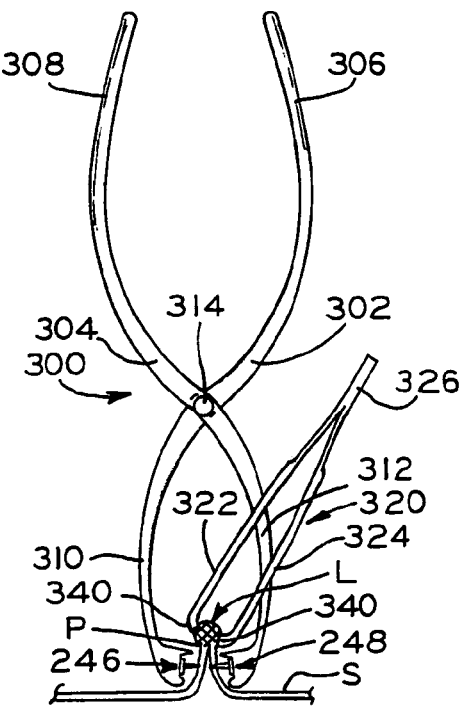
FIG. 29 shows the separate tweezers pulling the lesion away from the skin and the device of FIG. 28 in a second, sequential state, prior to lesion excision and during closure of the staple halves through the skin surrounding the lesion.

Exemplary tweezers 320 have first and second arms 322 and 324 joined at attached end 326. With the ends of jaw portions 310, 312 placed against skin S and lesion L placed loosely therebetween, tweezer free ends 340, which may be serrated, grasp lesion L which is then pulled away from skin S of the patient and into the jaws of exciser 300. Once the captured lesion has been pulled into jaw portions 310 and 312 to an extent that lesion perimeter P is above blades 342, handle portions 306 and 308 are squeezed further together, and staple halves 246 and 248 which comprise staple 250 are brought into engagement with the skin outside the outer perimeter of the lesion L and with each other, as shown in FIG. 29.

Figure 30:
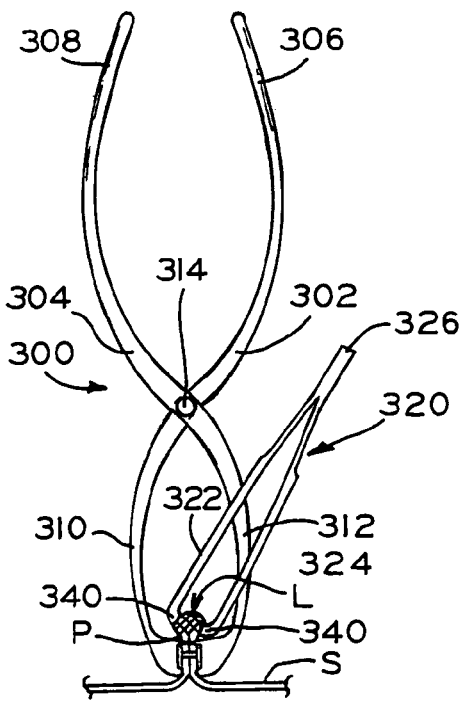
FIG. 30 shows the device of FIG. 28 in a third, sequential state, after closure of the staple and during lesion excision.
Figure 31:
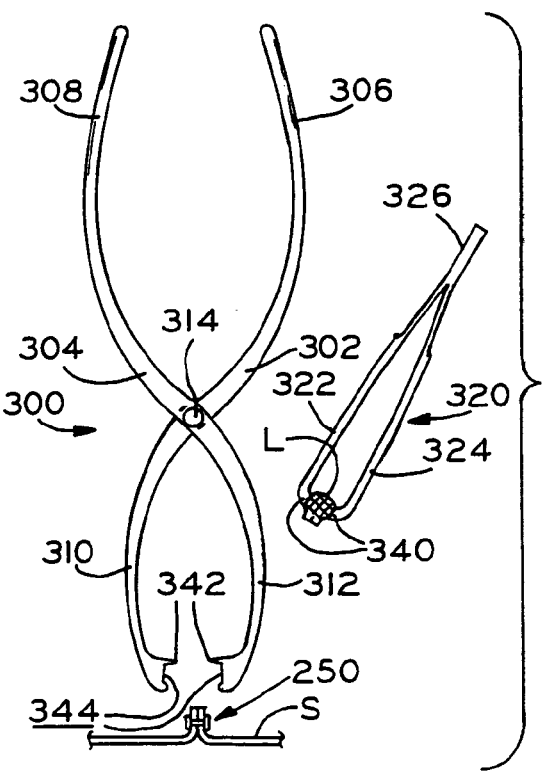
FIG. 31 shows the device of FIG. 28 in a fourth, sequential state, subsequent to lesion excision and during removal of the excised lesion from the skin with the tweezers.

In FIG. 30, staple 250 is fully closed on skin S and blades 342 sever lesion L from skin S at a location outside lesion perimeter P, as described above. As noted above, although staple 250 may achieve its fully closed condition prior to actual engagement of blades 342 with skin S, the closing of the staple and the excision of lesion L may alternatively occur substantially simultaneously. The lesion held by tweezers 320 is then removed from the excision site. In FIG. 31, the jaws of exciser 300 are separated, causing the adhesive, which held staple halves 246, 248 to flat surfaces 344 of the staple-engaging portions of the jaws, to break free. The resulting elliptically-shaped excision wound, in which the dermis located on opposite sides of the excision is held in abutting contact by staple 250, is substantially identical to that resulting from use of exciser 200.

Figure 32:
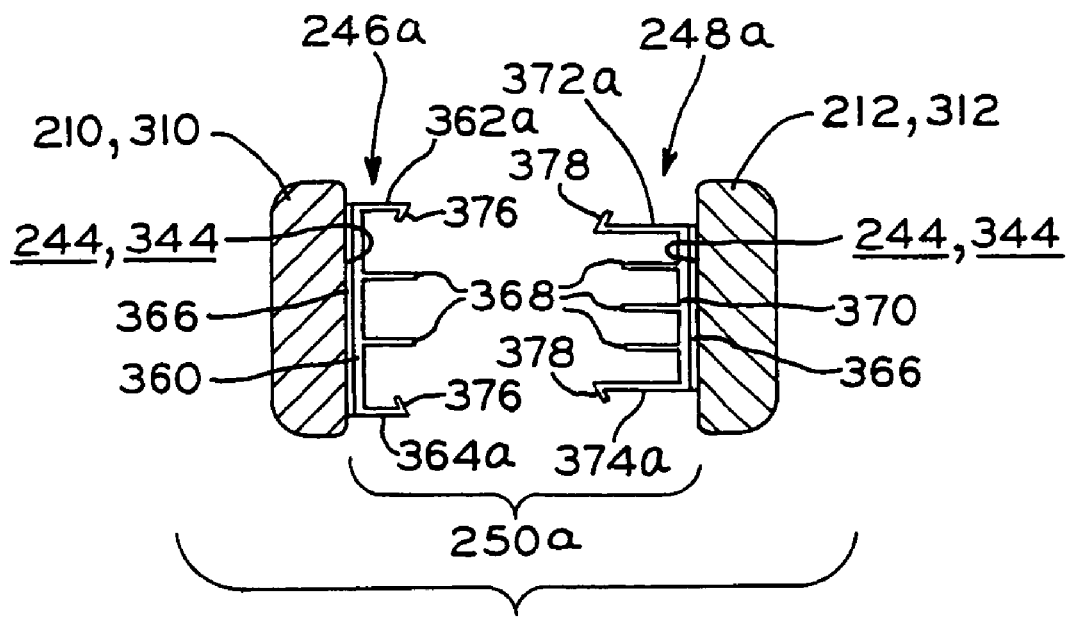
FIG. 32 is a disassembled view of a first embodiment of a two-piece staple for use with the inventive device of FIG. 22 or 28, the staple pieces shown attached thereto.
Figure 33:
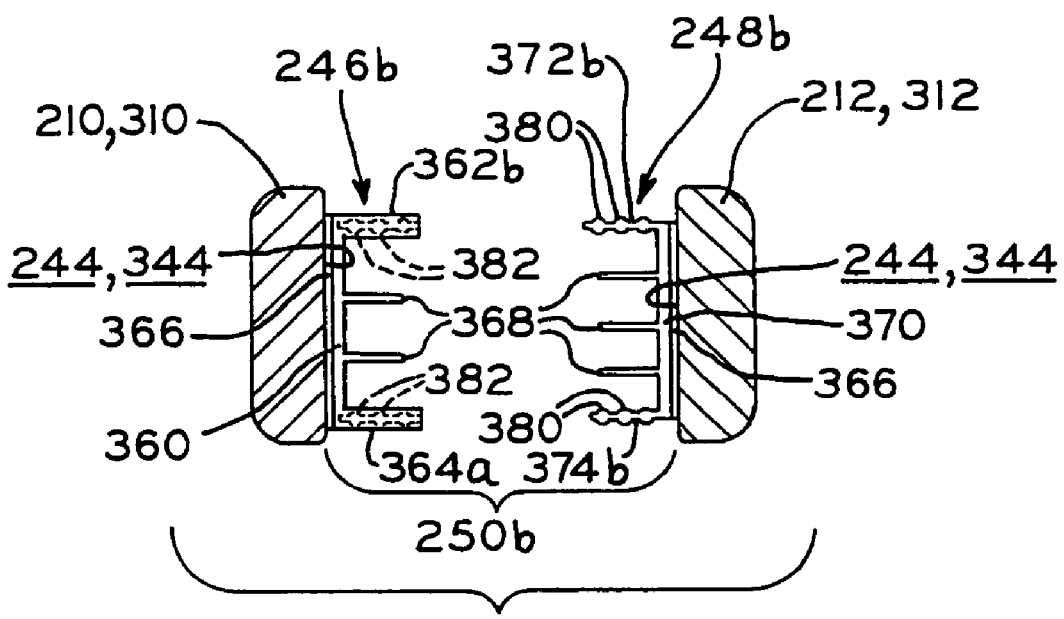
FIG. 33 is a disassembled view of a second embodiment of a two-piece staple for use with the inventive device of FIG. 22 or 28, the staple pieces shown attached thereto.

Referring now to FIGS. 32 and 33, there are respectively shown staples 250a and 250b, first and second embodiments of staple 250 which can be used with either of above-described excisers 200 and 300. Identical elements of staples 250a and 250b are identified with a common reference numeral, whereas corresponding elements of staples 250a and 250b are identified alphanumerically with a common numeric portion an alphabetic character (a or b) which correlates with a particular embodiment staple 250a or 250b. Each embodiment of staple 250 comprises staple halves 246 and 248 which, in the figure, are respectively shown adhered to flat surfaces 244,344 of jaw portions 210, 310 and 212, 312 of excisers 200, 300. Those skilled in the art will recognize that this association between staple halves and jaw flat surfaces may be reversed. Staple halves 246, 248 may be made of surgical stainless steel or a suitable plastic material.

Each staple half 246 is provided with elongate flat central portion 360 extending between legs 362 and 364. A suitable releasable adhesive 366, which is later broken free during removal of the exciser from the patient as described above, is provided between the outer planar surface of flat central portion 360 and the abutting surface 244, 344 of jaw portion 210,310.

Similarly, each staple half 248 is provided with elongate flat central portion 370 extending between legs 372 and 374, staple half 248 being releasably adhered to its mating jaw surface 244, 344 by adhesive 366.

Pointed pins 368 extend from the inner planar sides of flat central portions 360, 370, and when staple 250 is closed, the terminal ends of pins 368 of one staple half abut the interfacing inner surface of the other staple half. Further, with staple 250 closed, the pins alternate along the staple length on the basis of which staple half they extend from. Moreover, each staple half 246, 248 is substantially symmetrical about the center of its central portion 360,370, thereby allowing the staple halves to each be oriented on flat surfaces 244,344 in either of two orientations 180 degrees apart; i.e., the locations of legs 362 and 364 of staple half 246, or the locations of legs 372 and 374 of staple half 248 may be switched relative to the exciser.

Referring to FIG. 32, the ends of legs 362a and 364a are provided with barbs 376 which, when staple 250a is closed, are interconnected with barbs 378 provided at the ends of legs 372a and 374a, the interconnecting barbs holding staple 250a in its closed condition. The interconnection of barbs 376 and 378 occurs as they slide past each other, resiliently deflecting at least one leg of each interconnecting pair, and become hooked to each other.

Referring to FIG. 33, the legs 362b and 364b are substantially tubular and telescopically engage legs 372b and 374b, which are interference fitted therein during closure of staple 250b to maintain its closed condition. The engaging surfaces of legs 362b, 364b and 372b, 374b may be smooth, their sliding interference fit being substantially as disclosed above with respect to rod portions 128 and tube portions 130 of staple 122 of second embodiment exciser 100 (see FIG. 15).

Staple halves 246b, 248b which are made of plastic may alternatively have its legs 372b, 374b provided with ribs 380, as shown in FIG. 33, which are compressed as they are forced into smooth-walled hollow legs 362b, 364b, the compression of ribs 380 providing a secure interference fit between the interconnected legs. As shown in FIG. 33, the interior surfaces of hollow legs 362b and 364b may be also provided with recesses 382 into which ribs 380 are received as legs 372b, 374b are forced therein, the interfitting engagement of ribs 380 and recesses 382 holding staple 250b in its closed condition.

FIGS. 34a-34d schematically illustrate a sectional view a device 410 constructed in accordance with a fifth embodiment of the present invention. The device 410 may be used for excising tissue and closing a wound that results from excision of the tissue. FIGS. 34a-34d schematically illustrate the device 410 excising a lesion 412 from skin 414.

The device 410 includes a housing 418. An aperture 420 extends vertically through the housing 418. The device 410 also includes a cutting member 422 and a clamping member 424. At least one actuator 426 is movable relative to the housing 418 for moving the cutting member 422 and for closing the closure member 424. An optional second actuator that cooperates with the actuator 426 for closing the closure member 424 is shown by dashed lines at 428 in FIGS. 34a-34d.

Figure 34A:
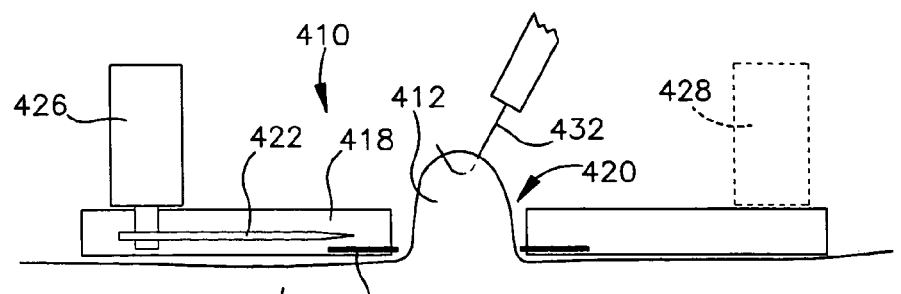
FIGS. 34a-34d schematically illustrate a sectional view a device constructed in accordance with a fifth embodiment of the present invention.

To remove the lesion 412 from the skin 414, the housing 418 is positioned relative to the skin 414 so that the lesion 412 is located directly below the aperture 420. As is shown in FIG. 34a, the lesion 412 is pulled through the aperture 420 of the housing 418 using a skin hook 432 or other suitable device for grabbing the lesion 412. When the lesion 412 is pulled through the aperture 420, the skin 414 adjacent the lesion 412 is tensioned.

Figure 34B:
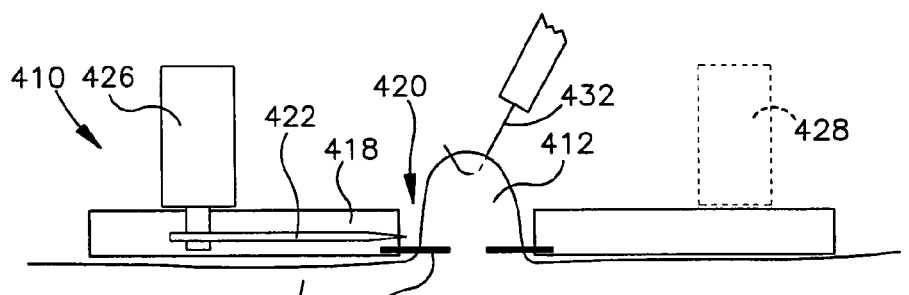

Next, as is shown in FIG. 34b, the actuator 426 of the device 410 is moved relative to the housing 418. Movement of the actuator 426 causes the closure member 424 to begin to close. As the closure member 424 begins to close, tines (not shown) of the closure member 424 pierce the tensioned skin 414 and the closure member begins to pinch the skin adjacent the lesion 412.

Figure 34C:
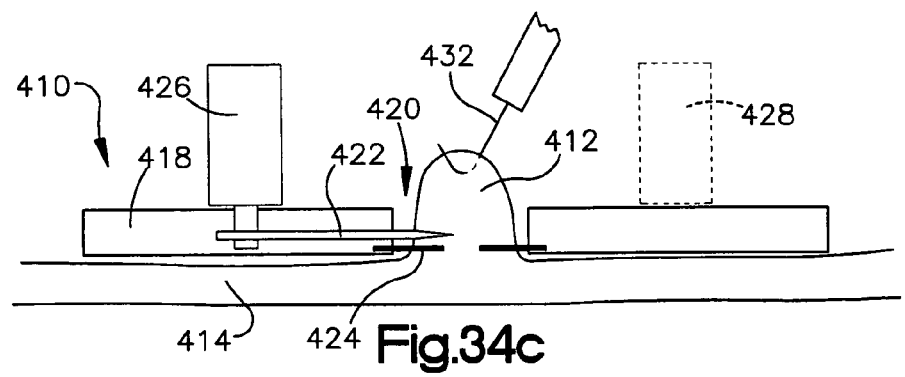
Figure 34D:
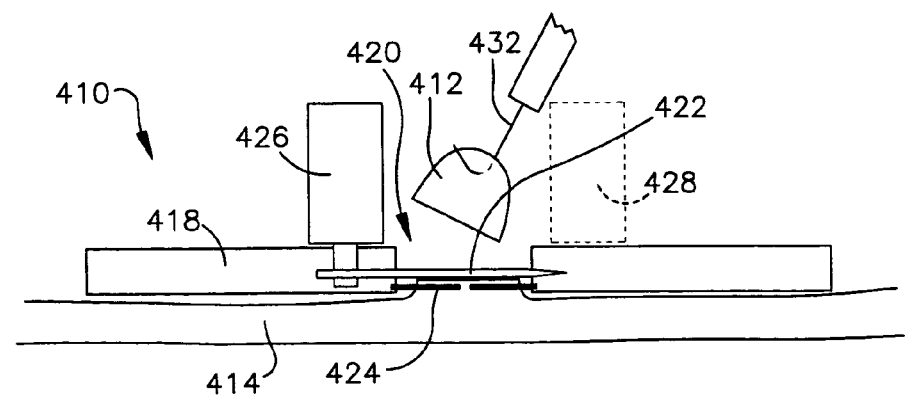

As shown in FIG. 34c, further movement of the actuator 426 relative to the housing 418 causes the cutting member 422 to begin excising the lesion 412 from the skin 414. When the lesion 412 is completely removed from the skin 414, as shown in FIG. 34d, further movement of the actuator 426 closes the closure member 424 to close a wound that results from excision of the lesion 412. Alternatively, the closure member 424 may be closed prior to the cutting member 422 completely removing the lesion 412 from the skin 414. The following description with reference to FIGS. 35-48 will describe two devices constructed in accordance with the fifth embodiment of the present invention.

Figure 35:
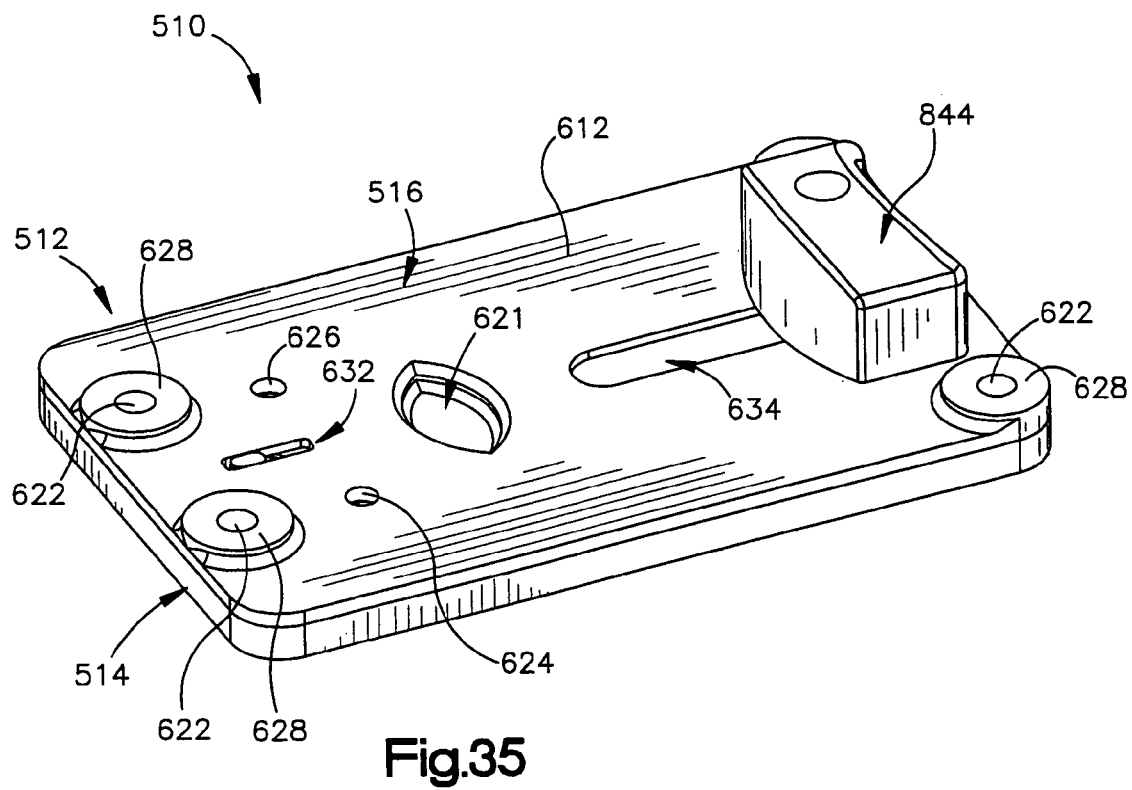
FIG. 35 is an oblique view of a first exemplary device constructed in accordance with the fifth embodiment of the present invention.
Figure 36:
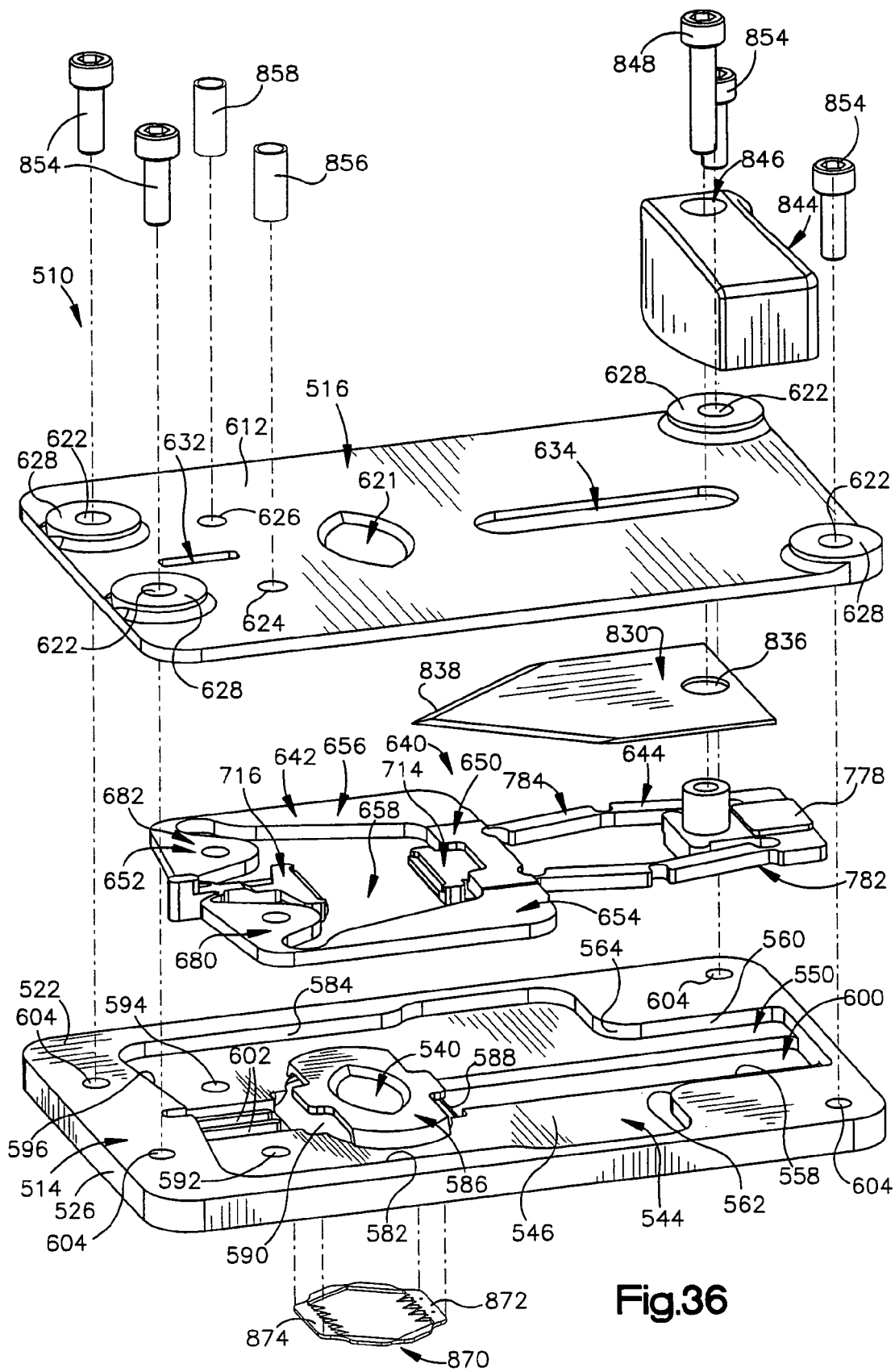
FIG. 36 is an oblique, exploded view of the device of FIG. 35.
Figure 37:
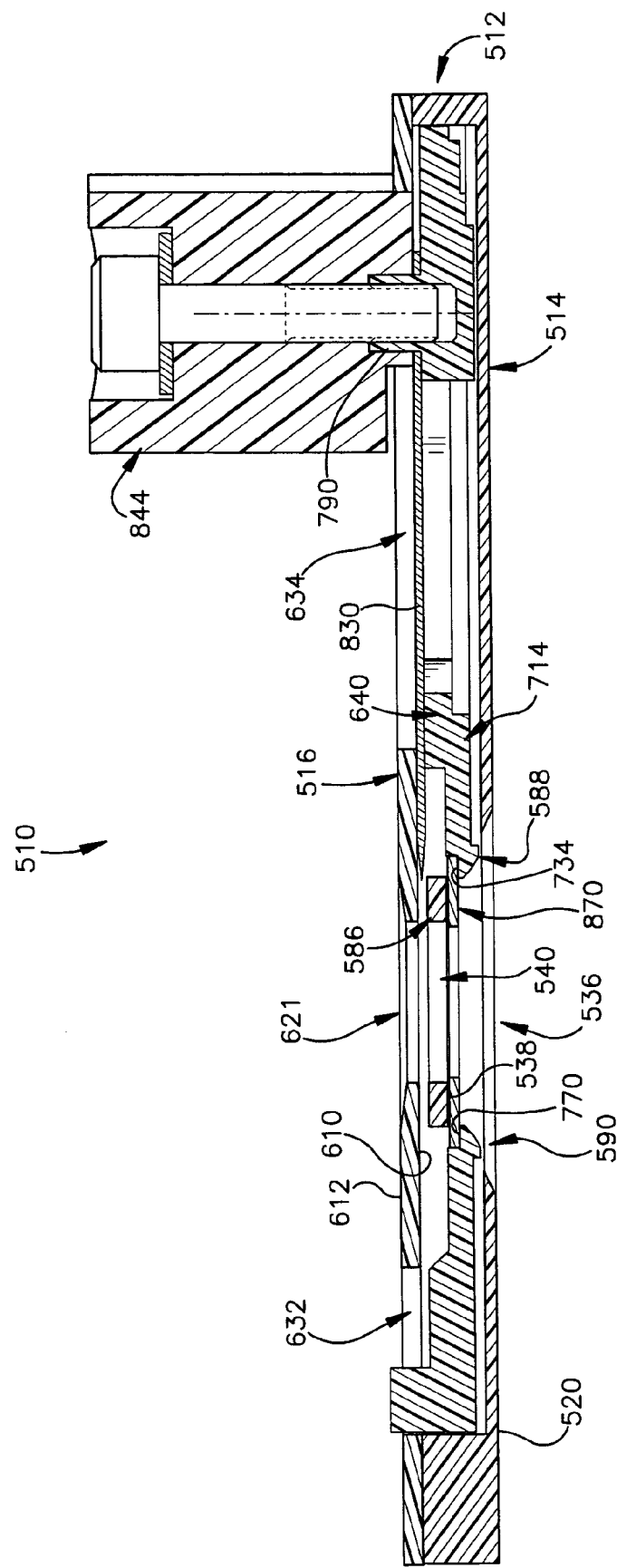
FIG. 37 is a sectional view of the device of FIG. 35.

FIG. 35 is an oblique view of a first exemplary device 510 constructed in accordance with the fifth embodiment of the present invention. FIG. 36 is an exploded oblique view of the device 510 and FIG. 37 is a sectional view of the device 510. The device 510 includes a housing 512 having a base plate portion 514 and a top plate portion 516.

The base plate portion 514 of the housing 512 includes lower and upper surfaces 520 and 522, respectively. As best shown in FIG. 37, a cavity 536 extends upwardly into the lower surface 520 of the base plate portion 514. The cavity 536 is generally elliptical and terminates at an upper surface 538 (FIG. 37). An elliptical aperture 540 extends through the base plate portion 514 and into the cavity 536.

As best shown in FIG. 36, a first recess 544 extends downwardly into the upper surface 522 of the base plate portion 514. As will be described in detail below, the first recess 544 receives a driver 640 of the device 510. The first recess 544 includes a generally planar bottom surface 546.

The first recess 544 includes a narrow section having laterally opposite side surfaces 558 and 560. Comers 562 and 564, which preferably have equal radii, form transitions between the laterally opposite side surfaces 558 and 560 and a wider section of the first recess 544. As will be discussed below, the location of the comers 562 and 564 determines a timing for cutting the lesion and clamping the skin adjacent the lesion.

As shown in FIG. 36, another section of the first recess 544 is located between laterally opposite side surfaces 582 and 584. A protruding portion 586 that includes the elliptical aperture 540 extends upwardly into the first recess 544 in a location between the side surfaces 582 and 584. Two elongated slots 588 and 590 connect the first recess 544 to the cavity 536 on longitudinally opposite ends of the protruding portion 586.

Two pivot pin holes 592 and 594 and a second recess 600 extend into the bottom surface 546 of the first recess 544. The pivot pin holes 592 and 594 are located in the slot 590 and a curved end surface 596 of the first recess 544. The second recess 600 extends longitudinally through a center of the first recess 544. Two axially extending ribs 602 extend into the second recess 600 near the curved end surface 596 of the first recess 544. The ribs 602 form three elongated slots in the second recess 600.

The base plate portion 514 also includes four fastener holes 604. The four fastener holes 604 extend between the lower and upper surfaces 520 and 522 of the base plate portion 514.

The top plate portion 516 of the housing 512 also a lower surface 610 (FIG. 37) and an upper surfaces 612 (FIG. 36). An elliptical aperture 621 extends through the top plate portion 516 of the housing 512. The elliptical aperture 621 extends between the lower and upper surfaces 610 and 612 and has a location corresponding the elliptical aperture 540 of the base plate portion 514. The upper surface 612 of the top plate portion 516 is chamfered adjacent the elliptical aperture 621.

Four fastener holes 622 and two pivot pin holes 624 and 626 also extend through top plate portion 516 between the lower and upper surfaces 610 and 612. Each of the four fastener holes 622 is associated with and has a location corresponding to a fastener hole 604 of the base plate portion 514 of the housing 512. Each of the fastener holes 622 is located in a circular boss 628 that extends upwardly above the upper surface 612 of the top plate portion 516. Each of the two pivot pin holes 624 and 626 is associated with and has a location corresponding to a pivot pin hole 592 and 594 of the base plate portion 514 of the housing 512.

Two longitudinally elongated slots 632 and 634 extend through the top plate portion 516. The slot 634 has a length and width of approximately four times the length and width of the slot 632.

The device 510 also includes a driver 640. FIG. 36 illustrates an oblique view of the driver 640 and FIGS. 38-41 illustrate a plan view of the driver located in the first recess 544 of the base plate portion 514 of the housing 512. For clarity in viewing the driver 640 in FIGS. 38-41, the protruding portion 586 of the base plate portion 514 that includes the elliptical aperture 540 is not shown.

The driver 640 is injection molded from a plastic material that is flexible enough to allow for a living hinge to be formed on the driver. Exemplary plastic materials include nylon, polycarbonate, polyester, or any other suitable polymer. The driver 640 includes a yoke portion 642 and a driving portion 644. The yoke portion 642 of the driver 640 includes longitudinally spaced first and second end portions 650 and 652, respectively, and laterally spaced first and second side portions 654 and 656, respectively, that collectively surround a central opening 658.

Figure 38:
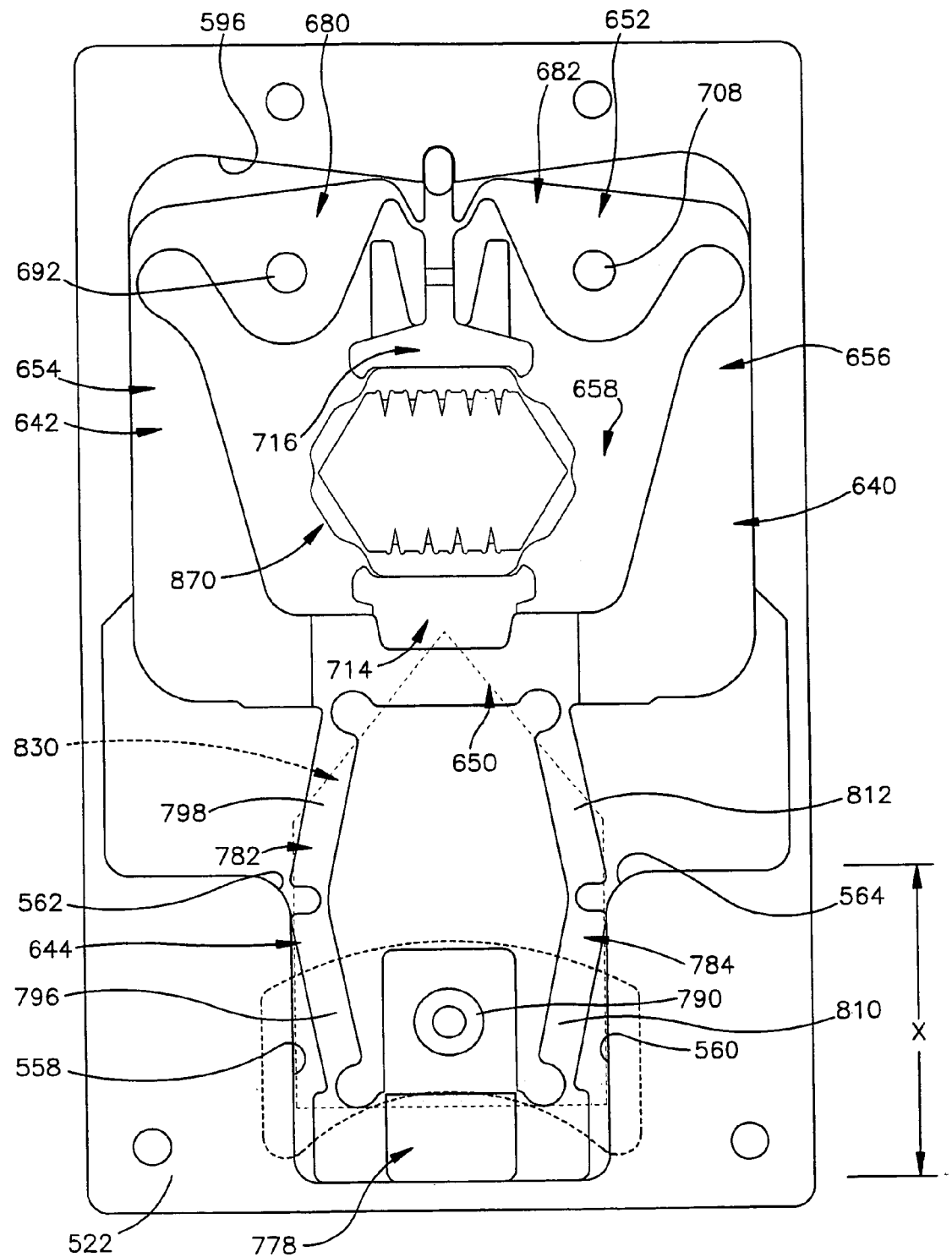
FIG. 38 is a plan view of a drive member of the device of FIG. 35 in a first position relative to a base plate portion of the device.

As shown in FIG. 38, the first and second side portions 654 and 656 of the yoke portion 642 of the driver 640 connect the first and second end portions 650 and 652. The second end portion 652 includes first and second pivotal drive portions 680 and 682 that are connected to the first and second side portions 654 and 656, respectively, with living hinges. As shown in FIG. 38, a pivot pin hole 692 extends through the first pivotal drive portion 680 and a pivot pin hole 708 extends through the second pivotal drive portion 682.

The yoke portion 642 of the driver 640 also includes proximal and distal engaging members 714 and 716. The proximal engaging member 714 extends into the central opening 658 from the first end portion 650. The proximal engaging member 714 includes a recessed end portion 734 (FIG. 37). The distal engaging member 716 is interposed between the first and second pivotal drive portions 680 and 682. The distal engaging member 716 also includes a recessed end portion 770 (FIG. 37).

The driving portion 644 of the driver 640 is located longitudinally opposite the first end portion 650 of the yoke portion 642 from the central opening 658. The driving portion 644 includes a blade support portion 778, and first and second collapsible legs 782 and 784, respectively.

The blade support portion 778 includes circular boss 790 (FIG. 38) that extends upwardly from the blade support portion 778. A rectangular protrusion (not shown) extends downwardly from the blade support portion 778 for being received in the second recess 600 of the base plate portion 514.

The first and second collapsible legs 782 and 784 are located on laterally opposite sides of the blade support portion 778. The first and second collapsible legs 782 and 784 extend between the blade support portion 778 and the first end portion 650 of the yoke portion 642. The first collapsible leg 782 includes first and second leg portions 796 and 798, respectively. Living hinges connect the first and second leg portions 796 and 798 to one another and to the blade support portion 778 and the first end portion 650 of the yoke portion 642. The second collapsible leg 784 includes first and second leg portions 810 and 812, respectively. Living hinges connect the first and second leg portions 810 and 812 to one another and to the blade support portion 778 and the first end portion 650 of the yoke portion 642.

With reference again to FIG. 36, the device 510 also includes a cutting member or blade 830. The blade 830 includes an aperture 836 that is sized for receiving the circular boss 790 that extends upwardly from the blade support portion 778 of the driving portion 644 of the driver 640. The blade 830 also includes a sharpened edge 838. The blade 830 is formed from surgical steel. In one embodiment of the invention, the blade 830 is formed from 440 stainless steel.

The device 510 also includes an actuator handle 844. The actuator handle 844 is molded from plastic. An aperture 846 extends through the actuator handle 844 for receiving the circular boss 790 that extends upwardly from the blade support portion 778 of the driving portion 644 of the driver 640 and a fastener 848 that fixes the actuator handle 844 to the boss 790.

To assemble the device 510, the driver 640 is placed in the first recess 544 of the base plate portion 514 of the housing 512 so that the central opening 658 of the yoke portion 642 of the driver receives the protruding portion 586 of the base plate portion. When the driver 640 is located in the base plate portion 514 of the housing 512, the proximal and distal engaging members 714 and 716 extends through the slots 588 and 590 in the base plate portion 514 and slightly into the cavity 536 (FIG. 37) in the lower surface 520 of the base plate portion 514.

The blade 830 is then placed on the driving portion 644 of the driver 640 so that the circular boss 790 extends through the aperture 836 in the blade. The blade 830 is also received in the first recess 544 of the base plate portion 514. The side surfaces 558 and 560 of the first portion 550 of the first recess 544 prevent the blade 830 from rotating about the circular boss 790 and relative to the base plate portion 514.

The top plate portion 516 of the housing 512 is placed over the base plate portion 514 of the housing. The slot 634 of the top plate portion 516 receives the circular boss 790 of the blade support portion 778 of the driving portion 644 of the driver 640. The slot 632 of the top plate portion 516 receives a portion of the distal engaging member 716. When the top plate portion 516 is properly positioned relative to the base plate portion 514, the pivot pin holes 624 and 626, the fastener holes 622, and the elliptical aperture 621 of the top plate portion 516 are in locations corresponding to the pivot pin holes 592 and 594, fastener holes 604, and the elliptical aperture 540 of the base plate portion 514. Also, the pivot pin holes 692 and 708 of the first and second drive portions 680 and 682 of the second end portion 652 of the yoke portion 642 of the driver 640 are aligned with the pivot pin holes 592 and 594 of the base plate portion 514 and the pivot pin holes 624 and 626 of the top plate portion 516.

Four fasteners 854 (FIG. 35) are then inserted through the fastener holes 622 of the top plate portion 516 and the fastener holes 604 of the base plate portion 514 to hold the top plate portion relative to the base plate portion. A first pivot pin 856 is inserted through the pivot pin hole 624 of the top plate portion 516, the pivot pin hole 692 in the first pivotal drive portion 680 of second end portion 652 of the yoke portion 642, and the pivot pin hole 592 in the base plate portion 514 of the housing 512. A second pivot pin 858 is inserted through the pivot pin hole 626 of the top plate portion 516, the pivot pin hole 708 in the second pivotal drive portion 682 of second end portion 652 of the yoke portion 642, and the pivot pin hole 594 in the base plate portion 514 of the housing 512.

The aperture 846 in the actuator handle 844 is aligned with the circular boss 790 of the blade support portion 778 of the driving portion 644 of the driver 640. The actuator handle 844 is pressed onto the circular boss 790 and a fastener 848 is inserted into the aperture 846 to lock the actuator handle to the boss. When the actuator handle 844 is placed on the circular boss 790, the circular boss 790 is located at a first end of the slot 634.

After assembly of the device 510 is complete, the device 510 is turned over so that a clip 870 may be attached to the device. Exemplary clips are illustrated in FIGS. 49-63 and will be discussed later in this application. The clip 870 of FIG. 37 includes opposite first and second retaining portions 872 and 874, respectively, that when pressed together clamp onto tissue.

To attach the clip 870 to the device 510, the clip 870 is placed in the cavity 536 that extends into the lower surface 520 of the base plate portion 514. The first retaining portion 872 of the clip 870 is placed on the recessed end portion 734 of the proximal engaging member 714 and the second retaining portion 874 of the clip 870 is placed on the recessed end portion 770 of the distal engaging member 716.

To use the device 510 for removing a lesion or other portion of tissue, the lower surface 520 of the base plate portion 514 of the housing 512 of the assembled device 510, to which the clip 870 has been attached, is placed against the patient's tissue so that the elliptical apertures 540 and 621 overlie the portion of tissue to be removed. A skin hook, or another device for grabbing the patient's tissue, is inserted through the elliptical apertures 540 and 621 of the housing 512 and hooks the portion of tissue. The portion of tissue is pulled through the clip 870 and the elliptical apertures 540 and 621 of the housing 512 so that the tissue is placed under tension.

Figure 39:
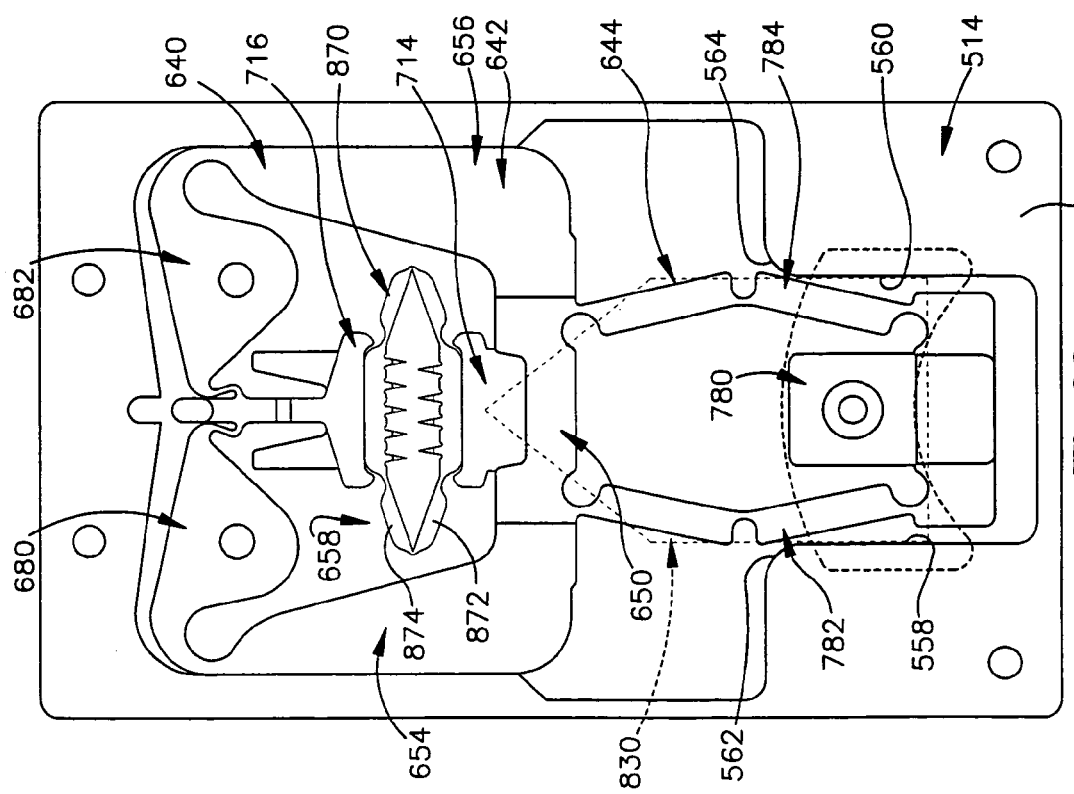
FIG. 39 is a plan view of the drive member in a second position relative to the base plate portion.

Pushing the actuator handle 844 through the slot 634 toward the elliptical aperture 621 actuates the device 510. When the actuator handle 844 begins to move toward the elliptical aperture 621, the first and second collapsible legs 782 and 784 are pressed against the side surfaces 558 and 560 of the first recess 544 in the base plate portion 514, as is shown in FIG. 38. As a result, the first and second collapsible legs 782 and 784 are prevented from collapsing and the movement of the actuator handle 844 causes the yoke portion 642 of the driver 640 begin to close the clip 870 so that tines of the clip penetrate the tissue and the clip begins to pinch the tissue. The first and second drive portions 680 and 682 of the yoke portion 642 of the driver 640 rotate to move the distal engaging member 716 by an amount equal to the movement of the proximal engaging member 714 to begin to close the clip 870. FIG. 39 illustrates the device 510 at a position in which the clip 870 begins to close.

Adjusting the location of the corners 562 and 564 enables the timing for cutting the tissue with the blade 830 and clamping the tissue with the clip 870 to be controlled. The longitudinal lengths of side surfaces 558 and 560, illustrates in FIG. 38 as distance X, controls the timing of when the first and second collapsible legs 782 and 784 of the driving portion 644 begin to collapse. Thus, by adjusting the distance X, the device 510 timing for cutting the tissue with the blade 830 and clamping the tissue with the clip 870 may be adjusted. For example, when the distance X is increased, the yoke portion 642 of the driver 640 will close the clip 870 prior to the driving portion 644 moving the blade 830 to cut the tissue.

When the first and second collapsible legs 782 and 784 of the driving portion 644 of the driver 640 move out of contact with the side surfaces 558 and 560 and over corners 562 and 564, respectively, the first and second collapsible legs 782 and 784 begin to collapse, as is shown in FIG. 39. When the first and second collapsible legs 782 and 784 begin to collapse, the blade support portion 778 begins to move toward the first end portion 650. During the movement of the blade support portion 778 toward the first end portion 650, the blade 830 cuts through the tissue that extends through the elliptical aperture 621 of the top plate portion 516 to excise the tissue from the tissue that extends through the elliptical aperture 540 of the base plate portion 514.

Figure 40:
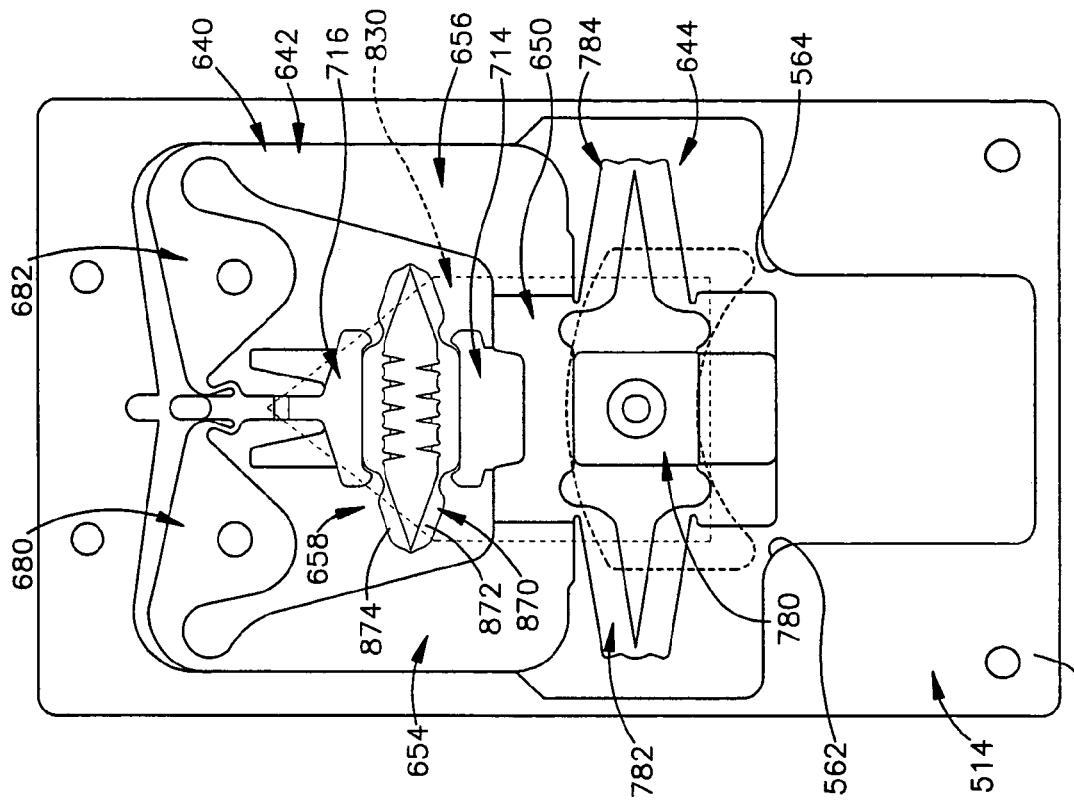
FIG. 40 is a plan view of the drive member in a third position relative to the base plate portion.

The tissue that extends into elliptical aperture 540 remains pinched between the first and second retaining portions 872 and 874 of the clip 870. After the blade support portion 778 of the driving portion 644 of the driver 640 contacts the first end portion 650 of the yoke portion 642 of the driver, as is shown in FIG. 40, further movement of the actuator handle 844 through the slot 634 toward the elliptical aperture 621 results in movement of the proximal engaging member 714 toward the center of the elliptical aperture 540 and equal movement of the distal engaging member 716 toward the center of the elliptical aperture 540. The proximal and distal engaging members 714 and 716 continue to move together as the actuator handle 844 is moved through the slot 634 toward the elliptical aperture 621. When the proximal and distal engaging members 714 and 716 move toward each other, the first and second retaining portions 872 and 874 of the clip 870 are pressed together into the position shown in FIG. 41. When the actuator handle 844 reaches the end of the slot 634, the clip 870 fully occludes the wound that results from the excision of the tissue.

After the clip 870 fully occludes the wound, the actuator handle 844 is moved in the slot 634 in a direction away from the elliptical aperture 621. Movement of the actuator handle 844 away from the elliptical aperture 621 causes the proximal and distal engaging member 714 and 716 to move apart from one another and to release the clip 870. As an alternative to manually moving the actuator handle 844 to remove the clip 870, the device 510 may be modified to include a biasing member or spring (not shown) that biases the first end portion 650 of the yoke portion 642 of the driver 640 relative to the base plate portion 514 to remove the clip 870 from the proximal and distal engaging member 714 and 716. For example, the biasing member may be an integral part of the driver 640.

Preferably, all of the parts of the device 510, with the exception of the blade 830 and the clip 870, are molded from plastic material. In a preferred embodiment, the device 510 is a single use device that is discarded after its use, while the clip 870 remains attached to the skin to close the wound.

Figure 43:
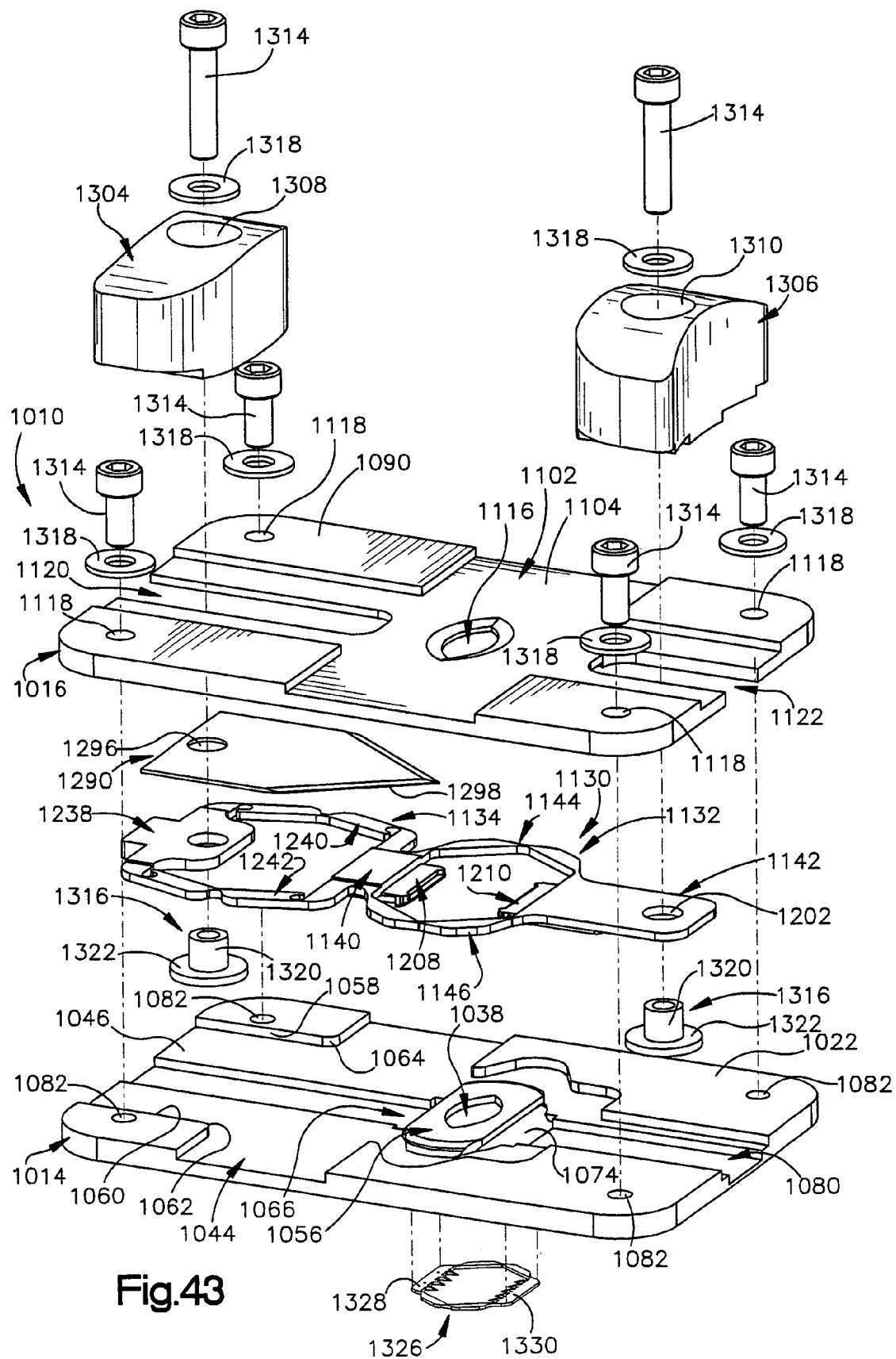
FIG. 43 is an oblique, exploded view of the device of FIG. 42.
Figure 44:
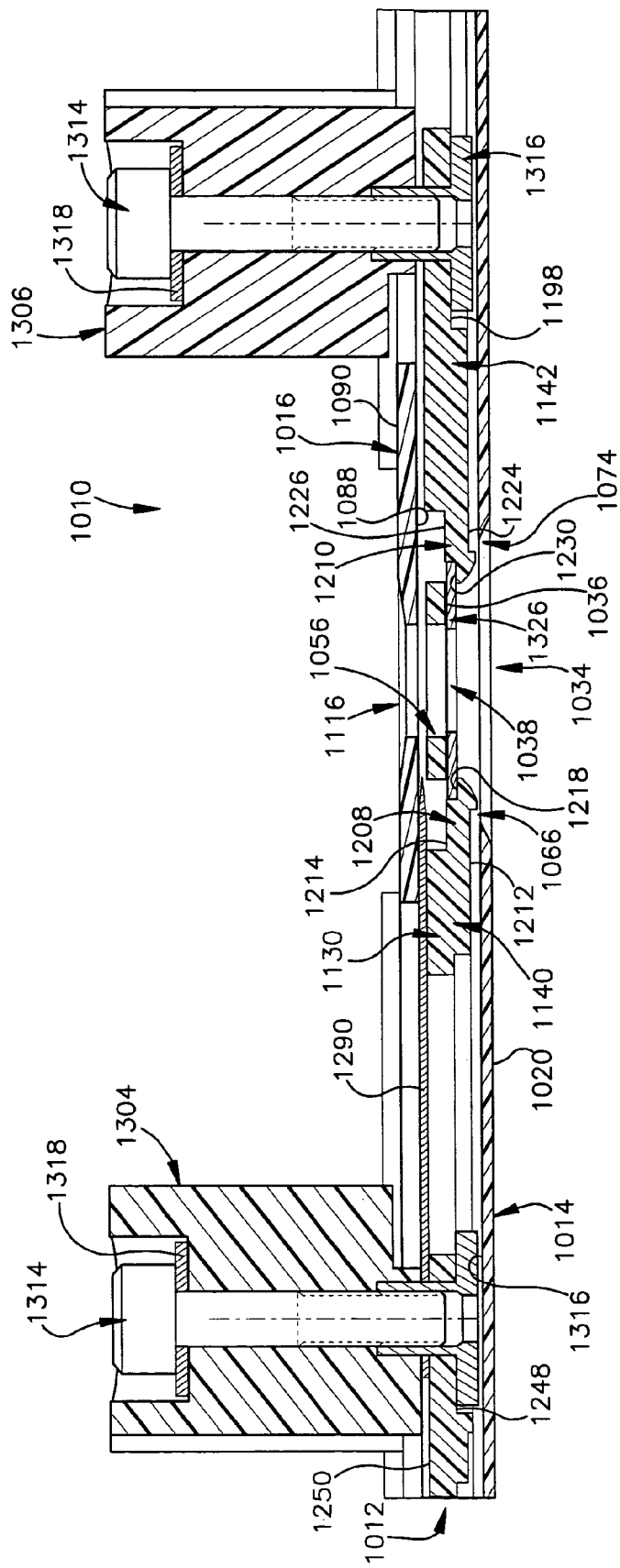
FIG. 44 is a sectional view of the device of FIG. 42.

FIG. 42 is an oblique view of a second exemplary device constructed in accordance with the fifth embodiment of the present invention. FIG. 43 is an exploded oblique view of the device 1010 and FIG. 44 is a sectional view of the device 1010.

The device 1010 includes a housing 1012 having a base plate portion 1014 and a top plate portion 1016. The base plate portion 1014 of the housing 1012 includes a lower surface 1020 (FIG. 44) and an upper surfaces 1022 (FIG. 43). A cavity 1034 (FIG. 44) extends upwardly into the lower surface 1020 of the base plate portion 1014. The cavity 1034 terminates at an upper surface 1036. An elliptical aperture 1038 extends through the base plate portion 1014 through the upper surface 1036 of the cavity 1034.

With reference to FIG. 43, a first recess 1044 extends downwardly into the upper surface 1022 of the base plate portion 1014. The first recess 1044 includes a generally planar bottom surface 1046. A protruding portion 1056 having the elliptical aperture 1038 extends upwardly from the bottom surface 1046 of the first recess 1044. As shown in FIG. 44, elongated slots 1066 and 1074 are located on opposite sides of the protruding portion 1056 and connect the first recess 1044 to the cavity 1034.

Figure 45:
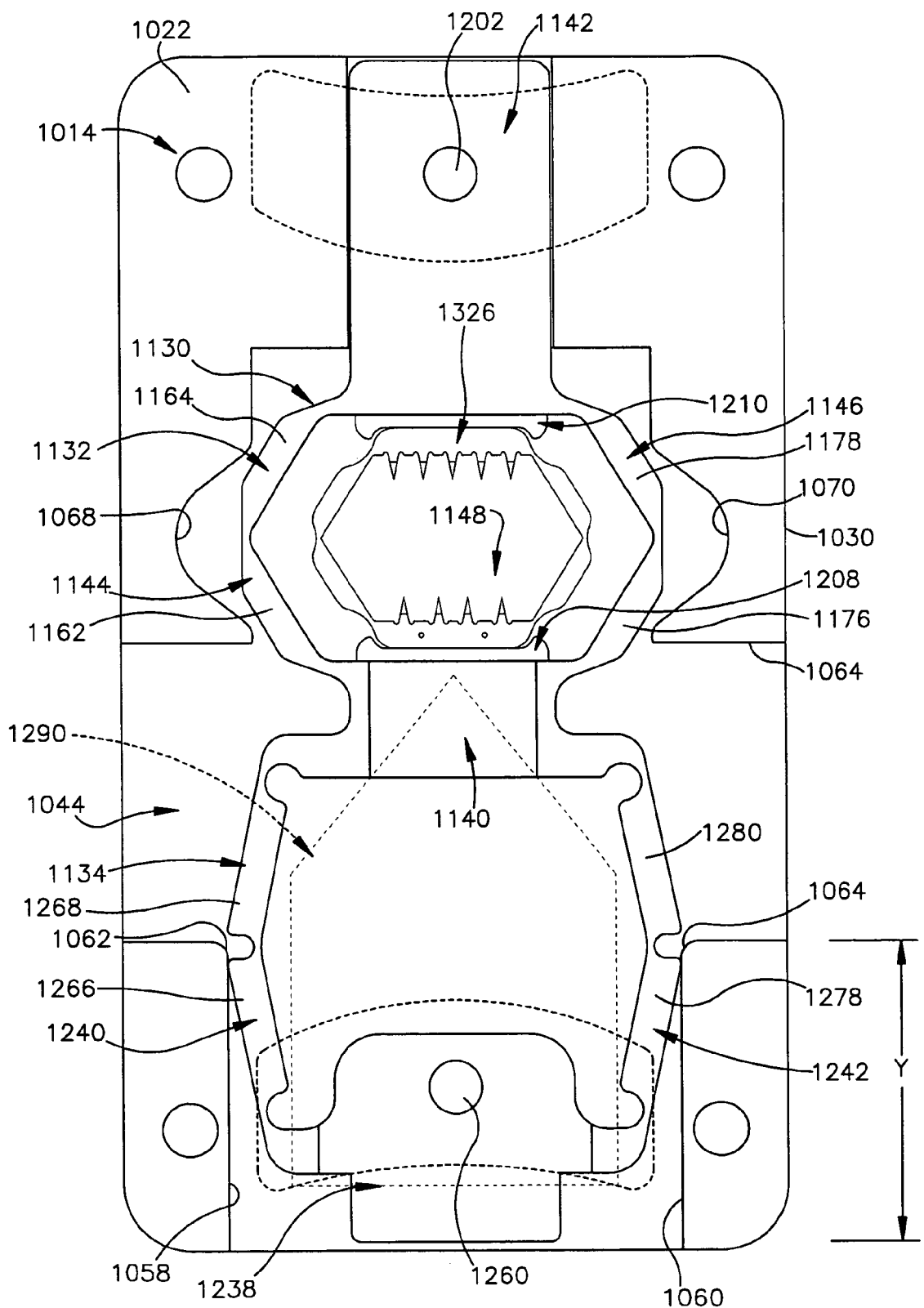
FIG. 45 is a plan view of a drive member of the device of FIG. 42 in a first position relative to a base plate portion of the device.

The first recess 1044 includes a narrowed section having laterally opposite side surfaces 1058 and 1060. As shown in FIG. 45, corners 1062 and 1064, which preferably have equal radii, form transitions between the laterally opposite side surfaces 1058 and 1060 and a wider section of the first recess 1044. As will be discussed below, the location of the corners 1062 and 1064 determines a timing for cutting the lesion and clamping the skin adjacent the lesion.

The first recess 1044 also includes a generally elliptical section that includes arcuate side surfaces 1068 and 1070. The arcuate sides surfaces 1068 and 1070 are located on laterally opposite sides of the protruding portion 1056.

A second recess 1080 extends downwardly into the bottom surface 1046 of the first recess 1044. The second recess 1080 extends longitudinally through a center of the first recess 1044.

The base plate portion 1014 also includes four fastener holes 1082. The four fastener holes 1082 extend between the lower and upper surfaces 1020 and 1022 of the base plate portion 1014.

The top plate portion 1016 of the housing 1012 also includes a lower surface 1088 (FIG. 44) and an upper surfaces 1090. A recess 1102 extends into the upper surface 1090 of the top plate portion 1016. The recess 1102 has a planar bottom surface 1104. An elliptical aperture 1116 extends through the top plate portion 1016 of the housing 1012. The elliptical aperture 1116 extends between the bottom surface 1104 of the recess 1102 and the lower surface 1020 of the top plate portion 1016. The elliptical aperture 1116 has a location corresponding the elliptical aperture 1038 of the base plate portion 1014.

Four fastener holes 1118 extend through top plate portion 1116 between the lower and upper surfaces 1020 and 1022. Each of the four fastener holes 1118 is associated with and has a location corresponding to a fastener hole 1082 of the base plate portion 1014 of the housing 1012.

Two axially elongated slots 1120 and 1122 extend through the top plate portion 1016. The slots 1120 and 1122 extend along a centerline of the top plate portion 1016 from longitudinally opposite ends of the top plate portion.

The device 1010 also includes a driver 1130. FIG. 45-48 illustrate plan views of the driver 1130 in the base plate portion 1014 of the housing 1012. For clarity in viewing the driver 1130 in FIGS. 45-48, the protruding portion 1056 of the base plate portion 1014 that includes the elliptical aperture 1038 is not shown.

The driver 1130 is injection molded from plastic material and includes a yoke portion 1132 and a cutting portion 1134. The yoke portion 1132 of the driver 1130 includes opposite first and second end portions 1140 and 1142, respectively, and opposite first and second collapsible legs 1144 and 1146, respectively. A central opening 1148 extends between the first and second end portions 1140 and 1142 and the first and second collapsible legs 1144 and 1146, respectively.

As shown in FIG. 45, the first and second collapsible legs 1144 and 1146 connect the first and second end portions 1140 and 1142. The first collapsible leg 1144 includes first and second leg portions 1162 and 1164, respectively. Living hinges connect the first and second leg portions 1162 and 1164 to one another and to the first and second end portions 1140 and 1142. The second collapsible leg 1146 also includes first and second leg portions 1176 and 1178, respectively. Living hinges connect the first and second leg portions 1176 and 1178 to one another and to the first and second end portions 1140 and 1142.

The yoke portion 1132 of the driver 1130 also includes proximal and distal engaging members 1208 and 1210, respectively. The proximal engaging member 1208 extends longitudinally outwardly of the first end portion 1140 and into the central opening 1148. The proximal engaging member includes a recessed end portion 1218 (FIG. 44). The distal engaging member 1210 also extends longitudinally into the central opening 1148. The distal engaging member includes a recessed end portion 1230 (FIG. 44).

The cutting portion 1134 of the driver 1130 is located longitudinally opposite the first end portion 1140 of the yoke portion 1132 from the central opening 1148. As shown in FIG. 43, the cutting portion 1134 includes a blade support portion 1238 and first and second collapsible legs 1240 and 1242, respectively. A circular aperture 1260 extends through the blade support portion 1238. A rectangular protrusion extends downwardly from the blade support portion 1238 for being received in the second recess 1080 of the base plate portion 1014.

The first and second collapsible legs 1240 and 1242 extend longitudinally between the blade support portion 1238 and the first end portion 1140 of the clamping portion 1232. The first collapsible leg 1240 includes first and second leg portions 1266 and 1268, respectively. Living hinges connect the first and second leg portions 1266 and 1268 together and to the blade support portion 1238 and the first end portion 1140. The second collapsible leg 1242 also includes first and second leg portions 1278 and 1280, respectively. Living hinges connect the first and second leg portions 1278 and 1280 together and to the blade support portion 1238 and the first end portion 1140.

As shown in FIG. 43, the device 1010 also includes a cutting member or blade 1290. The blade 1290 includes an aperture 1296 and a sharpened edge 1298. The blade 1290 is formed from surgical steel. In one embodiment of the invention, the blade is formed from 440 stainless steel.

The device 1010 also includes first and second actuator handles 1304 and 1306, respectively. The actuator handles 1304 and 1306 are molded from plastic. An aperture 1308 extends vertically through actuator handle 1304. Likewise, an aperture 1310 extends vertically through actuator handle 1306.

The device 1010 also includes six fastener 1314 and two blind nuts 1316. The fasteners 1314 illustrated in FIG. 43 are screws having associated washers 1318. Alternatively, snap features may be incorporated into the various structures of the device 1010. The six fasteners 1314 include four housing fasteners and two actuator fasteners. Each of the two blind nuts 1316 includes a circular boss 1320 and a planar base 1322. The planar bases 1322 of the blind nuts 1316 are sized for being received in the second recess 1080 of the base plate portion 1014 of the housing 1012.

To assemble the device 1010, a circular boss 1320 of one of the blind nut 1316 is inserted into the aperture 1260 of the blade support portion 1238 of the driver 1130 so that the circular boss extends upwardly beyond an upper surface of the blade support portion. The circular boss 1320 of the other blind nut 1316 is inserted into an aperture 1202 of the second end portion 1142 so that the circular boss extends upwardly beyond an upper surface of the second end portion. The driver 1130 is then placed in the first recess 1044 of the base plate portion 1014 of the housing 1012 so that the central opening 1148 of the yoke portion 1132 of the driver receives the protruding portion 1056 of the base plate portion that includes the elliptical aperture 1038. When the driver 1130 is placed in the first recess 1044, the bases 1322 of the blind nuts 1316 and the rectangular protrusions of the blade support portion 1238, the first end portion 1140, and the second end portion 1142 are received in the second recess 1080 of the base plate portion 1014. The second recess 1080 acts to guide the driver 1130 during movement relative to the base plate portion 1014.

When the driver 1130 is located in the base plate portion 1014 of the housing 1012, the proximal and distal engaging members 1208 and 1210 extends through the slots 1062 and 1074 in the base plate portion 1014 and slightly into the cavity 1034 of the base plate portion. The driver 1130 is positioned within the first recess 1044 so that the first and second collapsible legs 1240 and 1242 of the cutting portion 1134 of the driver 1130 engage the first and second side surfaces 1058 and 1060 of the first portion 1048 of the first recess 1044, as is shown in FIG. 45.

The blade 1290 is then placed over the blade support portion 1238 of the cutting portion 1134 of the driver 1130 so that the circular boss 1320 of the blind nut 1316 that extends through the aperture 1260 in the blade support portion also extends through the aperture 1296 of the blade. The blade 1290 is also received in the first recess 1044 of the base plate portion 1014. The first and second side surfaces 1058 and 1060 of the first portion 1048 of the first recess 1044 prevent the blade 1290 from rotating about the circular boss 1320 and relative to the base plate portion 1014.

The top plate portion 1016 of the housing 1012 is placed over the base plate portion 1014 of the housing. The slot 1120 of the top plate portion 1016 receives the circular boss 1320 of the blind nut 1316 that extends through the aperture 1296 of the blade 1290. The slot 1122 receives the circular boss 1320 of the blind nut 1316 that extends through the second end portion 1142 of the yoke portion 1132 of the driver 1130. When the top plate portion 1016 is properly positioned relative to the base plate portion 1014, the fastener holes 1118 and the elliptical aperture 1116 of the top plate portion 1016 are in locations corresponding to the fastener holes 1082 and the elliptical aperture 1038 of the base plate portion 1014.

Four fasteners 1314 are then inserted through the fastener holes 1118 of the top plate portion 1016 and the fastener holes 1082 of the base plate portion 1014 to hold the top plate portion relative to the base plate portion. The aperture 1308 in the actuator handle 1304 is aligned with and receives the circular boss 1320 of the blind nut 1316 that extends through the aperture 1296 of the blade 1290. A fastener 1314 fixes the actuator handle 1304 to the blind nut 1316. The aperture 1310 in the actuator handle 1306 is aligned with and receives the circular boss 1320 of the blind nut 1316 that extends through the aperture 1202 in the second end portion 1142. A fastener 1314 fixes the actuator handle 1306 to the blind nut 1316.

After assembly of the device 1010 is complete, the device 1010 is turned over so that a clip 1326 may be attached to the device. Exemplary clips are illustrated in FIGS. 49-63 and are discussed later in this application. The clip 1326 of FIG. 43 includes opposite first and second retaining portions 1228 and 1230, respectively, that when pressed together clamp onto tissue.

To attach the clip 1326 to the device 1010, the clip 1326 is placed in the cavity 1034 that extends into the lower surface 1020 of the base plate portion 1014. The first retaining portion 1328 of the clip 1326 is supported on the recessed end of the proximal engaging member 1208 and the second retaining portion 1330 is supported on the recessed end of the distal engaging member 1210.

To use the device 1010 for removing a lesion or other portion of tissue, the lower surface 1020 of the base plate portion 1014 of the assembled device 1010, to which the clip 1326 has been attached, is placed against a patient's tissue. A skin hook, or another device for grabbing the patient's tissue, is inserted through the elliptical apertures 1038 and 1116 of the housing 1012 and grabs the tissue. The skin hook pulls the tissue through the clip 1326 and the elliptical apertures 1038 and 1116 of the housing 1012. When pulled through the elliptical apertures 1038 and 1116, the tissue is placed under tension.

Figure 46:
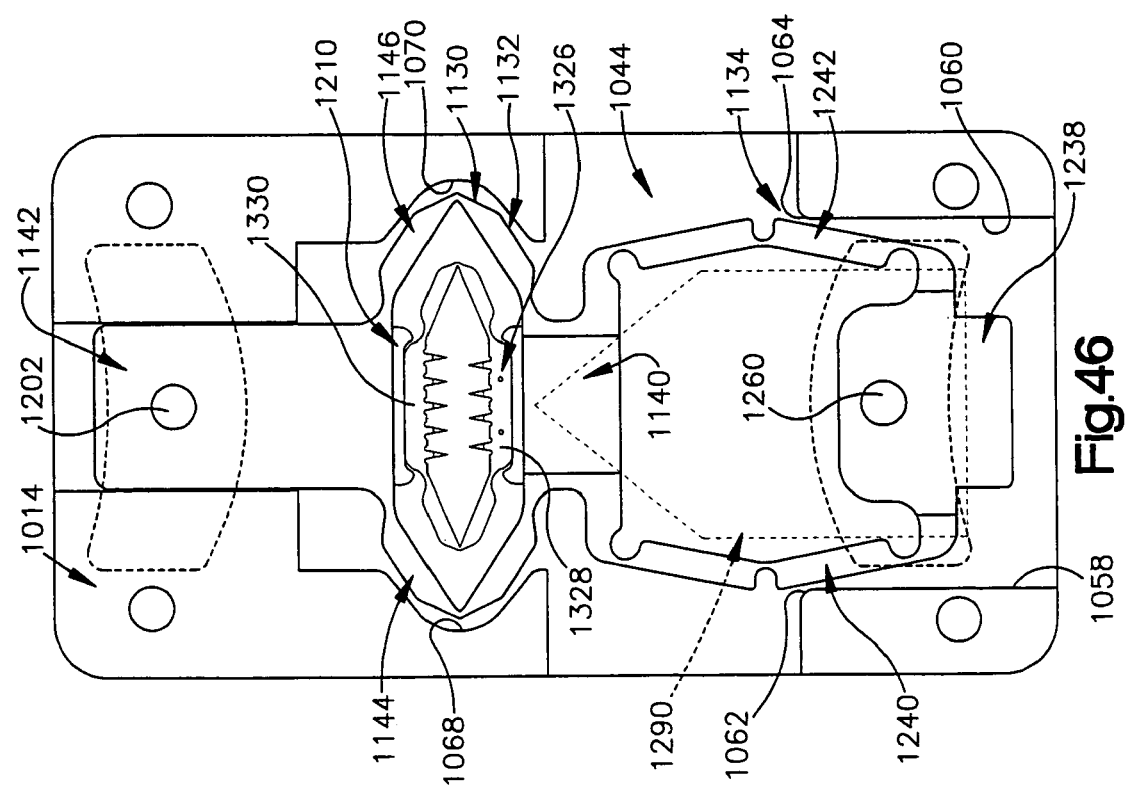
FIG. 46 is a plan view of the drive member in a second position relative to the base plate portion.

The first and second actuator handles 1304 and 1306 are pushed together to actuate the driver 1130. When the first and second actuator handles 1304 and 1306 are moved toward one another, the side surfaces 1058 and 1060 of the first portion 1048 of the first recess 1044 prevent the first and second collapsible legs 1240 and 1242 of the cutting portion 1134 of the driver 1130 from collapsing, as illustrated in FIG. 45. As a result, the proximal and distal engaging members 1208 and 1210 moves toward one another to begin closing the clip 1326. When the clip 1326 begins to close, tines of the clip 1326 pierce the tensioned tissue and the clip begins to pinch the tissue. FIG. 46 illustrates the device 1010 with the clip 1326 partially closed.

Adjusting the location of the corners 1062 and 1064 enables the timing for cutting the tissue with the blade 1290 and clamping the tissue with the clip 1326 to be controlled. The longitudinal lengths of side surfaces 1058 and 1060, illustrates in FIG. 45 as distance Y, controls the timing of when the first and second collapsible legs 1240 and 1242 of the cutting portion 1134 of the driver 1130 begin to collapse. Thus, by adjusting the distance Y, the device 1010 timing for cutting the tissue with the blade 1290 and clamping the tissue with the clip 1326 may be adjusted. For example, when the distance Y is increased, the yoke portion 1132 of the driver 1130 will close the clip 1326 prior to the cutting portion 1134 moving the blade 1290 to cut the tissue.

When the living hinges of the first and second collapsible legs 1240 and 1242 of the cutting portion 1134 of the driver 1130 extend longitudinally beyond the corners 1062 and 1064, as is shown in FIG. 46, the collapsible legs 1240 and 1242 begin to collapse. As the actuator handle 1304 continues to move toward through slot 1120 toward the elliptical aperture 1116, the collapsible legs 1240 and 1242 of the cutting portion 1134 of the driver 1130 collapse into the position illustrated in FIG. 47 and the blade support portion 1238 moves into contact with the first end portion 1140 of the yoke portion 1132 of the driver 1130. During the movement of the blade support portion 1238 toward the first end portion 1140, the blade 1290 cuts the tissue that extends through the elliptical aperture 1116 of the top plate portion 1016 of the housing 1012.

Figure 48:
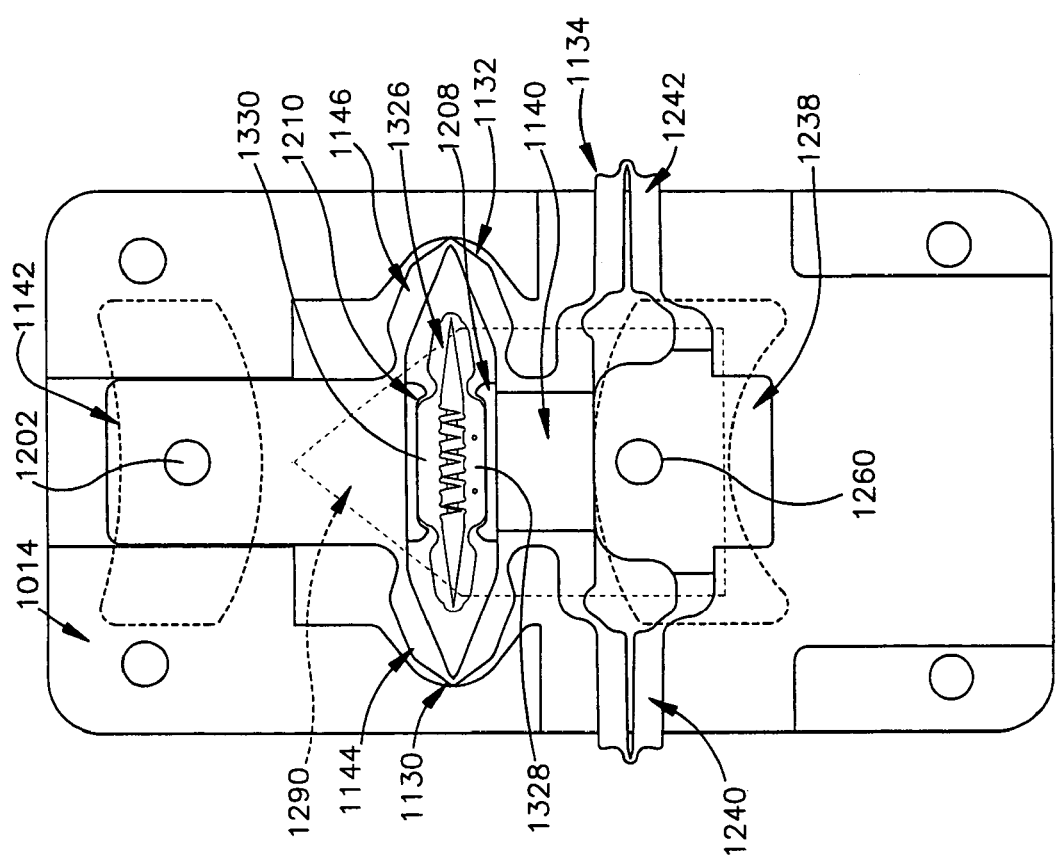
FIG. 48 is a plan view of the drive member in a fourth position relative to the base plate portion.

The tissue that extends through the elliptical aperture 1038 of the base plate portion 1014 of the housing 1012 remains pinched between the first and second retaining portions 1328 and 1330 of the clip 1326. After the blade support portion 1238 of the cutting portion 1134 of the driver 1130 contacts the first end portion 1140 of the yoke portion 1132 of the driver, further movement of the actuator handles 1304 and 1306 toward one another and toward the elliptical aperture 1116 moves the proximal engaging member 1208 and the distal engaging member 1210, respectively, toward a center of the elliptical aperture 1116. The proximal and distal engaging members 1208 and 1210 continue to move together as the actuator handles 1304 and 1306 are moved toward one another so as to press the first and second retaining portions 1328 and 1330 of the clip 1326 together. When the first and second actuator handles 1304 and 1306 reach the ends of the slots 1120 and 1122, respectively, the first and second retaining portions 1328 and 1330 of the clip 1326 fully occlude the wound that results from excision of the tissue. FIG. 48 illustrates the driver 1130 and the clip 1326 when the clip is in a closed condition.

After the clip 1326 fully occludes the wound, the actuator handles 1304 and 1306 are moved away from one another to cause the proximal and distal engaging members 1208 and 1210 to move apart from one another and to release the clip 1326. As an alternative to manually moving the actuator handles 1304 and 1306 away from one another, the device 1010 may be modified to include a biasing member or spring that biases the first end portion 1140 of the yoke portion 1132 of the driver 1130 in a direction for releasing the clip 1326. For example, the biasing member may form an integral part of the driver 1130.

Preferably, all of the parts of the device 1010, with the exception of the blade 1290 and the clip 1326, are molded from plastic. In a preferred embodiment, the device 1010 is a single use device that is discarded after its use while the clip 1326 remains attached to the skin to close the wound. The device 1010 may come in various sizes for removing lesions of various sizes. When multiple sizes of the device 1010 are available, a template may be supplied for enabling the clinician to determine the correct size of the device 1010 to be used in removing the desired lesion.

Figures 49, 50:
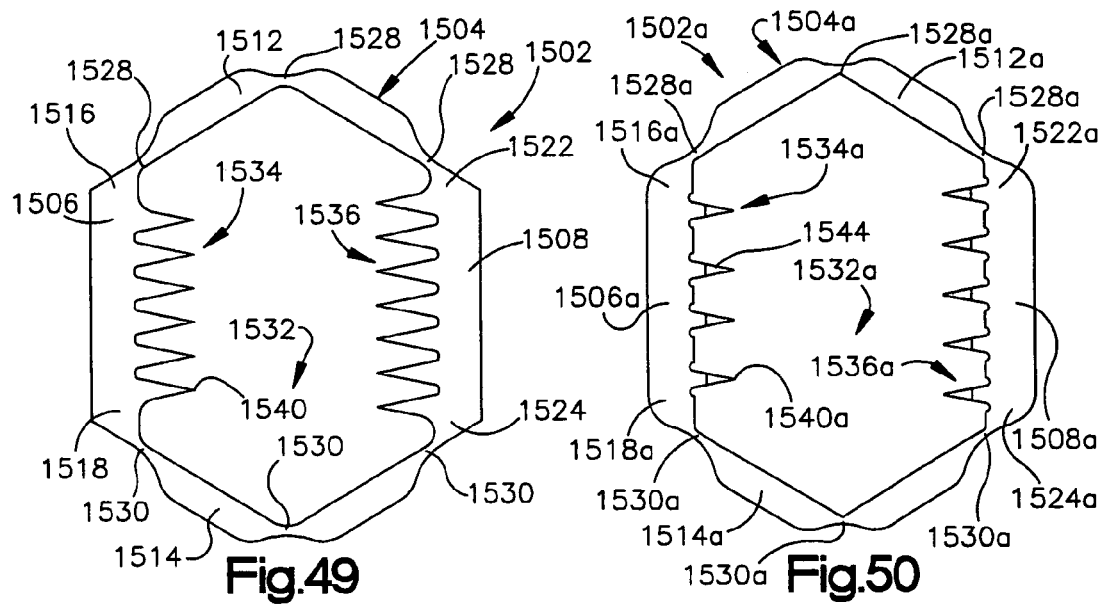
FIG. 49 is a first exemplary embodiment of a closure member for use with the devices of FIGS. 35 and 42.
FIG. 50 is a second exemplary embodiment of a closure member.

FIG. 49 is a first exemplary embodiment of a closure member or clip 1502. The clip 1052 of FIG. 49 may be used with the devices 510 and 1010 of FIGS. 35 and 42. The clip 1502 is preferably stamped from stainless steel, titanium, or any other bio-compatible metal.

The clip 1502 includes a planar body portion 1504. The body portion 1504 of the clip 1502 includes first and second retaining portions 1506 and 1508, respectively, and first and second deformable portions 1512 and 1514, respectively. The first retaining portion 1506 includes opposite first and second ends 1516 and 1518, respectively. Likewise, the second retaining portion 1508 includes opposite first and second ends 1522 and 1524, respectively.

The first deformable portion 1512 connects the first end 1516 of the first retaining portion 1506 and the first end 1522 of the second retaining portion 1508. The first deformable portion 1512 includes three deformation zones 1528. Each of the deformation zones 1528 is formed from a thinned portion of the first deformable portion 1512. Each deformation zone 1528 has a width, measured within the plane of the body portion 1504 of the clip 1502, i.e., within the plane of FIG. 49, that is less than a material thickness of the first deformable portion 1512, measured in a direction perpendicular to the plane of the body portion of the clip, i.e., into FIG. 49.

The second deformable portion 1514 connects the second end 1518 of the first retaining portion 1506 and the second end 1524 of the second retaining portion 1508. The second deformable portion 1512 also includes three deformation zones 1530. Each of the deformation zones 1530 of the second deformable portion 1514 has a width, measured within the plane of the body portion 1504 of the clip 1502, that is less than a material thickness of the second deformable portion 1514, measured in a direction perpendicular to the plane of the body portion of the clip.

An oblong or elliptical opening 1532 is formed between the first and second retaining portions 1506 and 1508 and the first and second deformable portions 1512 and 1514. A first set of tines 1534 extends outwardly of the first retaining member 1506 and into the opening 1532. A second set of tines 1536 extends outwardly of the second retaining member 1508 and into the opening 1532. The first and second sets of tines 1534 and 1536 are adapted to puncture tissue and, thus, each of the tines ends in a point, indicated as 1540 on one of the tines in FIG. 49.

The clip 1502 has an open condition shown in FIG. 49 and a closed condition. FIGS. 41 and 48 illustrate clips 870 and 1326 that are similar to clip 1502 in closed conditions. When in the open condition, the opening 1532 of the clip 1502 is adapted to receive tissue. In the closed condition, the first and second retaining portions 1506 and 1508 of the clip 1502 move together to clamp the tissue and occlude a wound. When the clip 1502 is in the closed condition, the first and second sets of tines 1534 and 1536 pierce the tissue that is received in the opening 1532 for retaining the clip to the tissue.

Figure 47:
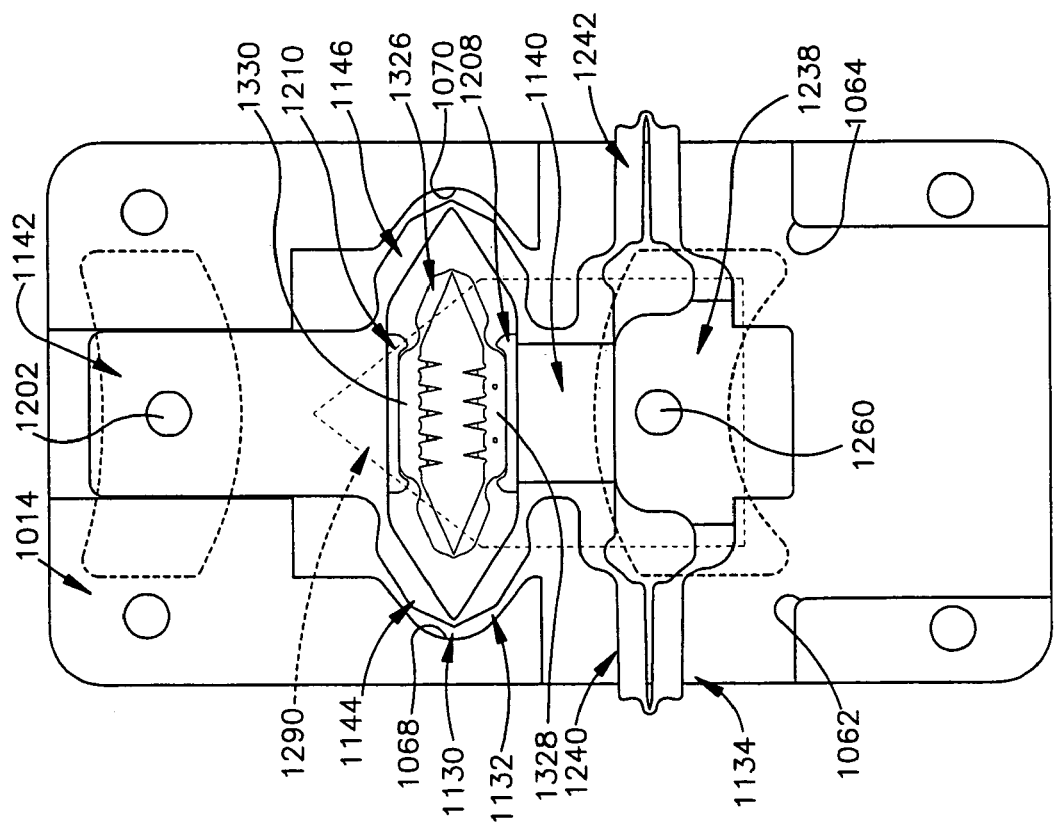
FIG. 47 is a plan view of the drive member in a third position relative to the base plate portion.

The body portion 1504 of the clip 1502 may be planar in both the open condition and the closed condition. The body portion 1504 may also be planar during movement between the open and closed conditions. It should be understood by those of ordinary skill in the art that the configuration of the clip 1502 may be changed to be non-planar, such as by placing tines of the clip 1502 out of a plane of the body portion 1504. FIGS. 39 and 40 illustrate a clip 870 that is similar to clip 1502 during movement between the open and closed conditions. Similarly, FIGS. 46 and 47 illustrate a clip 1326 that is similar to clip 1502 during movement between the open and closed conditions. During movement between the open and closed conditions, the deformation zones 1528 and 1530 of the deformable portions 1512 and 1514 of the clip 1502 are deformed to enable movement within the plane of the body portion 1504.

FIG. 50 illustrates a second exemplary embodiment of a clip 1502a. The clip 1502a of FIG. 50 is similar to the clip 1502 of FIG. 49 and therefore, structures of FIG. 50 that are the same as or similar to those described with reference to FIG. 49 have the same reference numbers with the addition of the suffix "a".

The clip 1502a of FIG. 50 is identical to the clip 1502 of FIG. 49 with the exception of the first and second sets of tines 1534a and 1536a. In FIG. 50, the first and second sets of tines 1534a and 1536a include fewer tines that the first and second sets of tines 1534 and 1536 of FIG. 49. Also, in FIG. 50, each tine of the first and second sets of tines 1534a and 1536a includes a tapered surface 1544. The tapered surface 1544 sharpens the point 1540a of each of the tines of the first and second sets of tines 1534a and 1536a.

Figure 51:
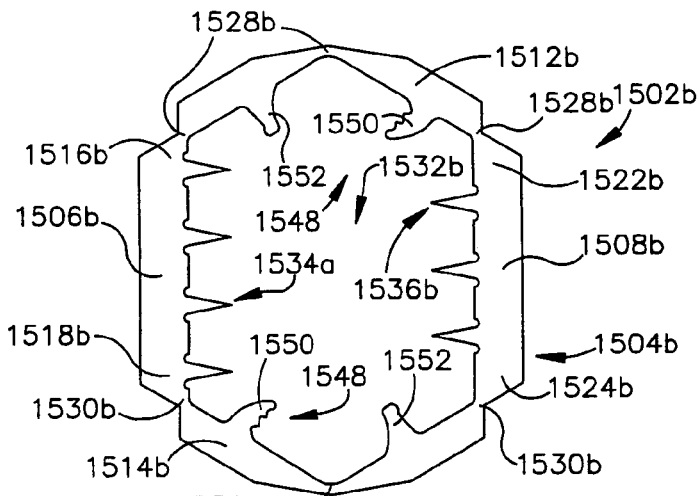
FIG. 51 is a third exemplary embodiment of a closure member.

FIG. 51 illustrates a third exemplary embodiment of a clip 1502b. The clip 1502b of FIG. 51 is similar to the clip 1502 of FIG. 49 and therefore, structures of FIG. 51 that are the same as or similar to those described with reference to FIG. 49 have the same reference numbers with the addition of the suffix "b".

The clip 1502b of FIG. 51 is identical to the clip 1502 of FIG. 49 with the exception of the first and second sets of tines 1534b and 1536b and the inclusion of locking devices 1548. In FIG. 51, the first and second sets of tines 1534b and 1536b include fewer tines that the first and second sets of tines 1534 and 1536 of FIG. 49. Also, in FIG. 51, the clip 1502b includes the locking devices 1548 for locking the clip in the closed condition.

One locking device 1548 is associated with each of the first and second deformable portions 1512b and 1514b. Each locking device 1548 includes first and second toothed members 1550 and 1552, respectively. When the clip 1502b moves into the closed condition, the first and second toothed members 1550 and 1552 of the locking devices 1548 mesh together to lock the clip in the closed condition.

Figure 52:
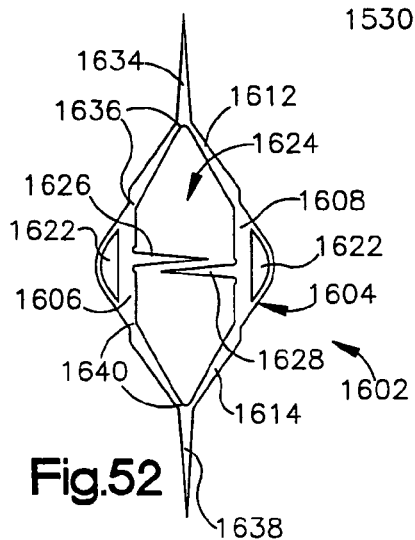
FIG. 52 is a fourth exemplary embodiment of a closure member.

FIG. 52 illustrates a fourth exemplary embodiment of the clip 1602. The clip 1602 includes a planar body portion 1604 having first and second retaining portions 1606 and 1608, respectively, and first and second deformable portions 1612 and 1614, respectively. The first and second retaining portions 1612 and 1614 include docking features 1622 for enabling the first and second retaining portions to be docked onto a closing device.

An opening 1624 in the clip 1602 is formed from the first and second retaining portions 1606 and 1608 and the first and second deformable portions 1612 and 1614. FIG. 52 illustrates the clip 1602 having a single tine 1626 that extends inwardly into the opening 1624 from the first retaining portion 1612 and a single tine 1628 that extends inwardly into the opening 1624 from the second retaining portion 1614. Prior to use, the tines 1626 and 1628 are bent to extend at an angle of in the range of approximately twenty to ninety degrees relative to the planar body portion 1604.

The first deformable portion 1612 of the clip 1602 includes a single outwardly extending tine 1634 and four deformation zones 1636, only two of which are labeled in FIG. 52. Likewise, the second deformable portion 1614 of the clip 1602 includes a single outwardly extending tine 1638 and four deformation zones 1640, only two of which are labeled in FIG. 52. Each of the deformation zones 1636 and 1640 of the clip 1602 has a width, measured within the plane of the body portion 1604, that is less than a material thickness of the body portion, measured in a direction perpendicular to the plane of the body portion of the clip so as to enable the clip to remain planar during movement from an open condition to a closed condition.

Figure 53:
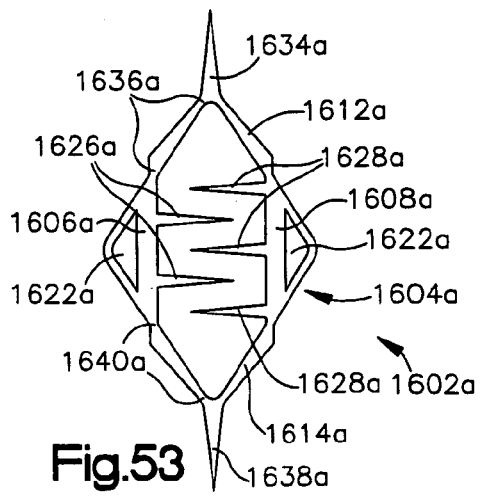
FIG. 53 is a fifth exemplary embodiment of a closure member.

FIG. 53 illustrates a fifth exemplary embodiment of a clip 1602a. The clip 1602a of FIG. 53 is similar to the clip 1602 of FIG. 51 and therefore, structures of FIG. 53 that are the same as or similar to those described with reference to FIG. 52 have the same reference numbers with the addition of the suffix "a".

The clip 1602a of FIG. 53 is identical to the clip 1602 of FIG. 52 with the exception of the number of inwardly extending tines. FIG. 53 illustrates the clip 1602a having two tines 1626a that extend inwardly into the opening 1624a from the first retaining portion 1606a and three tines 1628a that extends inwardly into the opening from the second retaining portion 1608a. Prior to use, the tines 1626a and 1628a are bent to extend at an angle of in the range of approximately twenty to ninety degrees relative to the planar body portion 1604a.

Figure 54:
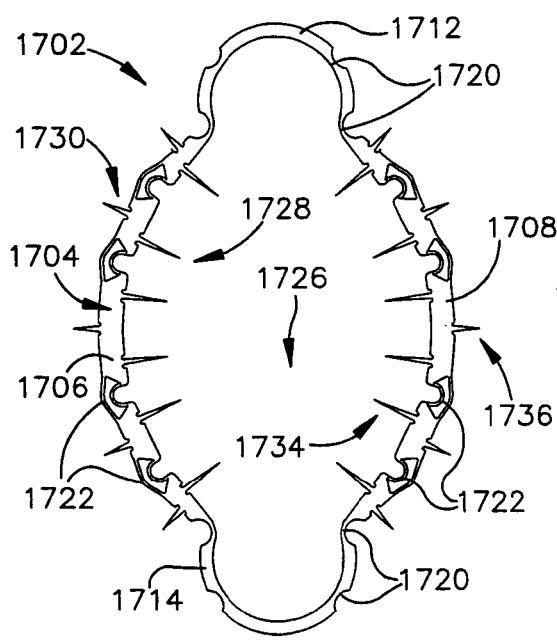
FIG. 54 is a sixth exemplary embodiment of a closure member.

FIG. 54 illustrates a sixth embodiment of the clip 1702. The clip 1702 includes a planar body portion 1704 that includes first and second retaining portions 1706 and 1708, respectively, and first and second deformable portions 1712 and 1714, respectively.

The first and second deformable portions 1712 and 1714 of the clip 1702 include deformation zones 1720. The first and second retaining portions 1706 and 1708 include expansion zones 1722. The deformation zones 1720 and the expansion zones 1722 enable the body portion 1704 of the clip 1702 to remain planar during movement from an open condition to a closed condition.

An opening 1726 in the clip 1702 is located between the first and second retaining portions 1706 and 1708 and the first and second deformable portions 1712 and 1714. The first retaining portion 1706 of the clip 1702 includes a first set of tines 1728 that extends inwardly into the opening 1726 and a second set of tines 1730 that extends outwardly away from the opening. Likewise, the second retaining portion 1708 of the clip 1702 includes a first set of tines 1734 that extends inwardly into the opening 1726 and a second set of tines 1736 that extends outwardly away from the opening. All of the tines 1728, 1730, 1734, and 1736 of the clip 1702 extend radially relative to a center of the opening 1726. Prior to use, the tines 1728, 1730, 1734, and 1736 are bent to extend at an angle of in the range of approximately twenty to ninety degrees relative to the planar body portion 1704.

Figure 55:
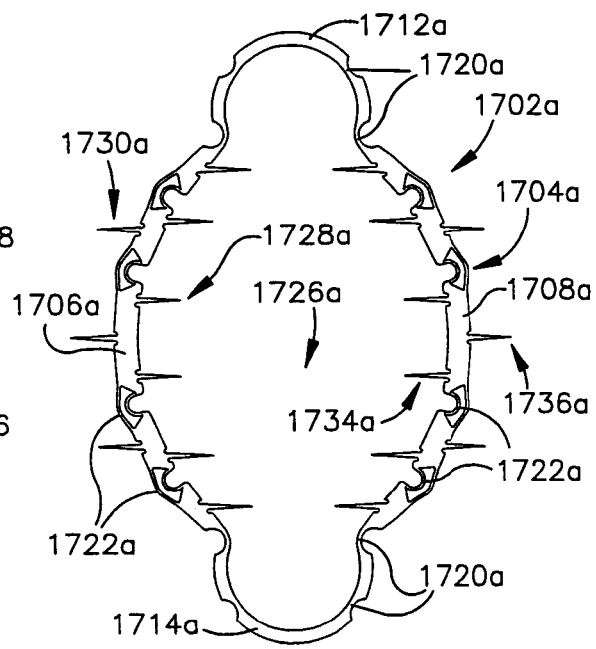
FIG. 55 is a seventh exemplary embodiment of a closure member.

FIG. 55 illustrates a seventh exemplary embodiment of a clip 1702a. The clip 1702a of FIG. 55 is similar to the clip 1702 of FIG. 54 and therefore, structures of FIG. 55 that are the same as or similar to those described with reference to FIG. 54 have the same reference numbers with the addition of the suffix "a".

The clip 1702a of FIG. 55 is identical to the clip 1702 of FIG. 54 with the exception that the tines 1728a, 1730a, 1734a, and 1736a of the clip 1702a extend parallel to one another and not radially relative to a center of the opening 1726a. Again, prior to use, the tines 1728a, 1730a, 1734a, and 1736a are bent to extend at an angle of in the range of approximately twenty to ninety degrees relative to the planar body portion 1704a.

Figure 56:
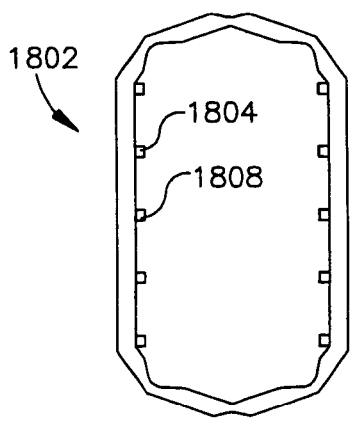
FIG. 56 is an eighth exemplary embodiment of a closure member.
Figure 57:
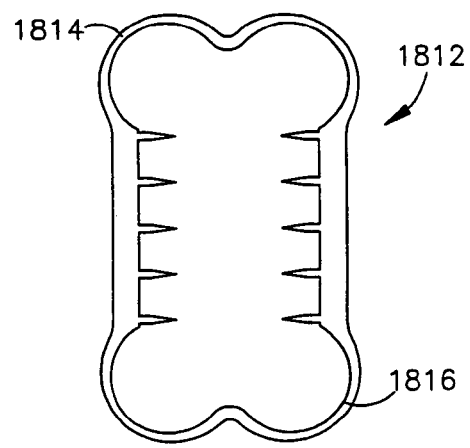
FIG. 57 is a ninth exemplary embodiment of a closure member.
Figure 58:
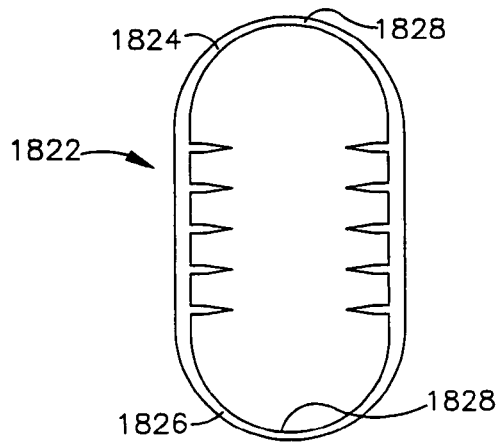
FIG. 58 is a tenth exemplary embodiment of a closure member.
Figure 59:
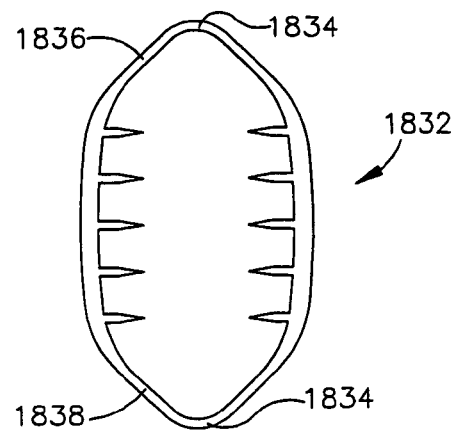
FIG. 59 is an eleventh exemplary embodiment of a closure member.

The clip 1802 of FIG. 56 includes tines 1804 that have planar ends 1808. The clip 1812 of FIG. 57 has a bone-shape with lobed deformable portions 1814 and 1816. The clip 1822 of FIG. 58 is oval. Each of the deformable portions 1824 and 1826 of the clip 1822 of FIG. 58 includes only a single deformation zone 1828. The clip 1832 of FIG. 59 is oblong and, similar to the clip 1822 of FIG. 58, includes only a single deformation zone 1834 in each deformable portion 1836 and 1838. Prior to use, the tines of the clips 1802, 1812, 1822, and 1832 of FIGS. 56-59, respectively, are bent to extend at an angle of in the range of approximately twenty to ninety degrees relative to the planar body portion.

Figure 60:
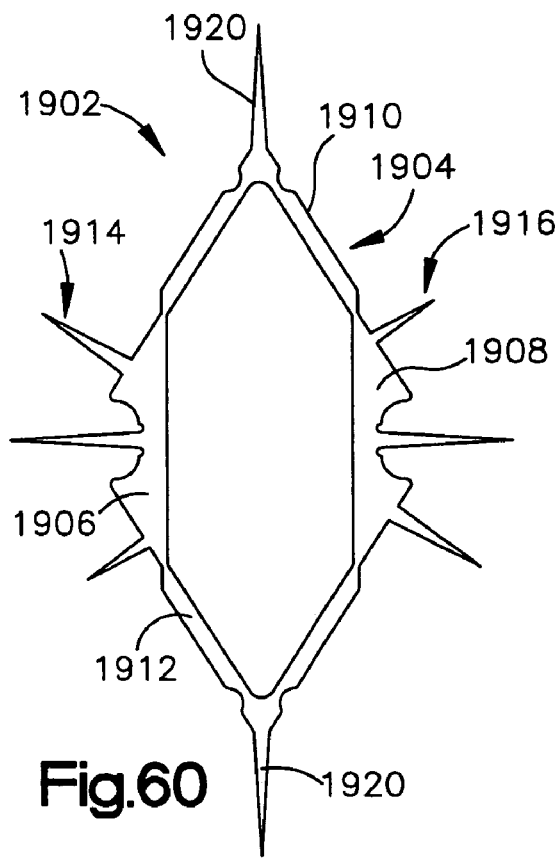
FIG. 60 is a twelfth exemplary embodiment of a closure member.

The clip 1902 of FIG. 60 includes a planar body portion 1904 having first and second retaining portions 1906 and 1908, respectively, and first and second deformable portions 1910 and 1912, respectively. A first set of tines 1914 extends outwardly from the first retaining portion 1906. A second set of tines 1916 extends outwardly from the second retaining portion 1908. A single 1920 tine extends outwardly of each of the deformable portions 1910 and 1912. Prior to use of the clip 1902, the tines 1914, 1916, and 1920 are bent so as to extend at an angle of in the range of approximately twenty to ninety degrees relative to the planar body portion 1904 of the clip 1902. Prior to use, the tines 1914 and 1916 are bent to extend at a ninety degree angle relative to the planar body portion 1904.

Figure 61:
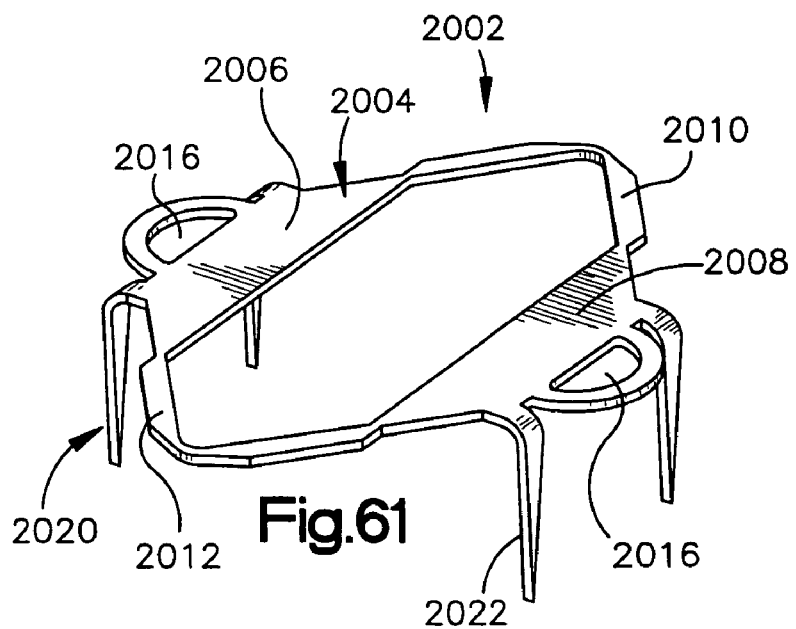
FIG. 61 is a thirteenth exemplary embodiment of a closure member.

The clip 2002 of FIG. 61 includes a planar body portion 2004 having first and second retaining portions 2006 and 2008, respectively, and first and second deformable portions 2010 and 2012, respectively. The first and second retaining portions 2006 and 2008 include docking features 2016 for enabling the first and second retaining portions to be docked onto a closing device. A first set of tines 2020 extends outwardly from and perpendicular to the first retaining portion 2006. A second set of tines 2022 extends outwardly from and perpendicular to the second retaining portion 2008.

Figure 62:
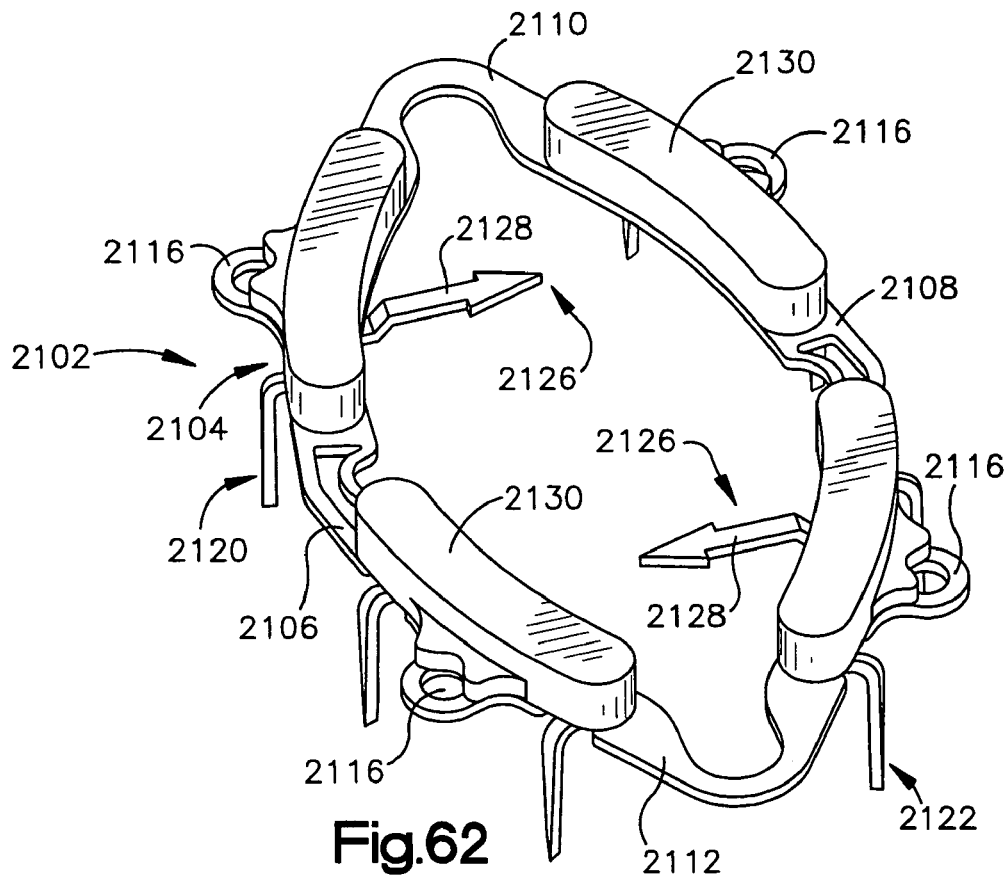
FIG. 62 is a fourteenth exemplary embodiment of a closure member.

FIG. 62 illustrates a clip 2102 that includes a planar body portion 2104 having first and second retaining portions 2106 and 2108, respectively, and first and second deformable portions 2110 and 2112, respectively. The first and second retaining portions 2106 and 2108 include docking features 2116 for enabling the first and second retaining portions to be docked onto a closing device. A first set of tines 2120 extends outwardly from and perpendicular to the first retaining portion 2106. A second set of tines 2122 extends outwardly from and perpendicular to the second retaining portion 2108.

The clip 2102 of FIG. 62 also includes two locking devices 2126. Each locking device 2126 includes a barb 2128 and an associated receiving portion 2130. When the clip 2102 is moved to the closed condition, the barb 2128 of each locking device 2126 pierces its associated receiving portion 2130 and locks in the associated receiving portion.

Figure 63:
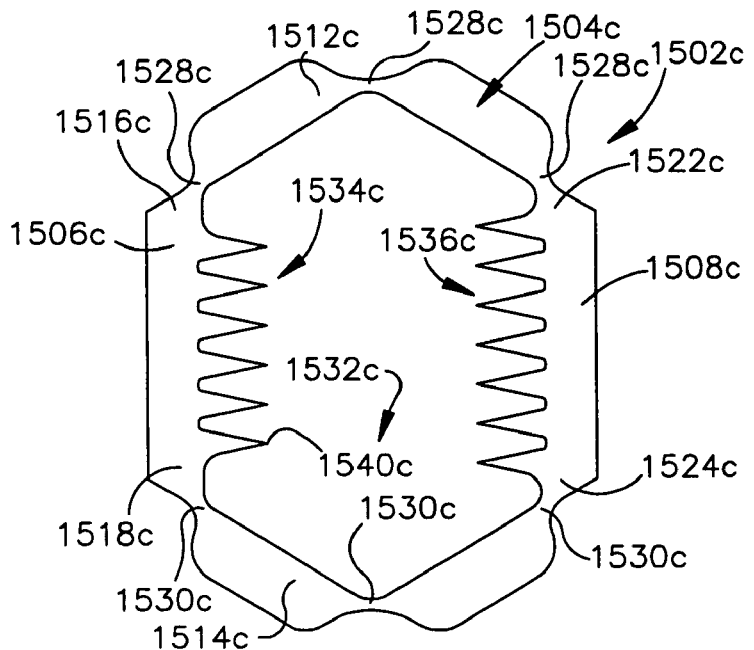
FIG. 63 is a fifteenth exemplary embodiment of a closure member.

FIG. 63 illustrates a fifteenth exemplary embodiment of a clip 1502c. The clip 1502c of FIG. 63 is similar to the clip 1502 of FIG. 49 and therefore, structures of FIG. 63 that are the same as or similar to those described with reference to FIG. 49 have the same reference numbers with the addition of the suffix "c".

The first and second deformable portions 1512c and 1514c, respectively, of the body portion 1504c of the clip 1502c of FIG. 63 are formed from a polymeric material that degrades after a predetermined time period for releasing the clip 1502c from the tissue. In a preferred embodiment of the invention, the first and second deformable portions 1512c and 1514c are formed from an acetyl with a high starch concentration, preferably 10 to 20 percent. The starch absorbs moisture and degrades so that the clip 1502c is released. Preferably, the clip 1502c is released in a period of approximately one to two weeks.

While the present invention has been described as having exemplary structures and methods, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

Having described the invention, we claim the following:

1. A device for excising tissue and closing a wound that results from excision of the tissue, the device comprising:
   structure defining an aperture into which tissue to be excised is exposed;
   a cutting member for excising the tissue;
   a closure member for closing the wound;
   an actuatable drive member associated with the structure, the drive member being actuatable to move the cutting member relative to the aperture for excising the tissue that is exposed in the aperture and for closing the wound with the closure member, the drive member including first and second portions, the first portion of the drive member supporting the cutting member and the second portion of the drive member moving the closure member from an open condition to a closed condition, the closure member, when in the closed condition, closing the wound; and the second portion of the drive member including first and second engaging members, the first and second engaging members being located on opposite sides of the aperture and, during actuation of the drive member, moving toward one another to move the closure member from the open condition to the closed condition; wherein collapsible legs attach the first and second engaging members, movement of the first engaging member being transferred through the collapsible legs to cause movement of the second engaging member in a direction opposite to the movement of the first engaging member.

2. The device of claim 1 wherein the first and second engaging members include portions for supporting the closure member relative to the aperture and portions for moving the closure member from the open condition to the closed condition.

3. The device of claim 1 wherein the second engaging member of the second portion of the drive member is responsive to movement of the first engaging member for moving in a direction opposite to the movement of the first engaging member.

4. The device of claim 3 wherein an endwall of the second portion of the drive member supports the second engaging member, the endwall including pivoting portions that pivot about associated pivot points for moving the second engaging member in a direction opposite to the movement of the first engaging member.

5. A device for excising tissue and closing a wound that results from excision of the tissue, the device comprising:
   structure defining an aperture into which tissue to be excised is exposed;
   a cutting member for excising the tissue;
   a closure member for closing the wound;
   an actuatable drive member associated with the structure, the drive member being actuatable to move the cutting member relative to the aperture for excising the tissue that is exposed in the aperture and for closing the wound with the closure member, the drive member including first and second portions, the first portion of the drive member supporting the cutting member and the second portion of the drive member moving the closure member from an open condition to a closed condition, the closure member, when in the closed condition, closing the wound; and the first portion of the drive member including a support portion for supporting the cutting member, collapsible legs connecting the support portion of the first portion of the drive member to the second portion of the drive member, the support portion moving into engagement with the second portion of the drive member when the collapsible legs collapse.

6. The device of claim 5 wherein the support portion moves into engagement with the second portion of the drive member, further movement of the support portion, after engagement with the second portion of the drive member, causing the second portion of the drive member to move the closure member from the open condition to the closed condition.

7. A device for excising tissue and closing a wound that results from excision of the tissue, the device comprising:
   structure defining an aperture into which tissue to be excised is exposed;
   a cutting member for excising the tissue;
   a closure member for closing the wound;
   an actuatable drive member associated with the structure, the drive member being actuatable to move the cutting member relative to the aperture for excising the tissue that is exposed in the aperture and for closing the wound with the closure member; and
   the drive member including first and second portions, the first portion of the drive member supporting the cutting member and the second portion of the drive member moving the closure member from an open condition to a closed condition in which the closure member closes the wound, the first portion of the drive member including collapsible legs that engage a side surface of a recess in the structure so that, when the drive member is actuated, the second portion of the drive member begins to move the closure member toward the closed condition prior to the collapsible legs collapsing and prior to the first portion of the drive member moving the cutting member to excise the tissue that is pulled through the aperture.

* * * * *